(12) United States Patent
Hanani et al.

(10) Patent No.: US 11,844,891 B2
(45) Date of Patent: Dec. 19, 2023

(54) IMPLANTABLE FLUID EXTRACTION SYSTEM

(71) Applicant: Paragate Medical Ltd., Nazareth (IL)

(72) Inventors: Nitai Hanani, Haifa (IL); Hadar Gilboa, Haifa (IL); Hernan Altman, Kiryat-Tivon (IL)

(73) Assignee: Paragate Medical Ltd., Haifa (IL)

( * ) Notice: Subject to any disclaimer, the term of this patent is extended or adjusted under 35 U.S.C. 154(b) by 898 days.

(21) Appl. No.: 16/613,126

(22) PCT Filed: May 14, 2018

(86) PCT No.: PCT/IL2018/050525
§ 371 (c)(1),
(2) Date: Nov. 13, 2019

(87) PCT Pub. No.: WO2018/211500
PCT Pub. Date: Nov. 22, 2018

(65) Prior Publication Data
US 2020/0197590 A1 Jun. 25, 2020

Related U.S. Application Data

(60) Provisional application No. 62/505,931, filed on May 14, 2017.

(51) Int. Cl.
*A61M 1/28* (2006.01)
*A61M 1/16* (2006.01)
(Continued)

(52) U.S. Cl.
CPC .......... *A61M 1/285* (2013.01); *A61M 1/1623* (2014.02); *A61M 1/267* (2014.02);
(Continued)

(58) Field of Classification Search
CPC .... A61M 1/1623; A61M 1/267; A61M 1/285; A61M 1/602; A61M 1/75; A61M 1/915;
(Continued)

(56) References Cited

U.S. PATENT DOCUMENTS 3,610,238 A * 10/1971 Rich, Jr. ........... A61F 13/00068
604/289
3,707,967 A 1/1973 Kitrilakis et al.
(Continued)

FOREIGN PATENT DOCUMENTS

CN 1469760 1/2004
CN 101389373 3/2009
(Continued)

OTHER PUBLICATIONS

Notice of Reasons for Rejection dated May 10, 2022 From the Japan Patent Office Re. Application No. 2020-512943 and Its Translation Into English. (6 Pages).
(Continued)

*Primary Examiner* — Benjamin J Klein

(57) ABSTRACT

A fluid extraction implantable system shaped and sized to be implanted in a patient, including:
a fluid extraction chamber having a flat and thin shape connected to a draining tube and including at least one external flat surface, wherein the at least one external flat surface is configured to be attached to a tissue surface when a negative pressure is applied on the draining tube, wherein the chamber extracts fluids from the tissue by applying the negative pressure through the flat surface on the attached tissue surface.

23 Claims, 44 Drawing Sheets
(25 of 44 Drawing Sheet(s) Filed in Color)

(51) Int. Cl.
*A61M 1/26* (2006.01)
*A61M 1/00* (2006.01)

(52) U.S. Cl.
CPC .............. *A61M 1/74* (2021.05); *A61M 1/915* (2021.05); *A61M 1/916* (2021.05); *A61M 1/962* (2021.05); *A61M 2205/04* (2013.01); *A61M 2205/18* (2013.01); *A61M 2205/3553* (2013.01); *A61M 2205/52* (2013.01); *A61M 2205/8206* (2013.01); *A61M 2210/1017* (2013.01); *A61M 2210/1085* (2013.01); *A61M 2230/005* (2013.01); *A61M 2230/04* (2013.01); *A61M 2230/06* (2013.01); *A61M 2230/20* (2013.01); *A61M 2230/50* (2013.01)

(58) Field of Classification Search
CPC .. A61M 1/916; A61M 1/962; A61M 2205/04; A61M 2205/18; A61M 2205/3507; A61M 2205/3553; A61M 2205/52; A61M 2205/7554; A61M 2205/8206; A61M 2210/1017; A61M 2210/1085; A61M 2230/005; A61M 2230/04; A61M 2230/06; A61M 2230/20; A61M 2230/50
See application file for complete search history.

(56) References Cited

U.S. PATENT DOCUMENTS

| | | | |
|---|---|---|---|
| 4,437,856 A * | 3/1984 | Valli | A61M 1/285 604/43 |
| 4,490,137 A | 12/1984 | Moukheibir | |
| 5,176,663 A * | 1/1993 | Svedman | A61F 13/0203 604/378 |
| 5,254,084 A * | 10/1993 | Geary | A61M 1/285 604/523 |
| 5,902,336 A | 5/1999 | Mishkin | |
| 6,296,668 B1 | 10/2001 | Desgrandchamps et al. | |
| 6,569,130 B1 | 5/2003 | Levin | |
| 7,309,323 B2 | 12/2007 | Gura et al. | |
| 8,012,118 B2 | 9/2011 | Curtin et al. | |
| 8,211,053 B2 * | 7/2012 | Herbert | A61M 27/002 604/29 |
| 8,632,489 B1 | 1/2014 | Ahmed | |
| 8,641,659 B2 | 2/2014 | Soykan et al. | |
| 8,728,044 B2 * | 5/2014 | Coulthard | A61M 1/88 604/319 |
| 9,060,888 B2 | 6/2015 | Gellman | |
| 9,844,473 B2 * | 12/2017 | Blott | A61M 3/0216 |
| 9,861,734 B2 * | 1/2018 | Al Wakeel | A61M 25/0017 |
| 10,188,830 B2 * | 1/2019 | Loske | A61M 25/09 |
| 10,653,562 B2 * | 5/2020 | Robinson | A61M 1/916 |
| 2003/0109855 A1 | 6/2003 | Solem et al. | |
| 2004/0167634 A1 | 8/2004 | Atala et al. | |
| 2005/0096582 A1 | 5/2005 | Burnett | |
| 2005/0137539 A1 * | 6/2005 | Biggie | A61M 1/98 604/313 |
| 2007/0197957 A1 | 8/2007 | Hunter et al. | |
| 2008/0051696 A1 | 2/2008 | Curtin et al. | |
| 2008/0119802 A1 * | 5/2008 | Riesinger | A61F 13/00068 604/313 |
| 2009/0318844 A1 * | 12/2009 | Burnett | A61M 27/002 604/9 |
| 2010/0036334 A1 * | 2/2010 | Heagle | A61F 13/00995 604/319 |
| 2010/0042034 A1 * | 2/2010 | Riesinger | A61L 15/28 602/44 |
| 2010/0106188 A1 * | 4/2010 | Heaton | A61M 1/964 606/216 |
| 2010/0121159 A1 | 5/2010 | Burnett et al. | |
| 2011/0071415 A1 | 3/2011 | Karwosky et al. | |
| 2011/0208319 A1 | 8/2011 | Laster | |
| 2012/0071841 A1 * | 3/2012 | Bengtson | A61M 1/90 604/319 |
| 2012/0220926 A1 | 8/2012 | Soykan et al. | |
| 2012/0232502 A1 * | 9/2012 | Lowing | A61M 1/962 604/319 |
| 2013/0211322 A1 * | 8/2013 | Degen | A61M 1/28 604/29 |
| 2013/0253409 A1 | 9/2013 | Burnett | |
| 2014/0066841 A1 | 3/2014 | Degen et al. | |
| 2014/0148754 A1 | 5/2014 | Soykan et al. | |
| 2015/0148760 A1 * | 5/2015 | Dodd | A61M 1/732 604/319 |
| 2017/0007808 A1 | 1/2017 | Dalton | |
| 2017/0128654 A1 * | 5/2017 | Feld | A61M 25/10 |
| 2018/0333522 A1 * | 11/2018 | Pratt | A61M 1/916 |

FOREIGN PATENT DOCUMENTS

| | | | |
|---|---|---|---|
| GB | 2423019 A * | 8/2006 | ....... A61F 13/00068 |
| JP | 2010-527247 | 8/2010 | |
| WO | WO 98/16171 | 4/1998 | |
| WO | WO 98/50088 | 11/1998 | |
| WO | WO 02/32479 | 4/2002 | |
| WO | WO 2006/023589 | 3/2006 | |
| WO | WO 2008/055248 | 5/2008 | |
| WO | WO 2009/025807 | 2/2009 | |
| WO | WO 2011/113615 | 9/2011 | |
| WO | WO 2011/141815 | 11/2011 | |
| WO | WO 2012/112932 | 8/2012 | |
| WO | WO 2015/193880 | 12/2015 | |
| WO | WO 2017/015351 | 1/2017 | |
| WO | WO 2018/211500 | 11/2018 | |

OTHER PUBLICATIONS

Requisition by the Examiner dated Sep. 7, 2021 From the Innovation, Science and Economic Development Canada, Canadian Intellectual Property Office Re. Application No. 2,949,755. (5 Pages).
Applicant-Initiated Interview Summary dated Jan. 23, 2019 From the US Patent and Trademark Office Re. U.S. Appl. No. 15/319,000. (3 pages).
Communication Pursuant to Article 94(3) EPC dated Jul. 16, 2019 From the European Patent Office Re. Application No. 15809620.6. (5 Pages).
International Preliminary Report on Patentability dated Dec. 22, 2016 From the International Bureau of WIPO Re. Application No. PCT/IL2015/050598. (7 Pages).
International Preliminary Report on Patentability dated Nov. 28, 2019 From the International Bureau of WIPO Re. Application No. PCT/IL2018/050525. (14 Pages).
International Search Report and the Written Opinion dated Oct. 22, 2018 From the International Searching Authority Re. Application No. PCT/IL2018/050525. (23 Pages).
International Search Report and the Written Opinion dated Oct. 28, 2015 From the International Searching Authority Re. Application No. PCT/IL2015/050598.
Invitation to Pay Additional Fees, Communication Relating to the Results of the Partial International Search and the Provisional Opinion dated Aug. 31, 2018 From the International Searching Authority Re. Application No. PCT/IL2018/050525. (20 Pages).
Notification of Office Action and Search Report dated Jun. 4, 2018 From the State Intellectual Property Office of the People's Republic of China Re. Application No. 201580031804.0. (7 Pages).
Notification of Office Action and Search Report dated Jan. 14, 2019 From the State Intellectual Property Office of the People's Republic of China Re. Application No. 201580031804.0 and Its Summary in English. (6 Pages).
Official Action dated Jun. 11, 2019 From the US Patent and Trademark Office Re. U.S. Appl. No. 15/319,000. (18 Pages).
Official Action dated Oct. 26, 2018 From the US Patent and Trademark Office Re. U.S. Appl. No. 15/319,000. (23 pages).
Supplementary European Search Report and the European Search Opinion dated Jan. 5, 2018 From the European Patent Office Re. Application No. 15809620.6. (8 Pages).
Translation dated Jun. 14, 2018 of Notification of Office Action dated Jun. 4, 2018 From the State Intellectual Property Office of the People's Republic of China Re. Application No. 201580031804.0. (4 Pages).

(56) References Cited

OTHER PUBLICATIONS

Translation dated Jan. 22, 2019 of Notification of Office Action dated Jan. 14, 2019 From the State Intellectual Property Office of the People's Republic of China Re. Application No. 201580031804.0. (1 Page).
Erickson "Size and Shape of Protein Molecules at the Nanometer Level Determined by Sedimentation, Gel Filtration, and Electron Microscopy", Biological Procedures Online, XP055499868, 11(1): 32-51, May 15, 2009.
Flessner "Net Ultrafiltration in Peritoneal Dialysis: Role of Direct Fluid Absorption Into Peritoneal Tissue", Blood Purification, 10(3-4): 136-147, 1992.
Notice of Reasons for Rejection dated Dec. 6, 2022 From the Japan Patent Office Re. Application No. 2020-512943. (4 Pages).
Translation dated Dec. 20, 2022 of Notice of Reasons for Rejection dated Dec. 6, 2022 From the Japan Patent Office Re. Application No. 2020-512943. (5 Pages).
Additional Search Fees Due under Rule 164(2)(a) EPC Dated Sep. 21, 2023 From the European Patent Office Re. Application No. 18732918.0 (8 pages).
Notice of Reason(s) for Rejection Dated Aug. 29, 2023 From the Japan Patent Office Re. Application No. 2020-512943 and Its Machine Translation Into English. (8 Pages).

\* cited by examiner

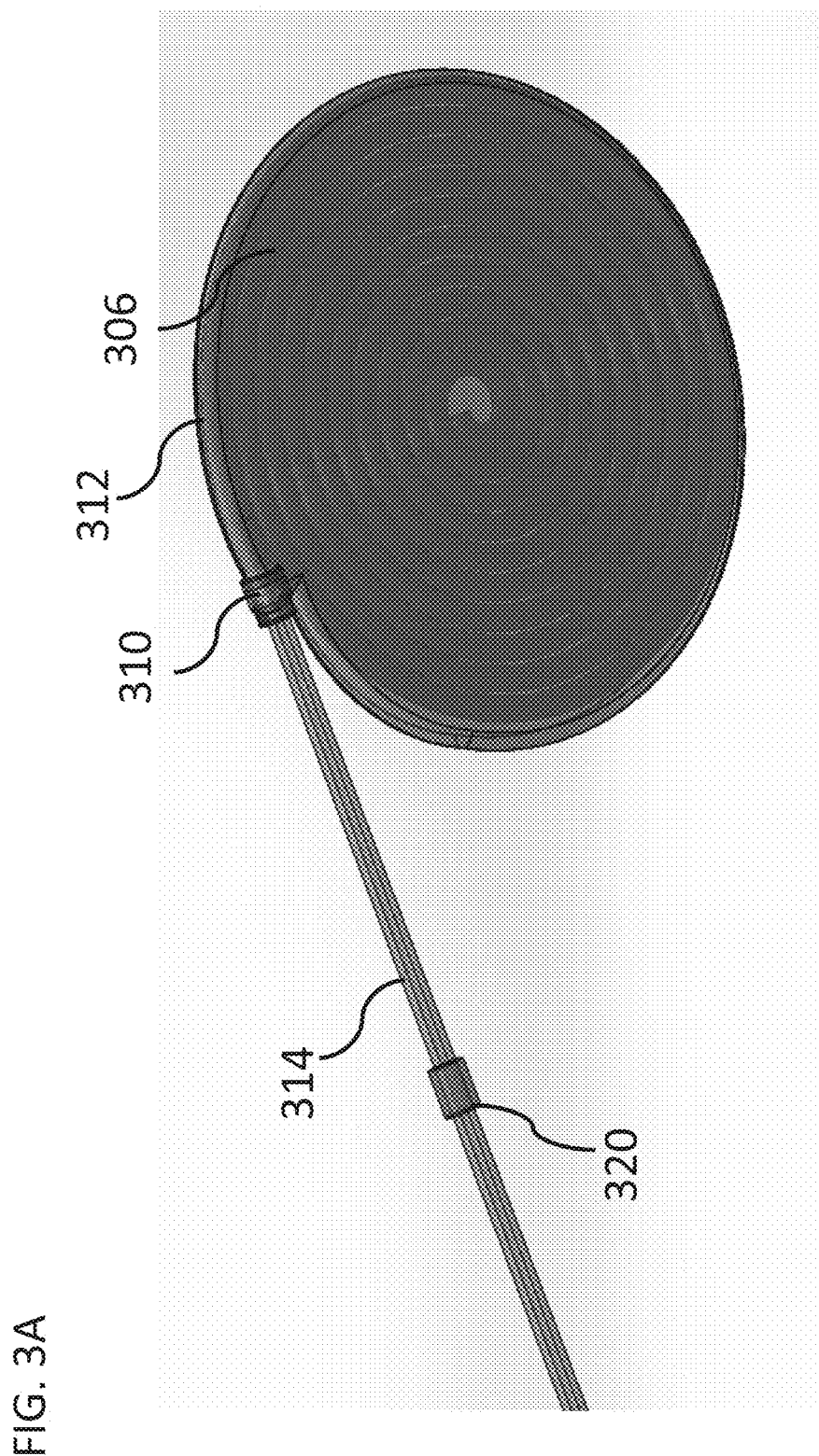

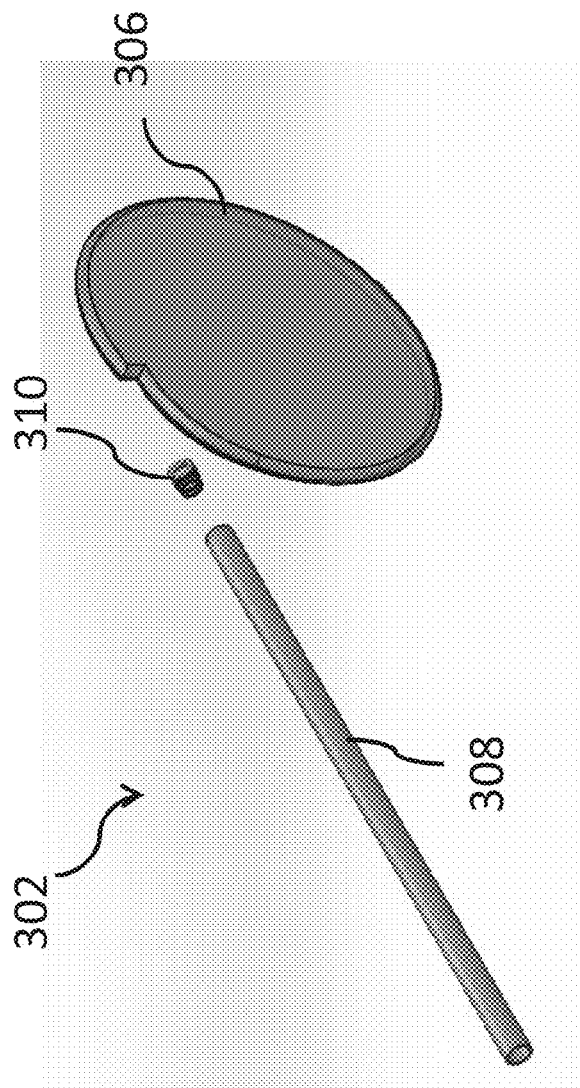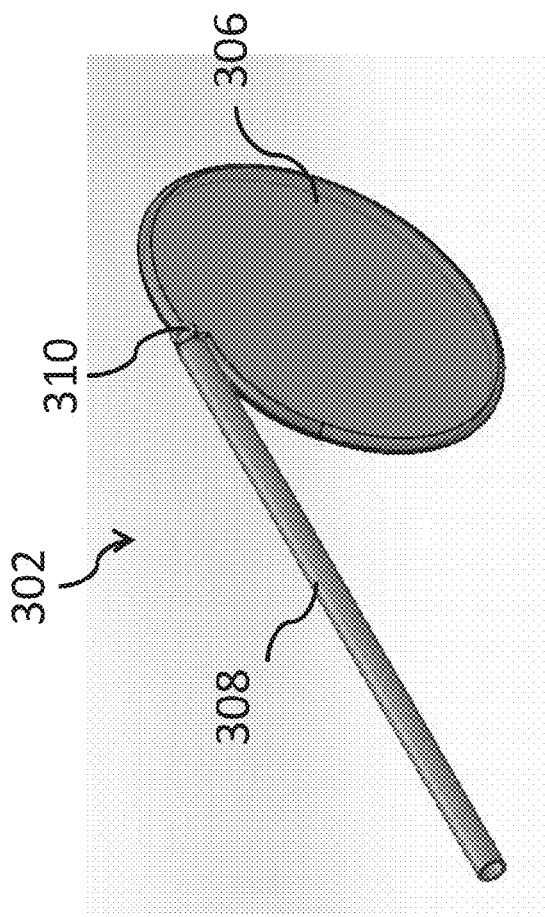

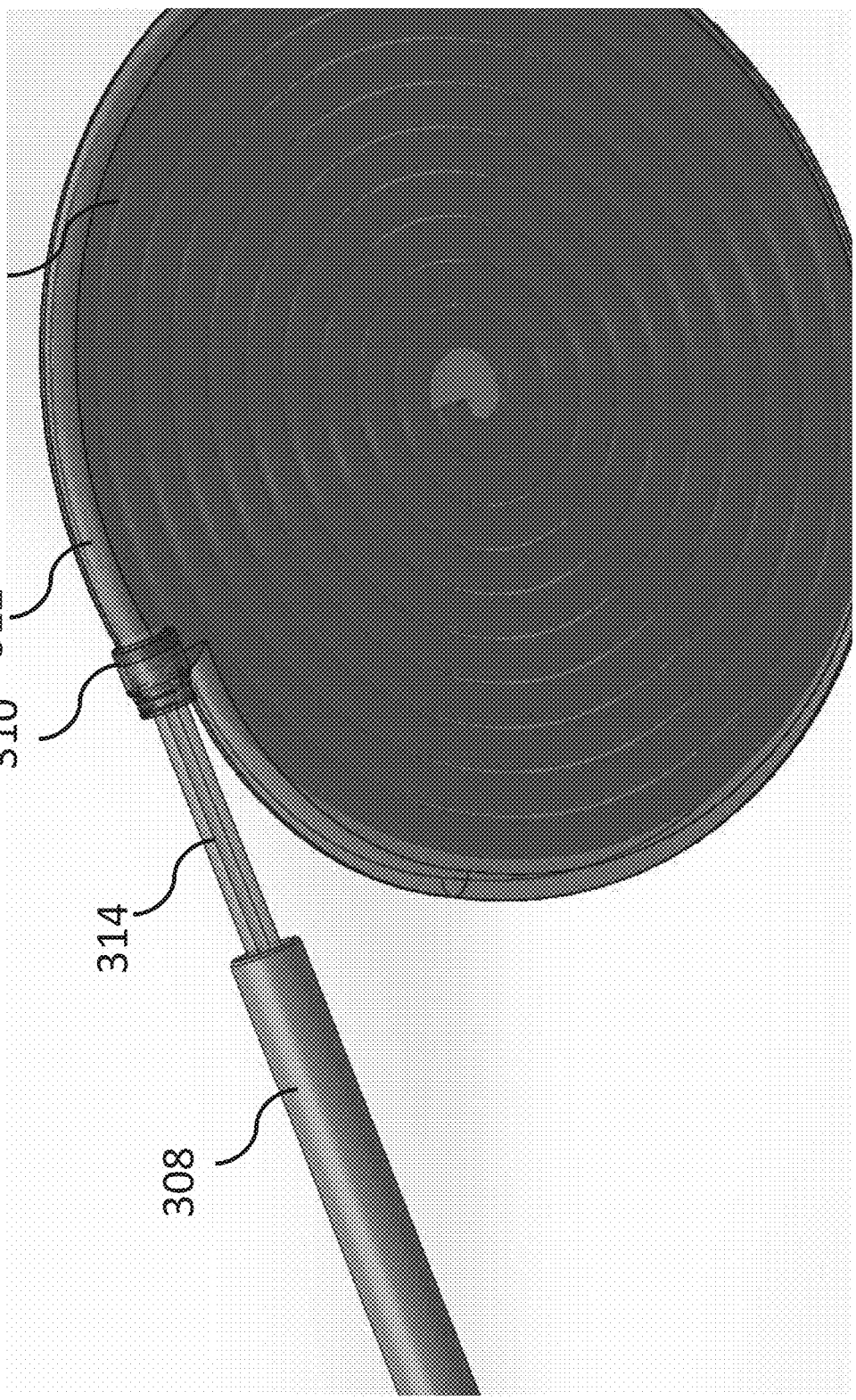

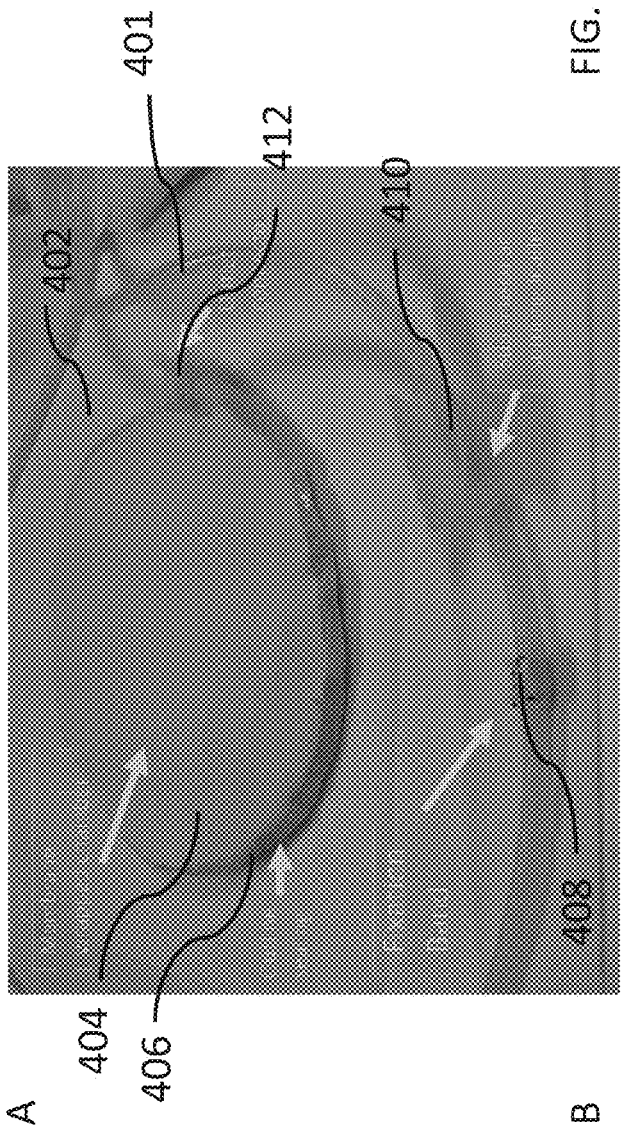
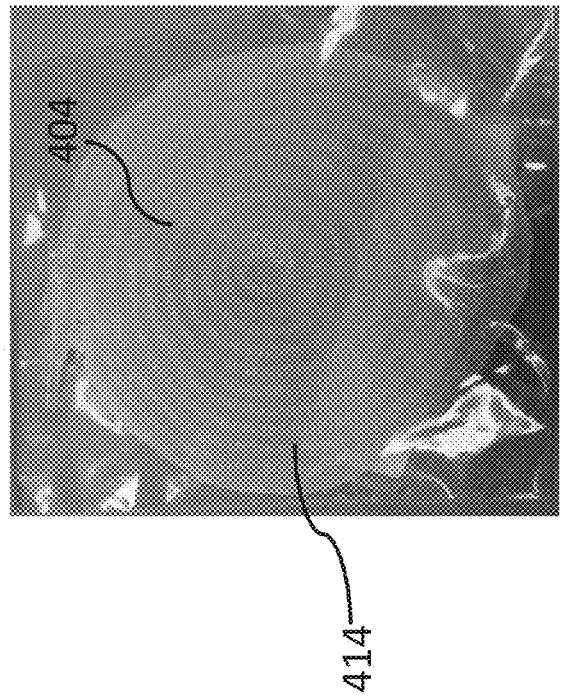
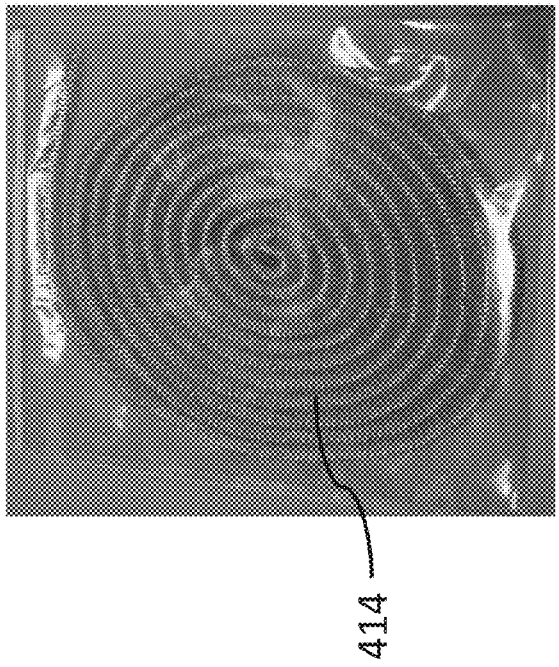
FIG. 4A
FIG. 4B
FIG. 4C

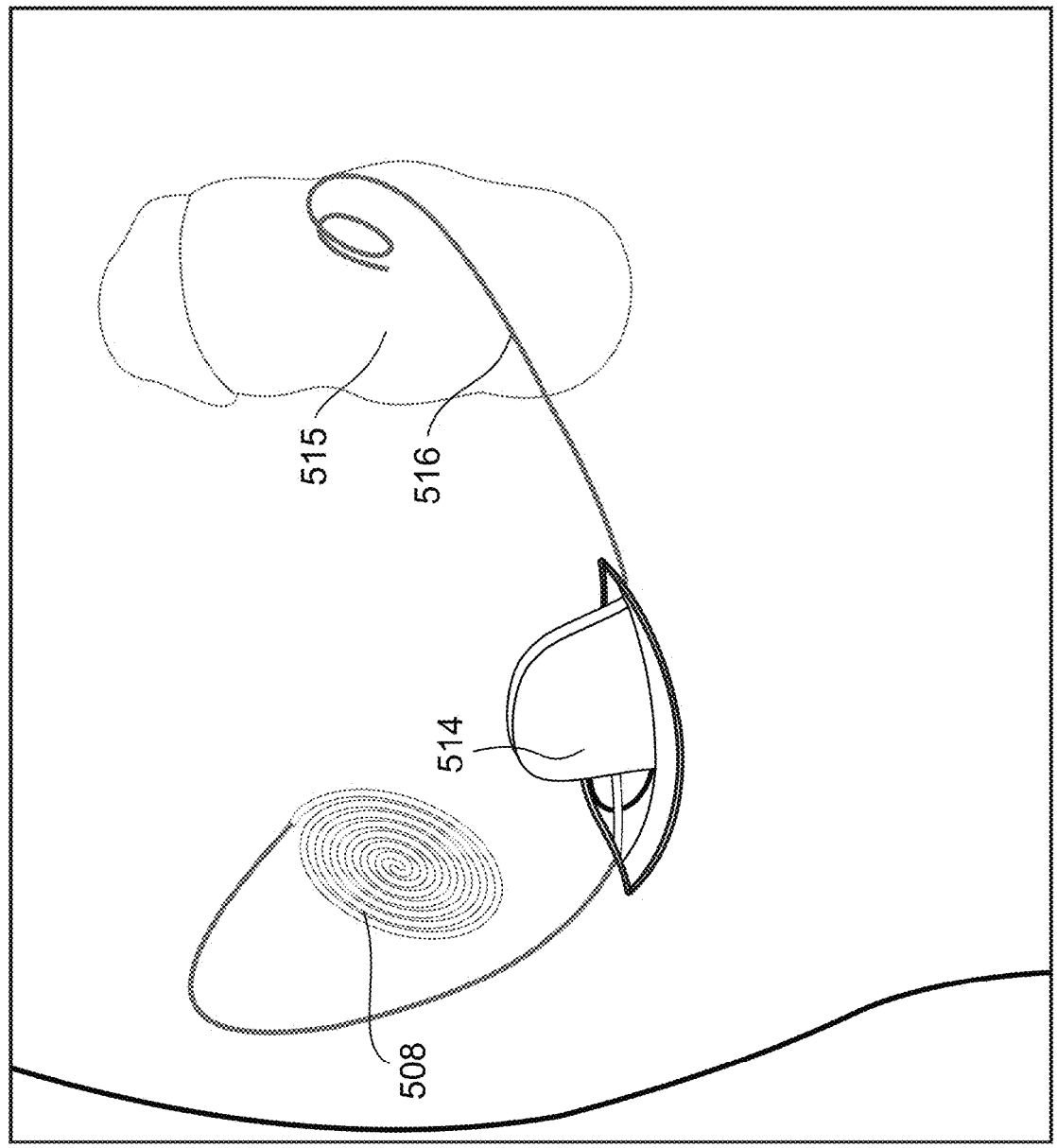

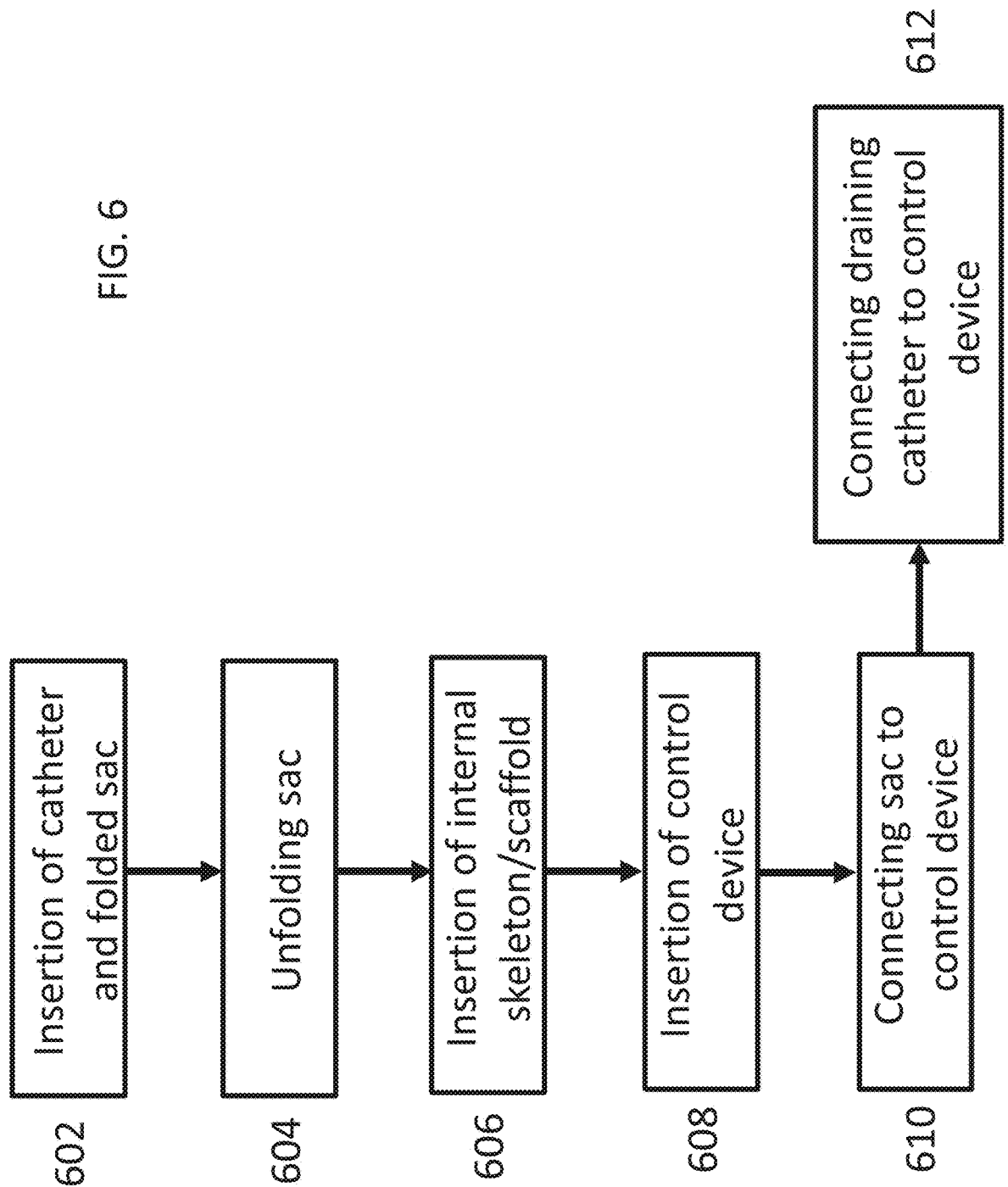

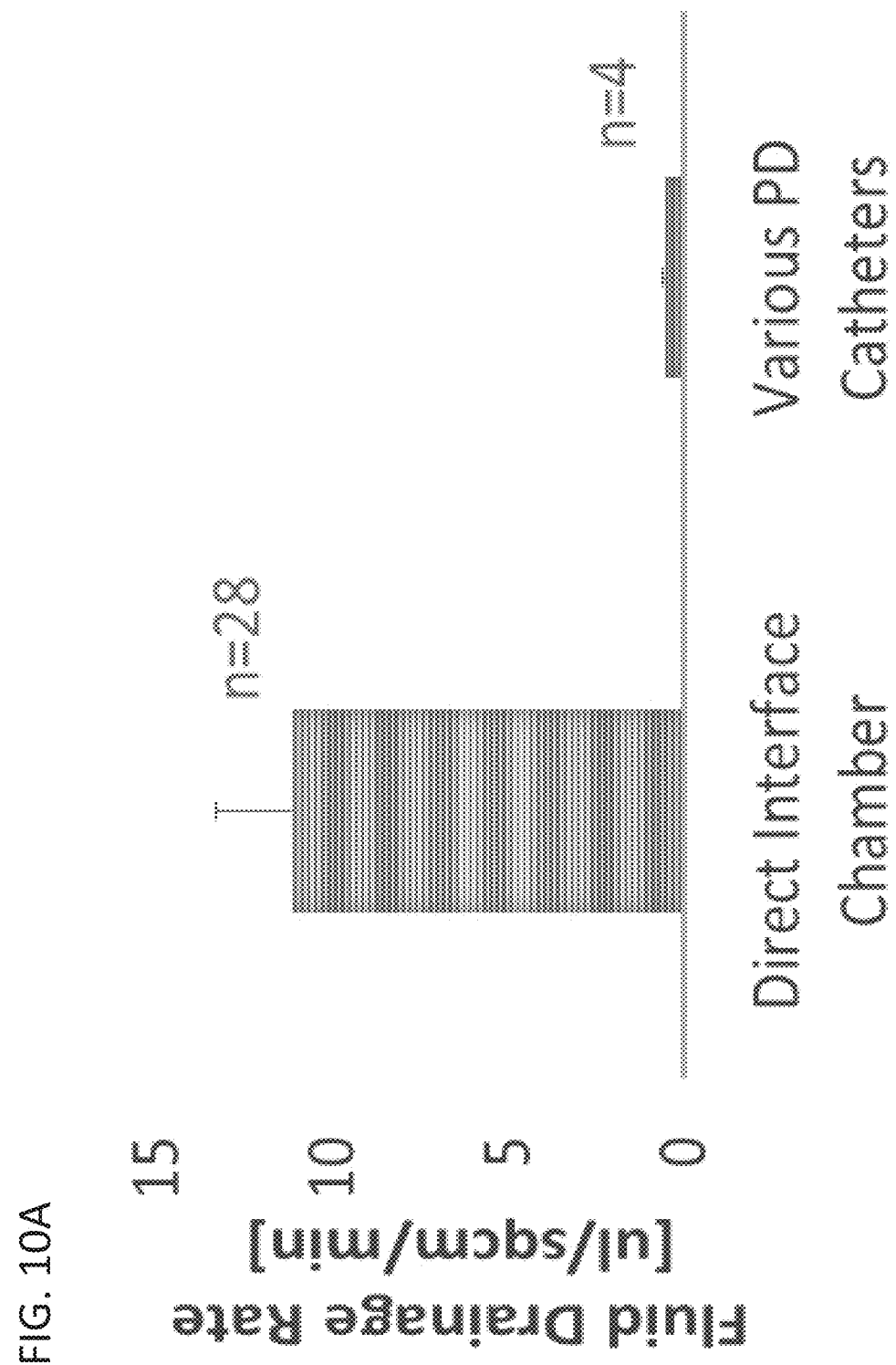

Duty Cycles

FIG. 10G

| Duty cycle [sec ON:OFF] | Elapsed time | pump level | Real drainage Volume | Real avg. drainage rate [ml/min] | Real flow rate [ml/min] (during on cycle) |
|---|---|---|---|---|---|
| 30:150 | 6.5 min | Low | 3ml | 0.46 | 2.0 |
| 60:60 | 11 min | Low | 12.5 | 1.13 | 2.08 |
| 60:420 | 8 min | Low | 2.6* | 0.32 | 1.3 |
| 60:60 | 3 min | High | 2.6 | 0.87 | 0.65 |

IMPLANTABLE FLUID EXTRACTION SYSTEM

RELATED APPLICATIONS

This application is a National Phase of PCT Patent Application No. PCT/IL2018/050525 having International filing date of May 14, 2018, which claims the benefit of priority under 35 USC § 119(e) of U.S. Provisional Patent Application No. 62/505,931 filed on May 14, 2017. The contents of the above applications are all incorporated by reference as if fully set forth herein in their entirety.

FIELD AND BACKGROUND OF THE INVENTION

The present invention, in some embodiments thereof, relates to a fluid extraction system and, more particularly, but not exclusively, to an implanted fluid extraction system.

As described in Flesner et al. (Blood Purif 1992; 10: 136-14), the nature of the fluid that arrives to the peritoneum is 25% lymphatic fluid and 75% circulation and interstitial fluid.

SUMMARY OF THE INVENTION

Some examples of some embodiments of the invention are listed below. It should be noted that features from one example can be combined with one or more features from other examples:

Example 1

A fluid extraction implantable system shaped and sized to be implanted in a patient, comprising:
a fluid extraction chamber connected to a draining tube, wherein said chamber extracts fluids by applying negative pressure on a tissue;
a control unit sized to be implanted subcutaneously connected to said draining tube;
wherein said control unit comprises:
a memory for storing at least one treatment protocol or a portion thereof;
a pump for applying negative pressure on said draining tube;
a control circuitry, wherein said control circuitry activates said pump according to said treatment protocol.

Example 2

The system according to example 1, further comprising at least one implanted physiological sensor connected to said control circuitry; wherein said sensor measures values of at least one physiological parameter related to said patient.

Example 3

The system according to example 2, wherein said at least one physiological parameter comprises interstitial pressure or blood pressure and/or blood content and/or heart rate of said patient.

Example 4

The system according to example 3, wherein said physiological sensor measures levels of Creatinine and/or Albumin and/or Sodium and/or Potassium and/or Urea and/or Phosphate in said blood content.

Example 5

The system according to any one of examples 2 to 4, wherein said at least one physiological parameter comprises an indication of congestion.

Example 6

The system according to any one of examples 2 to 5 wherein said measured values of said at least one physiological parameter are stored in said memory.

Example 7

The system according to example 1, further comprising at least one implanted extract sensor connected to said control circuitry, wherein said sensor measures values of at least one parameter related to the extracted fluid.

Example 8

The system according to example 7, wherein said at least one parameter comprising flow of said extracted fluid and/or pressure of said extracted fluid and/or volume of said extracted fluid.

Example 9

The system according to any one of examples 7 or 8, wherein said at least one parameter comprising levels of biological and/or chemical substances in said extracted fluid.

Example 10

The system according to example 9, wherein said substances comprising Creatinine and/or Albumin and/or Sodium and/or Potassium and/or Urea and/or Phosphate.

Example 11

The system according to example 7, wherein said extract sensor measures congestion or an indication of congestion.

Example 12

The system according to any one of example 7 to 11, wherein said measured values are stored in said memory.

Example 13

The system according to any one of the previous examples, further comprising a catheter fluidically connected to said draining tube, wherein said catheter having a tip connected to the urinary system.

Example 14

The system according to any one of the previous examples further comprising a reservoir fluidically connected to said draining tube, wherein said reservoir is shaped and sized to store said extracted fluids.

Example 15

The system according to any one of the previous examples, wherein said control unit further comprising a communication circuitry connected to said control circuitry, wherein said communication circuitry is connected to a handheld device and/or a remote computer via wireless communication.

Example 16

The system according to example 15, wherein said communication circuitry signals said handheld device and/or said remote computer to generate an alert signal.

Example 17

The system according to examples 15 or 16, wherein said communication circuitry receives information from a handheld device and/or from a remote computer, and wherein said information is stored in said memory.

Example 18

The system according to any one of the previous examples, further comprising a battery connected to said control unit, wherein said battery provides electrical power to said control circuitry and said pump.

Example 19

The system according to example 18, wherein said battery is a rechargeable battery.

Example 20

The system of any one of the previous examples, wherein said fluid extraction chamber is flattened and/or thin.

Example 21

The system according to any one of the previous examples, wherein said fluid extraction chamber is shaped and sized to be in direct contact with said tissue of organs located within the peritoneal cavity.

Example 22

The system according to any one of the previous examples, wherein said fluid extraction chamber is shaped and sized to be in direct contact with column tissue.

Example 23

The system according to any one of the previous examples, wherein said fluid extraction chamber is shaped and sized to be implanted subcutaneously.

Example 24

The system of any one of the previous examples, wherein said control unit is thin.

Example 25

A fluid extraction implantable system shaped and sized to be implanted in a patient, comprising:
a fluid extraction chamber connected to a draining tube, wherein said chamber extracts fluids by applying negative pressure on a tissue;
a control unit sized to be implanted subcutaneously connected to said draining tube;
wherein said control unit comprises:
a sensor for measuring values of at least one outcome of protocol fluid extracting treatment;
a control circuitry connected to said sensor, wherein said control circuitry receives feedback on said treatment by analyzing said values.

Example 26

The system of example 25, further comprising a memory for storing a protocol for said treatment or a portion thereof, and wherein said system further comprises a pump for applying negative pressure on said fluid extraction chamber.

Example 27

The system of example 25, wherein said control unit comprising a communication circuitry for signaling a handheld device or a remote computer to generate an alert signal if said values of said at least one outcome are not in a desired range of values.

Example 28

The system according to any one of examples 25 to 27, wherein said fluid extraction chamber is shaped and sized to be implanted subcutaneously.

Example 29

An implantable fluid extraction chamber, comprising:
a permeable sack preshaped to form a thin body, wherein said sack comprises an opening;
an internal scaffold configured to be deployed through said opening into said sack, wherein said internal scaffold maintains said thin body of said sack.

Example 30

The chamber according to example 29, wherein said chamber is small enough to be positioned within the peritoneum.

Example 31

The chamber according to examples 29 or 30, wherein said permeable sack is preshaped to form a flat and thin body.

Example 32

The chamber according to example 29, further comprising a porous membrane layer on the outer surface of said sack.

Example 33

The chamber according to example 29, further comprising a porous membrane within a cavity of said sack.

Example 34

The chamber according to example 29, wherein said sack is at least partly made from a porous membrane layer.

Example 35

The chamber according to any one of examples 29 to 34, wherein said internal scaffold comprises an inner elongated stylet positioned inside a lumen of said internal scaffold, wherein said stylet maintains said thin body of said permeable sack.

Example 36

The chamber according to example 35, wherein said inner stylet has a flattened thinned cross section.

Example 37

The chamber according to example 35, wherein said inner stylet has a rectangular cross section.

Example 38

The chamber according to example 35, wherein said inner stylet has a round cross section.

Example 39

The chamber according to any one of examples 35 to 38, wherein said inner stylet is made from a shape memory material.

Example 40

The chamber according to any one of examples 32 to 34, wherein a larger dimension of pores of said membrane is smaller than 10 micrometer.

Example 41

The chamber according to any one of examples 31 to 40, wherein said internal scaffold comprises a connector, and wherein said connector restricts the movement of said internal scaffold relative to said sack.

Example 42

The chamber according to any one of examples 29 to 41, wherein said internal scaffold comprises a tube.

Example 43

The chamber according to example 29, wherein said internal scaffold comprises a plurality of beads.

Example 44

The chamber according to example 43, wherein said beads comprises ionically charged beads.

Example 45

The chamber according to examples 43 or 44, wherein a smallest dimension of said beads is at least 1 mm diameter.

Example 46

The chamber according to any one of examples 29 to 45, wherein said sack comprising two flat layers connected to each other along the periphery of said layers; and wherein said two flat layers are connected in at least one connection point in a region enclosed by said periphery.

Example 47

The chamber according to example 29, wherein said internal scaffold comprises a network of tubes.

Example 48

The chamber of example 47, wherein said network of tubes is filled with a gel or with a self-polymerizing material.

Example 49

The chamber of examples 47 or 48, wherein an outer surface of said sack is made from a porous membrane.

Example 50

The chamber according to examples 47 or 48 wherein said chamber comprises a porous membrane layer on the outer surface of said sack.

Example 51

The chamber of examples 47 or 48, wherein said chamber comprises a porous membrane within a cavity of said sack.

Example 52

An implantable fluid extraction chamber, comprising:
a permeable sack comprising two flat layers connected to each other along the periphery of said layers;
wherein said two flat layers are connected in at least one connection point in a region enclosed by said periphery.

Example 53

A fluid extraction implantable system shaped and sized to be implanted in a patient, comprising:
a fluid extraction chamber connected to a draining tube, wherein said chamber extracts fluids by applying negative pressure on a tissue;
a control unit connected to said draining tube; wherein said control unit comprises:
a pump, wherein said pump applies negative and positive pressure on said draining tube.

Example 54

The system according to example 53, wherein said fluid extraction chamber applies higher and lower intensities of said negative pressure.

Example 55

The system according to examples 53 or 54, wherein a control circuitry of said control unit signals said pump to apply higher and lower intensities of said negative and positive pressure.

Example 56

The system according to any one of examples 53 to 55, wherein said pump is a rotary pump, and wherein said rotary pump rotates in opposite directions to apply said negative and positive pressure.

Example 57

A method for deploying a fluid extraction chamber, comprising:
introducing a flattened fluid extraction chamber having a draining outlet into a body cavity;
inserting an internal scaffold into a cavity of said chamber;
connecting said draining outlet to a sink.

Example 58

The method of example 57, wherein said sink comprises a reservoir, urine bladder or renal pelvis.

Example 59

The method according to example 57, comprising restricting the movement of said internal relative to said flattened fluid extraction chamber.

Example 60

The method according to any one of examples 57 to 59, wherein said connecting comprising connecting said draining outlet to a pump.

Example 61

The method according to any one of examples 57 to 60, wherein said introducing comprises introducing said flattened fluid extraction chamber by an introduction element connected to said draining outlet, wherein said introduction element is more rigid than said draining outlet.

Example 62

The method according to any one of examples 57 to 61, wherein said introducing comprises introducing a folded flattened fluid extraction chamber having a draining outlet into a body cavity.

Example 63

The method according to example 62, further comprising unfolding said folded flattened fluid extraction chamber after said introducing.

Example 64

A method for modifying a fluid extraction treatment, comprising:
measuring values of at least one physiological parameter related to said treatment by at least one sensor of a control unit while treating a patient;
modifying a protocol of said treatment or a portion thereof based on said measuring by a control circuitry of said unit.

Example 65

The method according to example 64, wherein said measuring comprising measuring values of at least one physiological parameter of said patient, wherein said physiological parameter comprises fluid congestion, blood pressure, body weight and/or heart rate.

Example 66

The method according to examples 64 or 65, wherein said measuring comprises measuring congestion or an indication for congestion.

Example 67

The method according to example 66, further comprising assessing the recovery time of interstitial pressure based on said congestion or indication of congestion.

Example 68

The method according to example 67, wherein said modifying comprises modifying pressure applied on tissue, pressure application duration and/or duty cycles based on results of said assessing.

Example 69

The method according to any one of examples 64 to 68, wherein said measuring comprising measuring levels of a biological substance and/or a chemical substance in the blood of said patient.

Example 70

The method of any one of examples 64 to 69, wherein said measuring comprising measuring values of at least one parameter related to fluids extracted from said patients.

Example 71

The method according to example 70, wherein said at least one parameter related to said extracted fluids comprises flow of said extracted fluids, pressure of said extracted fluids, volume of said extracted fluids.

Example 72

The method according to examples 70 or 71, wherein said at least one parameter related to said extracted fluids comprise levels of biological and/or chemical substances within said extracted fluids.

Example 73

The method according to example 72, wherein said biological and/or chemical substances comprise Creatinine, Urea, Sodium, Potassium, Phosphate, and/or Albumin.

Example 74

The method of any one of examples 64 to 73 comprising storing said measured value in a memory of said control unit.

Example 75

A method for extracting fluids from a tissue by a fluid extraction chamber implanted in the peritoneum, comprising:
placing said fluid extraction chamber in contact with said tissue actively applying high levels of negative pressure followed by low levels of negative pressure by a pump on said chamber.

Example 76

A method for modifying a fluid extraction treatment by a device and a second treatment, comprising:
measuring values of at least one outcome of said treatments;
modifying said fluid extraction treatment and/or said second treatment based on said measured values of said at least one outcome.

Additional examples of some embodiments of the invention are listed below. It should be noted that features from one example can be combined with one or more features from other examples:

Example 1

A fluid extraction implantable system shaped and sized to be implanted in a patient, comprising:
a fluid extraction chamber having a flat and thin shape connected to a draining tube and comprising at least one external flat surface, wherein said at least one external flat surface is configured to be attached to a tissue surface when a negative pressure is applied on said draining tube, wherein said chamber extracts fluids from said tissue by applying said negative pressure through said flat surface on said attached tissue surface.

Example 2

The system according to example 1, comprising a control unit connected to said draining tube, wherein said control unit comprises a pump for applying said negative pressure on said draining tube.

Example 3

The system according to any one of examples 1 or 2, comprising an internal skeleton configured to be inserted into said fluid extraction chamber and to stretch said fluid extraction chamber to maintain said flat and thin shape.

Example 4

The system according to example 3, wherein said internal skeleton comprises an elastic metal mesh.

Example 5

The system according to example 2, wherein said control unit comprises:
a memory for storing at least one treatment protocol or a portion thereof;
a control circuitry, wherein said control circuitry activates said pump according to said treatment protocol.

Example 6

The system according to example 5, wherein said control circuitry signals said pump to intermittently apply said negative pressure on said draining tube.

Example 7

The system according to any one of examples 1 to 6, wherein said fluid extraction chamber comprises a porous membrane, and wherein said at least one flat surface is a flat surface of said porous membrane.

Example 8

The system according to example 7, wherein said porous membrane comprises a plurality of pores and wherein a width of said pores is smaller than 5 µm.

Example 9

The system according to any one of the previous examples, wherein said at least one flat surface is shaped and sized to conform at least partly to the shape and/or to the contour of said attached tissue.

Example 10

The system according to example 5, further comprising at least one implanted physiological sensor connected to said control circuitry; wherein said sensor measures values of at least one physiological parameter related to said patient.

Example 11

The system according to example 10, wherein said at least one physiological parameter comprises interstitial pressure and/or blood pressure and/or blood content and/or heart rate of said patient.

Example 12

The system according to example 11, wherein said physiological sensor measures levels of Creatinine and/or Albumin and/or Sodium and/or Potassium and/or Urea and/or Phosphate in said blood content.

Example 13

The system according to any one of examples 10 to 12, wherein said at least one physiological parameter comprises an indication of congestion.

Example 14

The system according to example 5, further comprising at least one implanted extract sensor connected to said control circuitry, wherein said sensor measures values of at least one parameter related to the extracted fluid.

Example 15

The system according to example 14, wherein said at least one parameter comprising flow of said extracted fluid and/or pressure of said extracted fluid and/or volume of said extracted fluid.

Example 16

The system according to any one of examples 14 or 15, wherein said at least one parameter comprising levels of biological and/or chemical substances in said extracted fluid.

Example 17

The system according to example 16, wherein said substances comprising Creatinine and/or Albumin and/or Sodium and/or Potassium and/or Urea and/or Phosphate.

Example 18

The system according to any one of examples 14 to 17, wherein said extract sensor measures congestion or an indication of congestion.

Example 19

The system according to any one of the previous examples, further comprising a catheter fluidically connected to said draining tube, wherein said catheter having a tip connected to the urinary system.

Example 20

The system according to any one of the previous examples further comprising a reservoir fluidically connected to said draining tube, wherein said reservoir is shaped and sized to store said extracted fluids.

Example 21

The system according to example 5, wherein said control unit further comprising a communication circuitry connected to said control circuitry, wherein said communication circuitry is connected to a handheld device and/or a remote computer via wireless communication.

Example 22

The system according to example 21, wherein said communication circuitry signals said handheld device and/or said remote computer to generate an alert signal.

Example 23

The system according to examples 21 or 22, wherein said communication circuitry receives information from a handheld device and/or from a remote computer, and wherein said information is stored in said memory.

Example 24

The system according to example 5, further comprising a battery connected to said control unit, wherein said battery provides electrical power to said control unit.

Example 25

The system according to any one of the previous examples, wherein said fluid extraction chamber is shaped and sized to be in direct contact with said tissue of organs located within the peritoneal cavity.

Example 26

The system according to any one of the previous examples, wherein said fluid extraction chamber is shaped and sized to be implanted subcutaneously.

Example 27

An implantable fluid extraction chamber, comprising:
a permeable sack preshaped to form a flat and thin body, wherein said sack comprises an opening;
an elastic internal scaffold configured to be deployed through said opening into said sack, wherein said elastic internal scaffold stretches said sack to maintain said flat and thin body of said sack.

Example 28

The chamber according to example 27, wherein said elastic internal scaffold is rigid enough to prevent inward collapse of the permeable sack when vacuum is applied at an inner lumen of the permeable sack.

Example 29

The chamber according to any one of examples 27 or 28, wherein said chamber is small enough to be positioned within the peritoneum.

Example 30

The chamber according to any one of examples 27 to 29 further comprising a porous membrane layer on the outer surface of said sack.

Example 31

The chamber according to any one of examples 27 to 29, further comprising a porous membrane within a cavity of said sack.

Example 32

The chamber according to any one of examples 27 to 29, wherein said sack is at least partly made from a porous membrane layer.

Example 33

The chamber according to any one of examples 27 to 32, wherein said internal scaffold comprises an inner elongated stylet positioned inside a lumen of said internal scaffold, wherein said stylet maintains said thin body of said permeable sack.

Example 34

The chamber according to claim 33, wherein said inner stylet has a flattened thinned cross section or a rounded cross section.

Example 35

The chamber according to any one of examples 27 to 34, wherein said internal scaffold comprises a braided tube.

Example 36

The chamber according to any one of examples 30 to 32, wherein a largest dimension of pores of said membrane is smaller than 5 µm.

Example 37

The chamber according to any one of examples 27 to 36, wherein said internal scaffold comprises a connector, and wherein said connector restricts the movement of said internal scaffold relative to said permeable sack.

Example 38

The chamber according to any one of examples 27 to 37, wherein said permeable sack comprising two flat layers connected to each other along the periphery of said layers; and wherein said two flat layers are connected in at least one connection point in a region enclosed by said periphery.

Example 39

The chamber according to any one of examples 27 to 38, wherein said internal scaffold comprises a tube or a plurality of beads.

Example 40

A fluid extraction implantable system shaped and sized to be implanted in a patient, comprising:
a fluid extraction chamber connected to a draining tube, wherein said fluid extraction chamber having at least one flat and porous external membrane shaped and sized to be in contact with a tissue surface,
a control unit connected to said draining tube, wherein said control unit controls the generation of up and down levels of negative pressure on said draining tube according to a protocol, to mechanically vibrate said at least one flat and porous external membrane.

Example 41

The system of example 40, wherein said control unit comprises:
a vacuum pump connected to said draining tube and configured to generate negative pressure;
a control circuitry electrically connected to said pump configured to control the generation of said negative pressure by said pump.

Example 42

The system of example 41, wherein said control circuitry signals said vacuum pump to generate short bursts of low level negative pressure sufficient to generate said negative pressure applied on said draining tube.

Example 43

The system of any one of examples 41 or 42, comprising at least one valve electrically connected to said control circuitry and positioned on said draining tube, wherein said control circuitry signals said valve to close and to open said draining tube while said vacuum pump generates said negative pressure.

Example 44

The system of any one of examples 41 to 43, comprising a flow path connecting said draining tube and an outlet of said pump, and at least one valve controlled by said control circuitry and positioned on said flow path, wherein said at least one valve controls flow through said flow path.

Example 45

The system of example 44, wherein said control circuitry signals said valve to close and to open said flow path while said pump generates said negative pressure.

Example 46

A method for deploying a fluid extraction chamber, comprising:
introducing a flattened fluid extraction chamber having a draining outlet into a body cavity;
inserting an elastic internal scaffold into a cavity of said chamber in order to shape said flattened chamber;
connecting said draining outlet to a sink.

Example 47

The method of example 46, wherein said sink comprises a reservoir, urine bladder or renal pelvis.

Example 48

The method according to any one of examples 46 or 47, comprising connecting said internal scaffold to a port of said flattened chamber for restricting the movement of said internal scaffold relative to said flattened fluid extraction chamber.

Example 49

The method according to any one of claims 46 to 48, wherein said connecting comprising connecting said draining outlet to a pump.

Example 50

The method according to example 49, comprising applying negative pressure by said pump through said draining outlet on an internal lumen of said flattened fluid extraction chamber.

Example 51

The method according to example 50, comprising tightly attaching an external surface of said flattened fluid extraction chamber to a tissue surface during said applying of said negative pressure.

Example 52

The method according to any one of examples 46 to 51, wherein said introducing comprises introducing said flattened fluid extraction chamber by an introduction element connected to said draining outlet, wherein said introduction element is more rigid than said draining outlet.

Example 53

The method according to any one of examples 46 to 52, wherein said introducing said flattened fluid extraction chamber comprises introducing a folded flattened fluid extraction chamber having a draining outlet into a body cavity.

Example 54

The method according to example 53, further comprising unfolding said folded flattened fluid extraction chamber after said introducing.

Example 55

A method for modifying a subject, comprising:

placing at least one flattened surface of a thin fluid extraction chamber in a direct contact with a surface of a tissue;

actively applying negative pressure by a pump on a draining tube connected to said chamber;

maintaining said negative pressure in constant or varying levels sufficient to remove at least 100 ml of fluid per day from said subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as monitoring and modifying a fluid extraction treatment, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a block diagram of an implantable system and device for removing fluid from a bodily organ, according to some embodiments of the invention;

FIG. 2A is a schematic illustration showing interactions of an implantable system for removing fluids from a bodily with external elements, according to some embodiments of the invention;

FIG. 2B is a flow chart describing fluids flow between biological compartments and the implanted system, according to some embodiments of the invention;

FIGS. 3A-3N are schematic illustrations of a fluid extraction chamber with an internal spiral scaffold, according to some embodiments of the invention;

FIGS. 4A-4C are images of a membrane covered fluid extraction chamber with an internal spiral scaffold, according to some embodiments of the invention;

FIGS. 5A-5G are schematic illustrations of a deployment process of a fluid extracting system comprising a fluid extraction chamber with an internal spiral scaffold, according to some embodiments of the invention;

FIG. 6 is a flow chart describing a deployment process of a fluid extracting system comprising a fluid extraction chamber with an internal spiral scaffold, according to some embodiments of the invention;

FIG. 7A is an image of a beads-filled fluid extraction chamber, according to some embodiments of the invention;

FIG. 7B is a flow chart describing a deployment process of a bead-filled extraction chamber, according to some embodiments of the invention;

FIG. 8A is an image of a gel-filled fluid extraction chamber, according to some embodiments of the invention;

FIG. 8B is a flow chart describing a deployment process of a gel-filled extraction chamber, according to some embodiments of the invention;

Figure 9A:
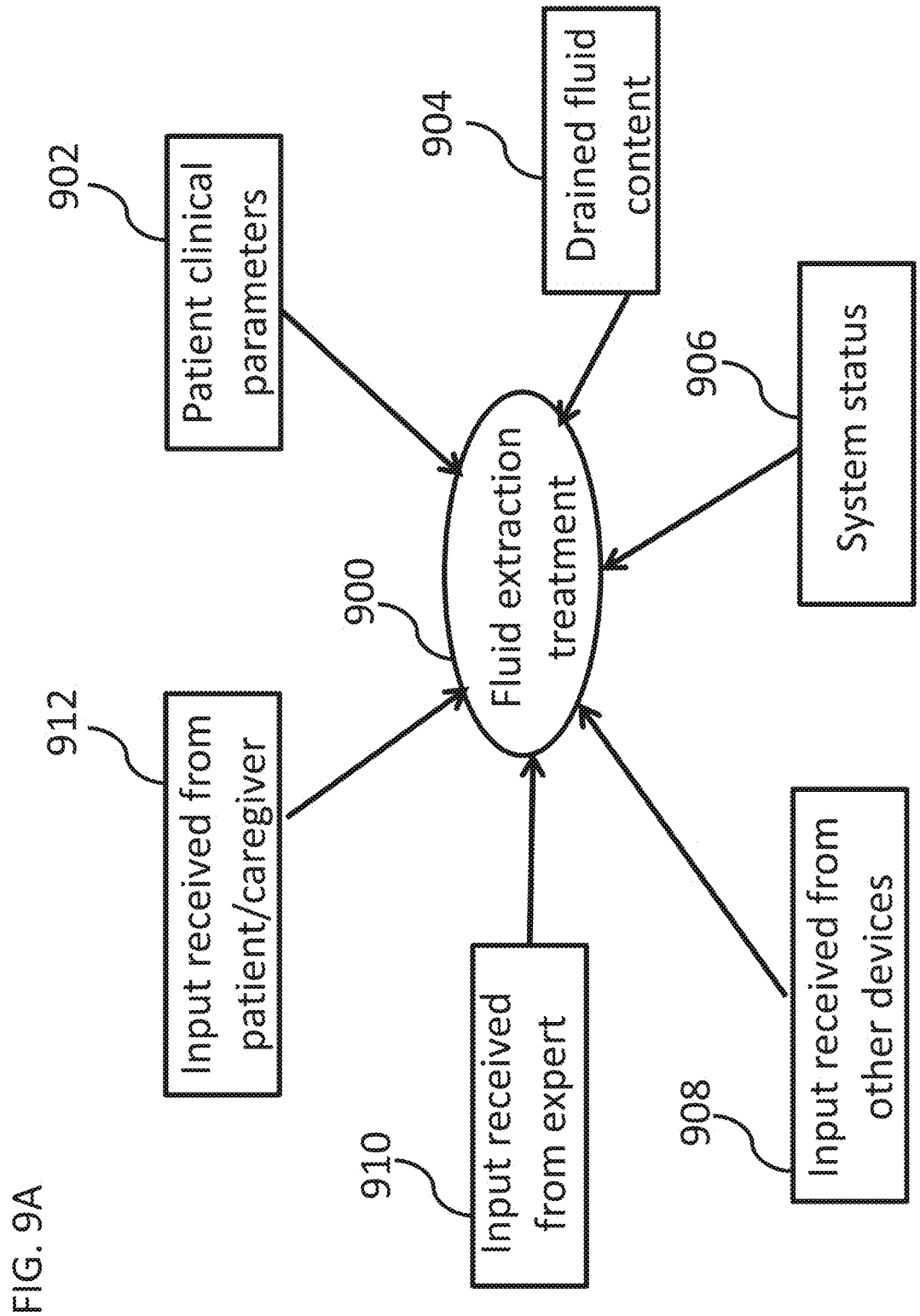
Figure 9B:
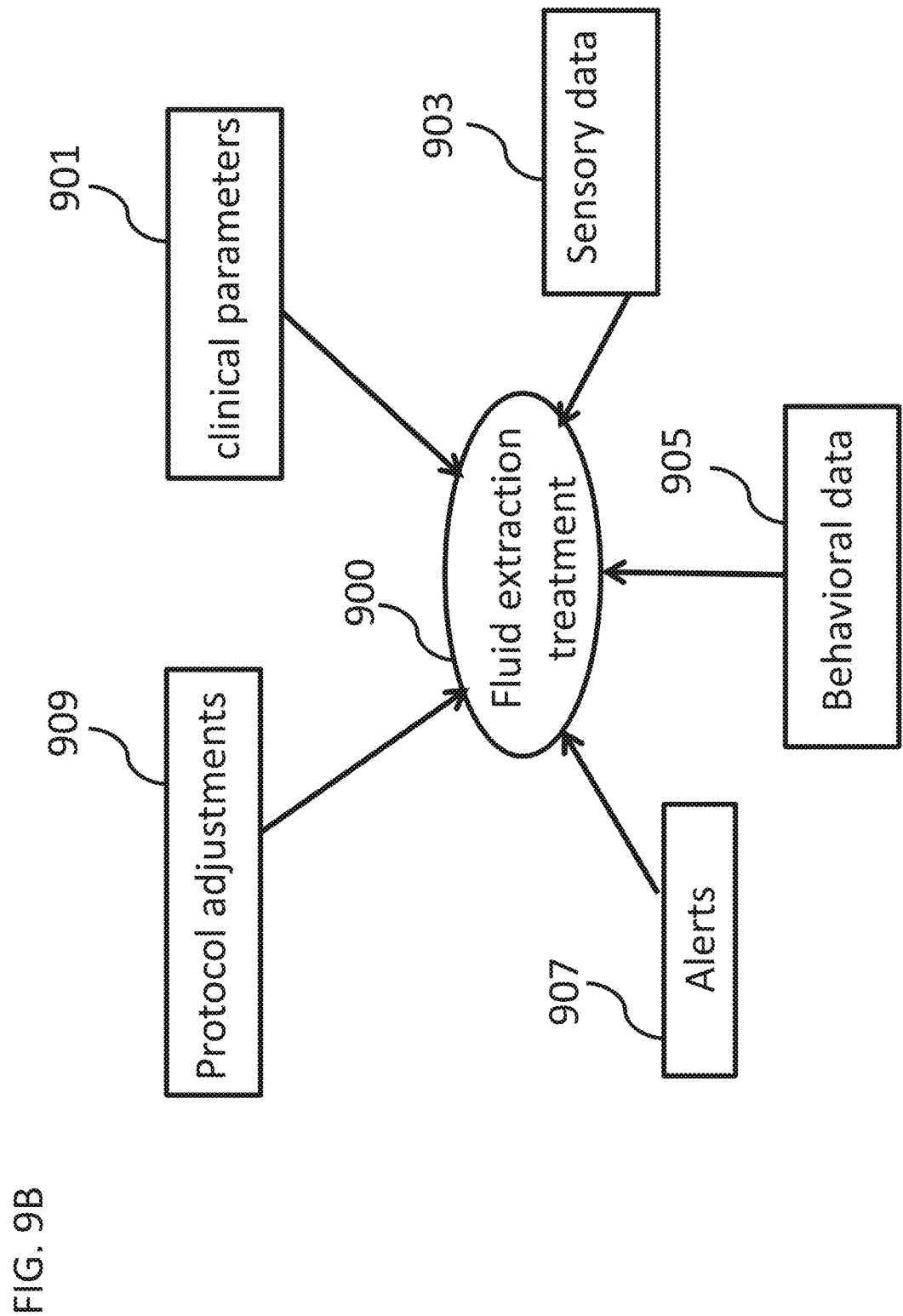
Figure 9C:
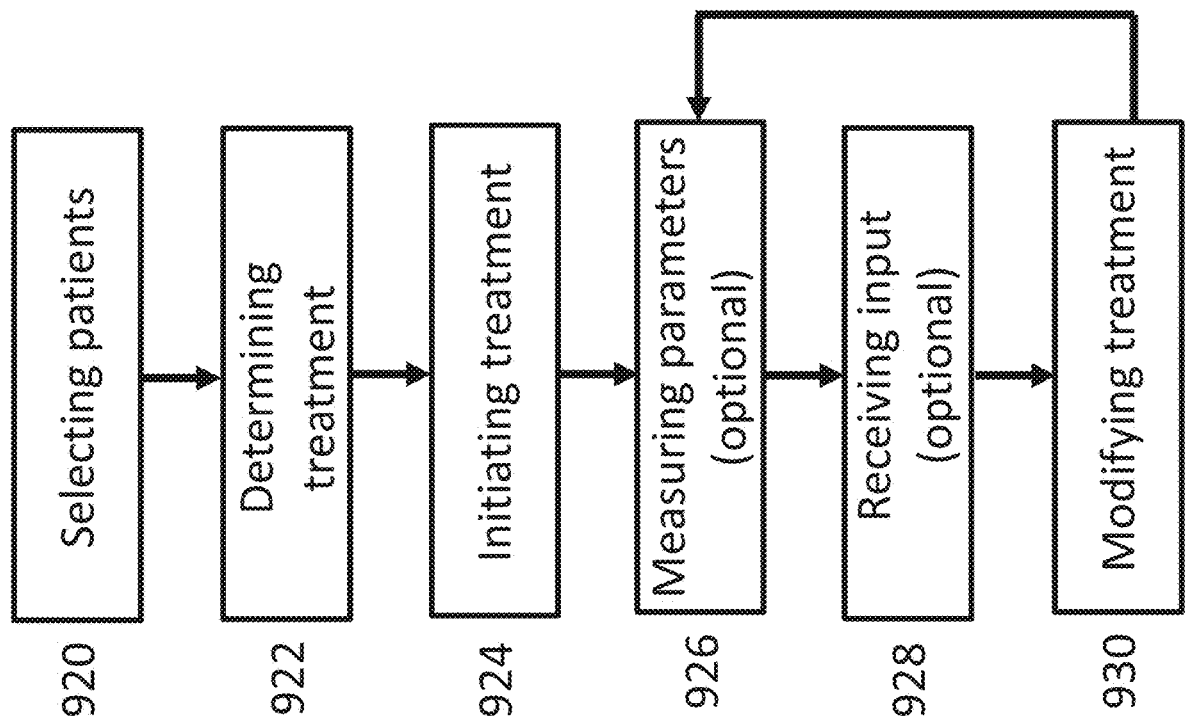
Figure 9D:
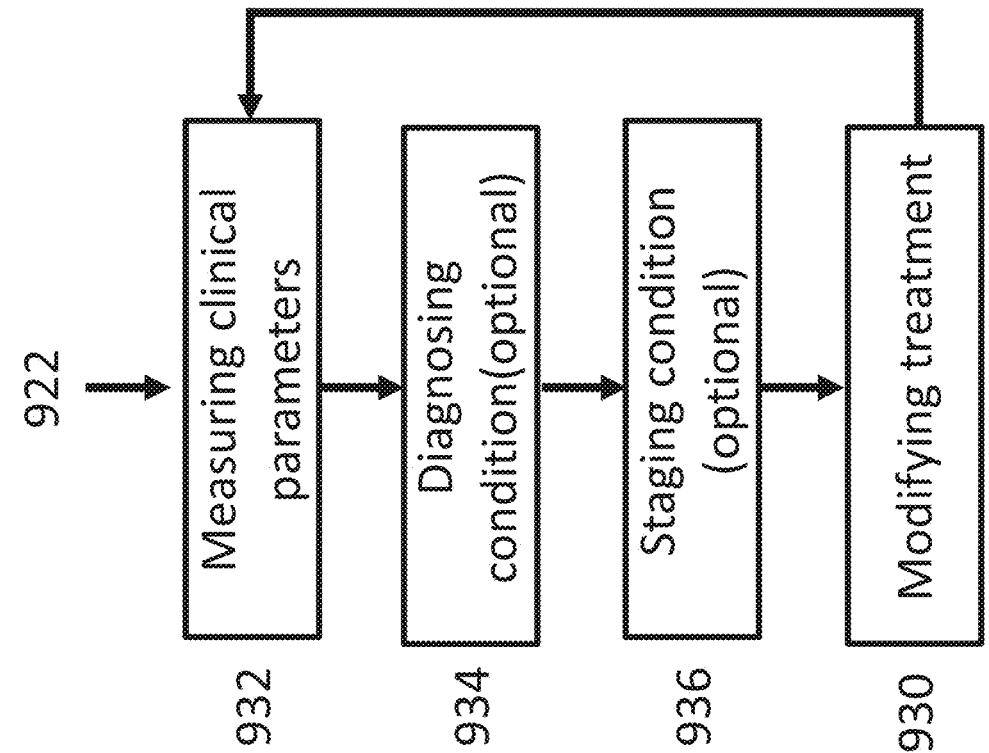
Figure 9E:
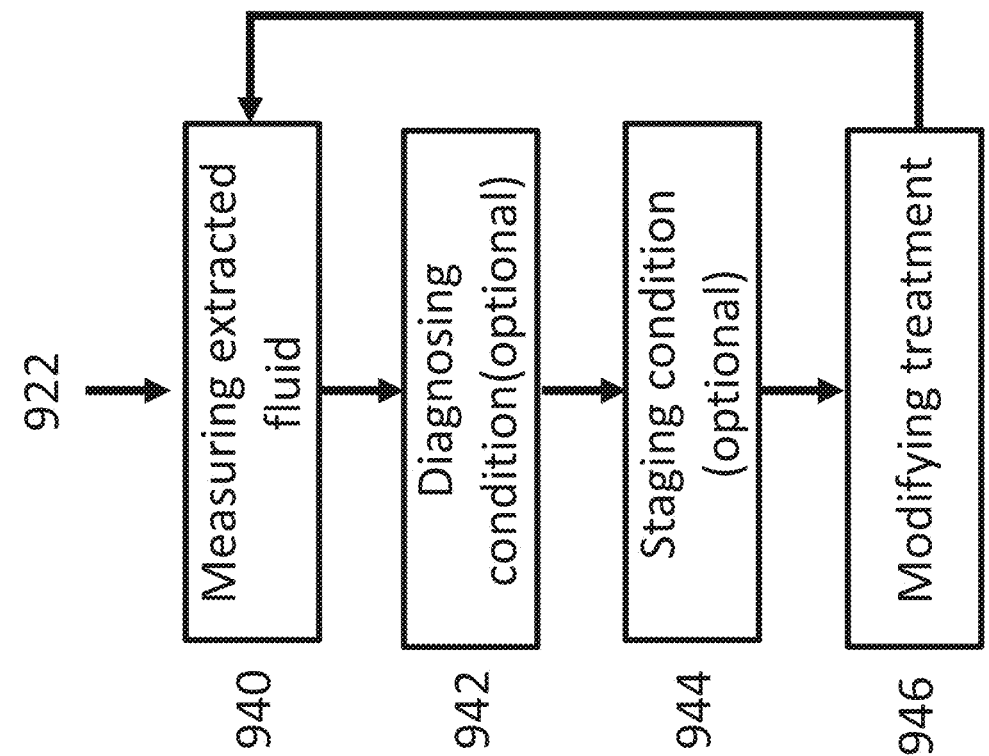
Figure 9F:
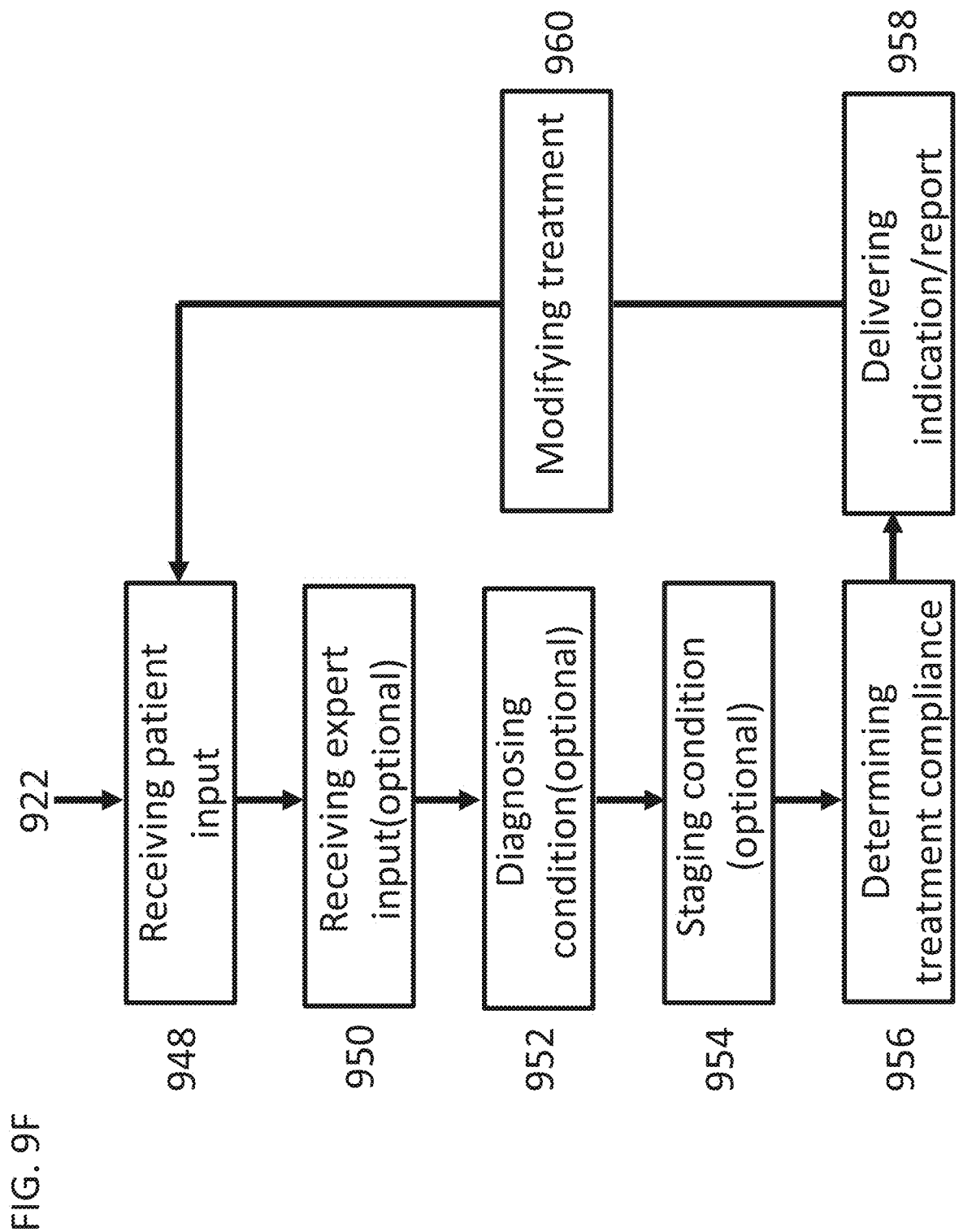
Figure 9G:
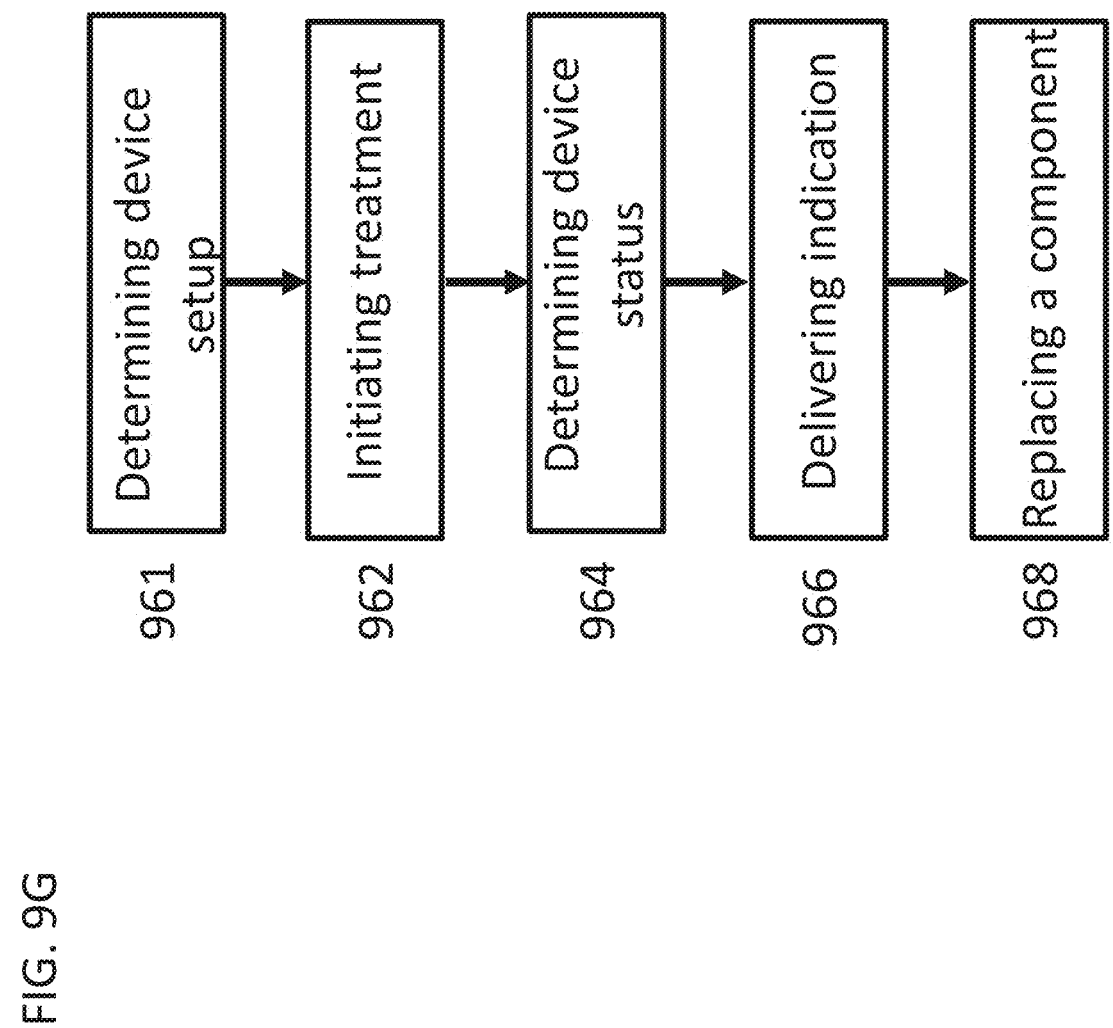
Figure 11A:
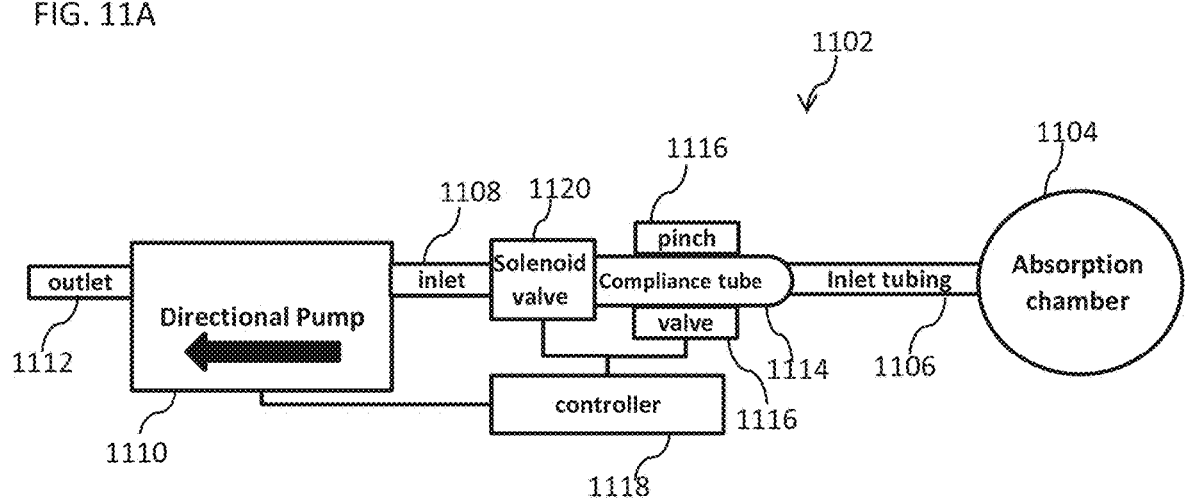
Figure 11B:
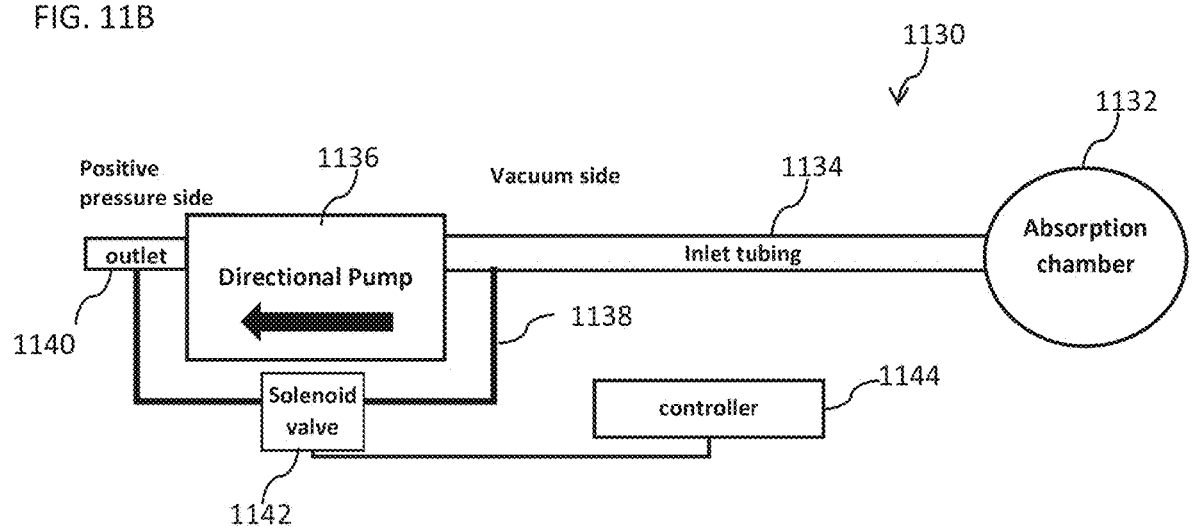
Figure 11C:
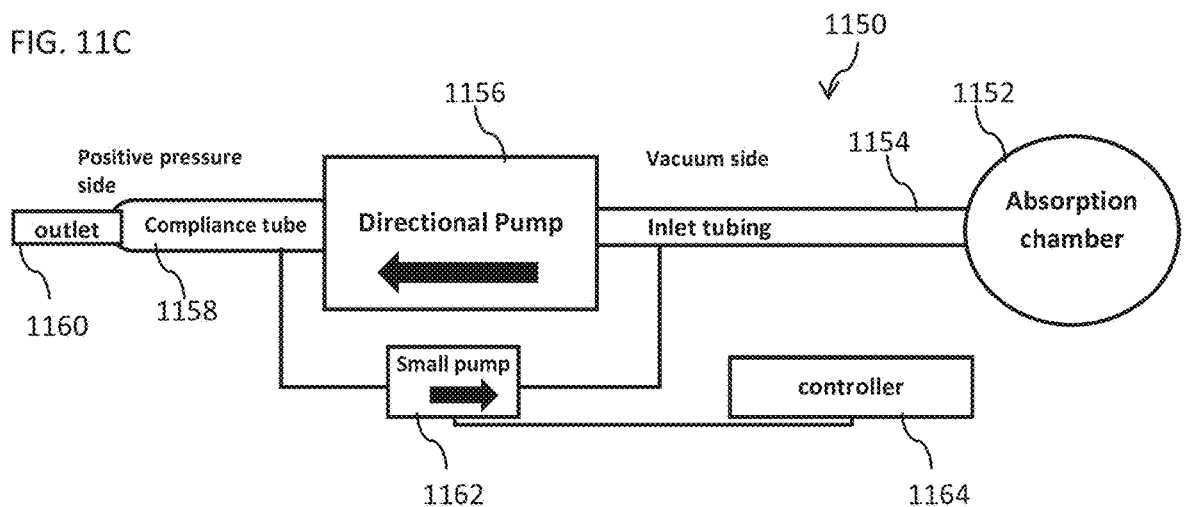
Figure 11D:
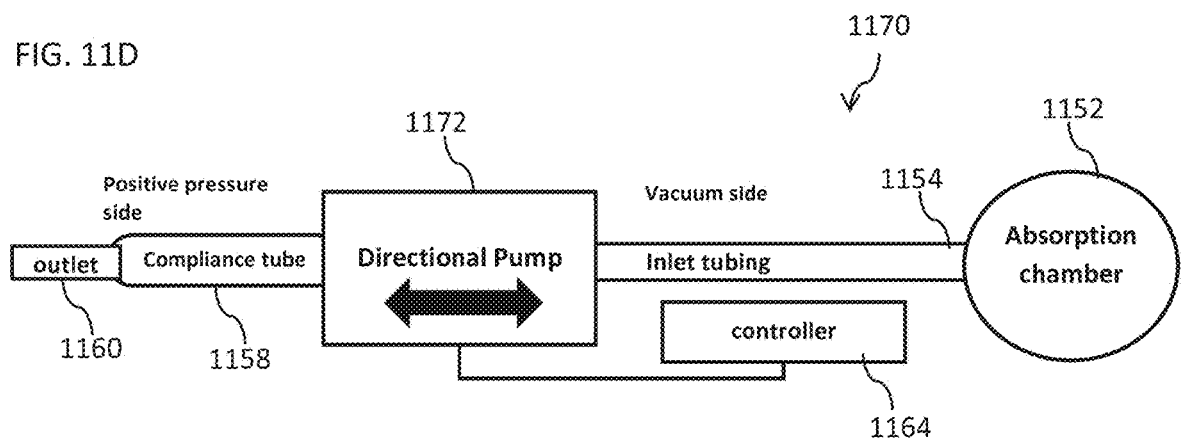
Figure 11E:
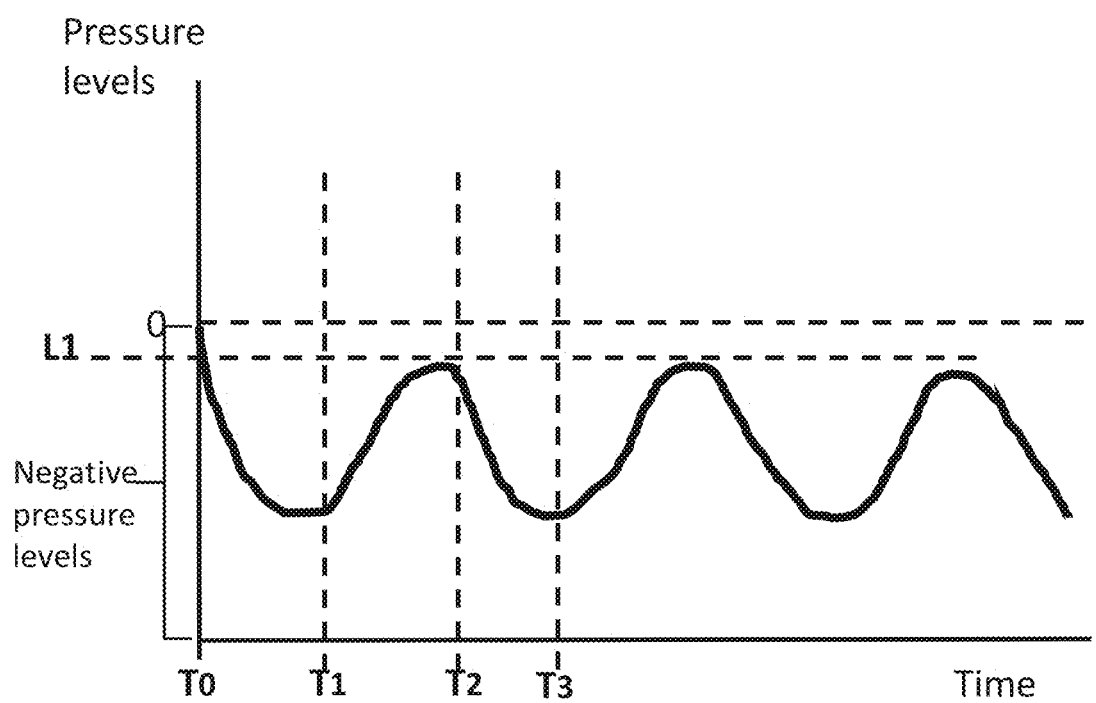
Figure 12A:
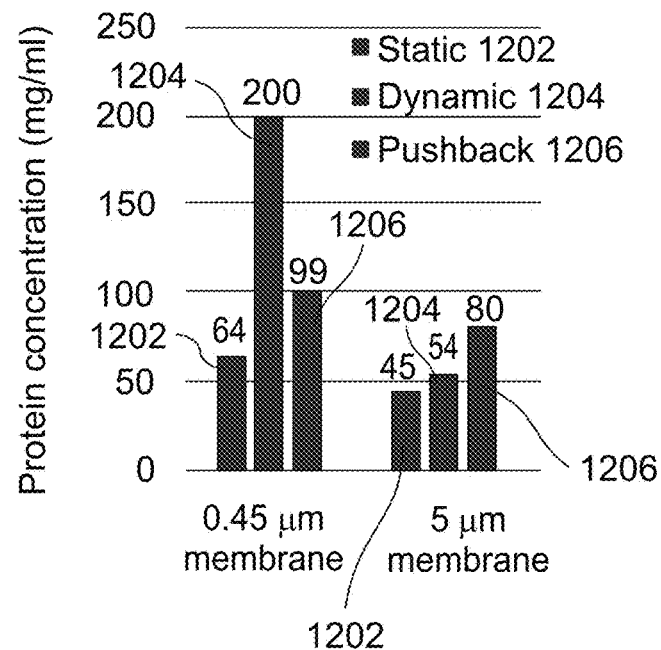
Figure 12B:
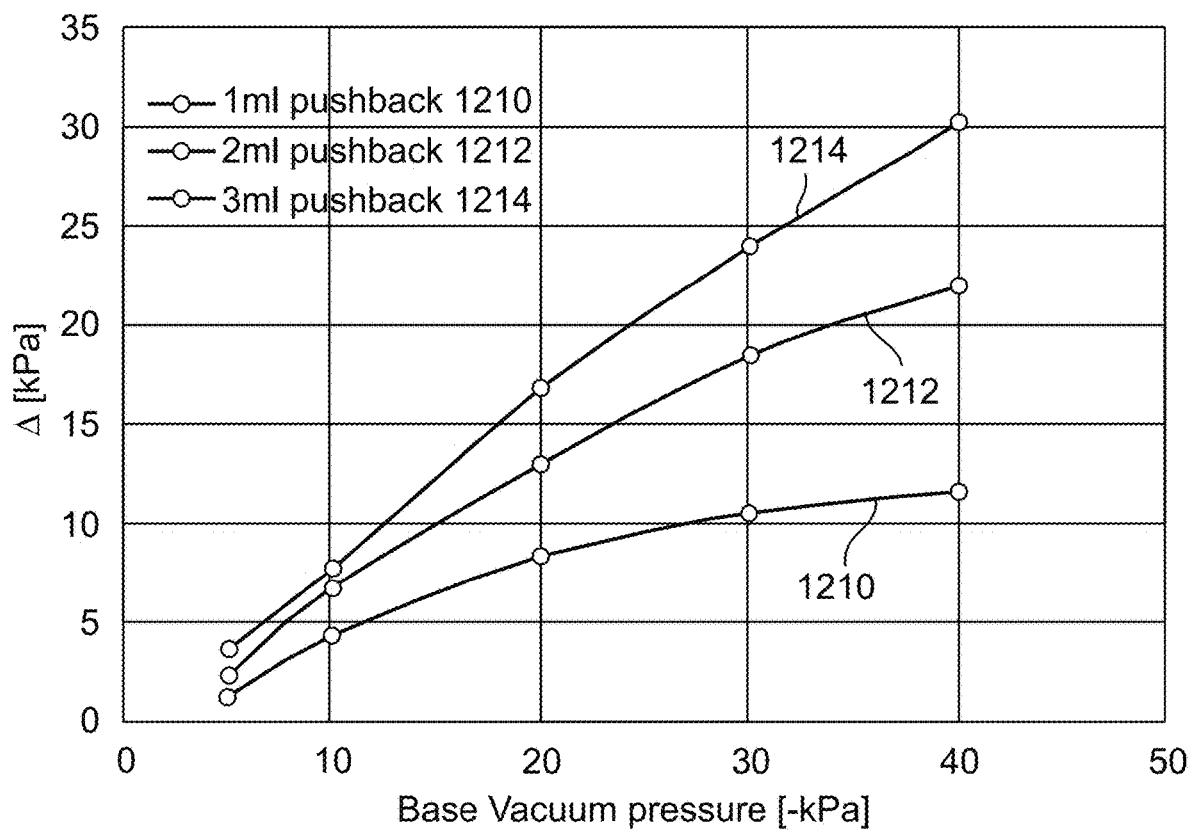
Figure 13A:
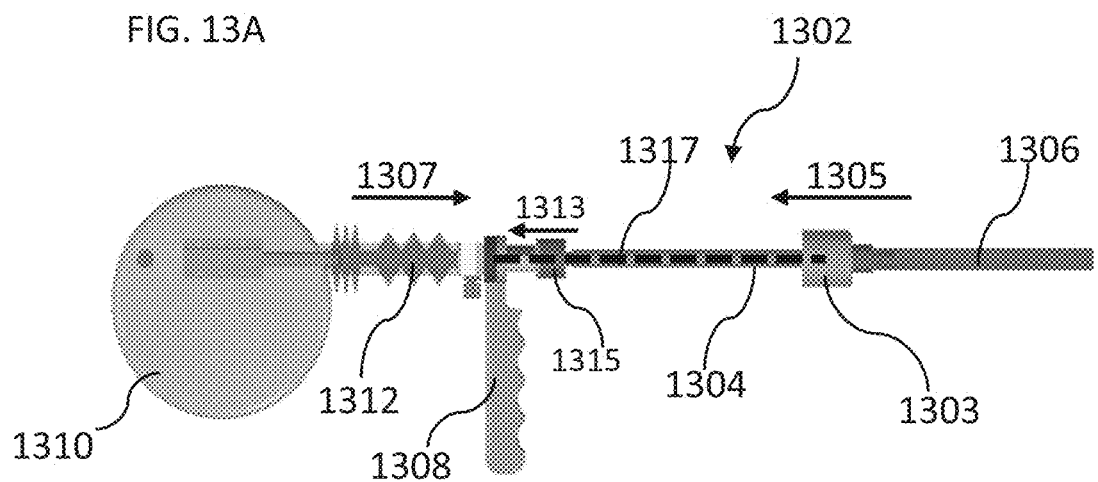
Figure 13B:
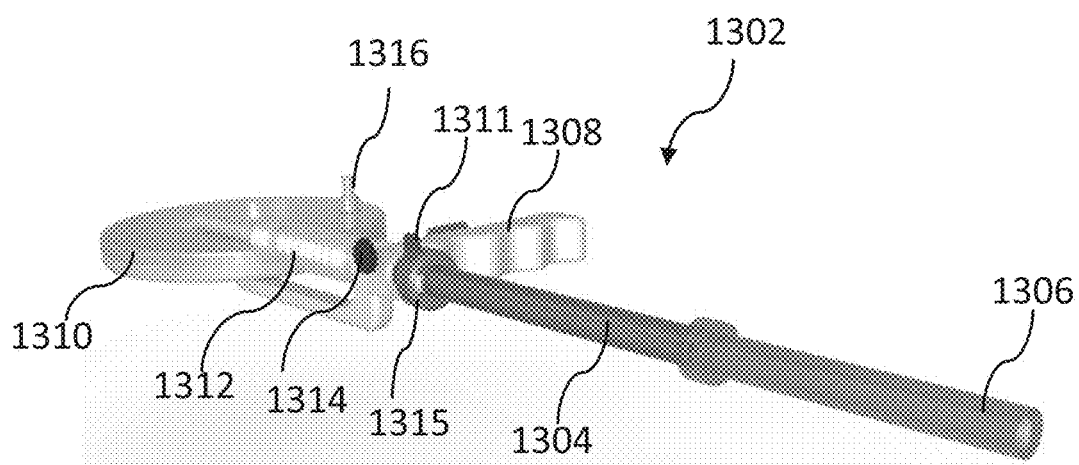
Figure 14A:
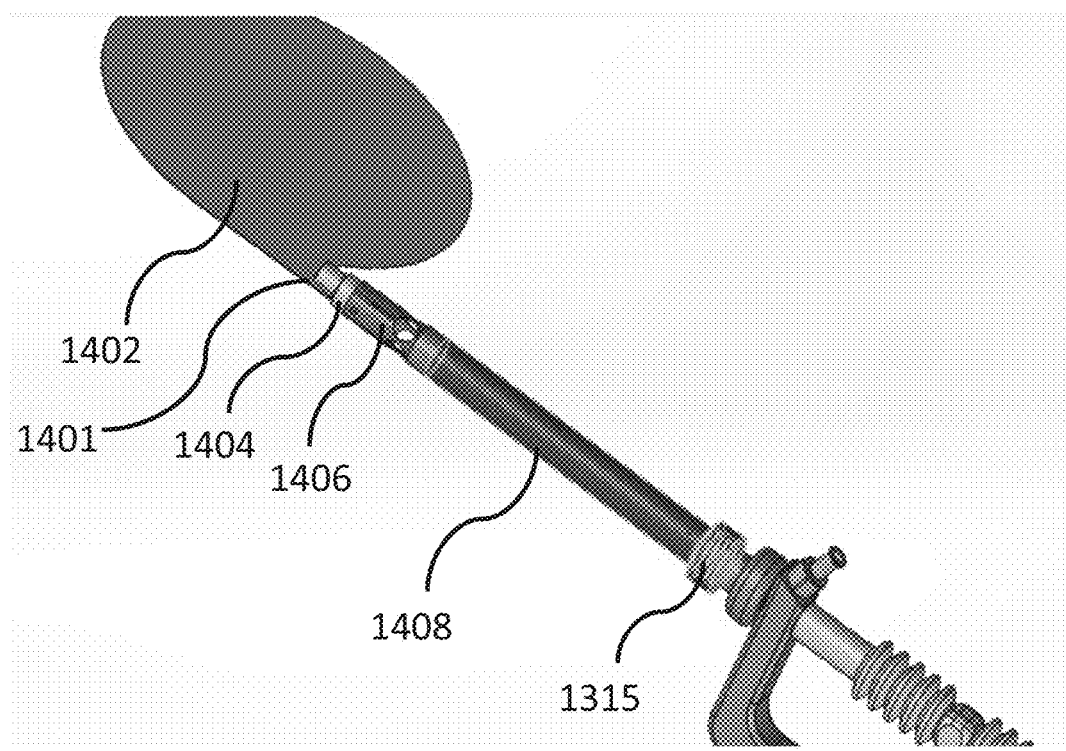
Figure 14B:
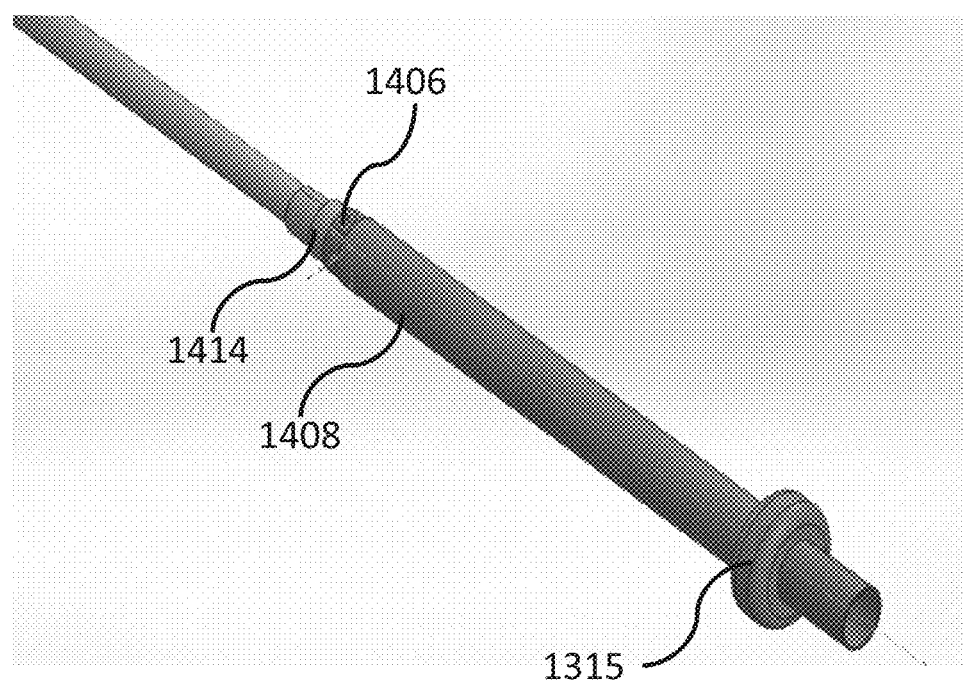
Figure 14C:
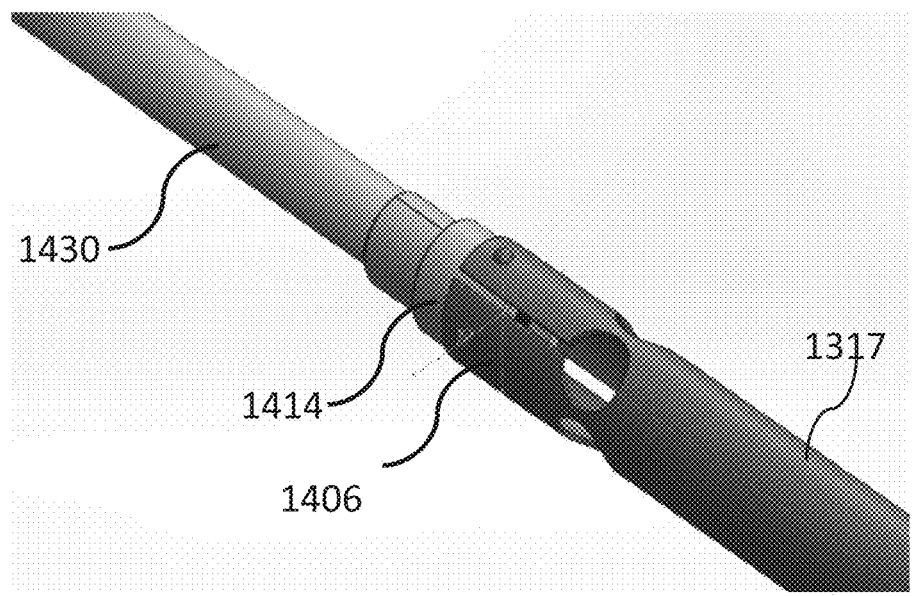
Figure 14D:
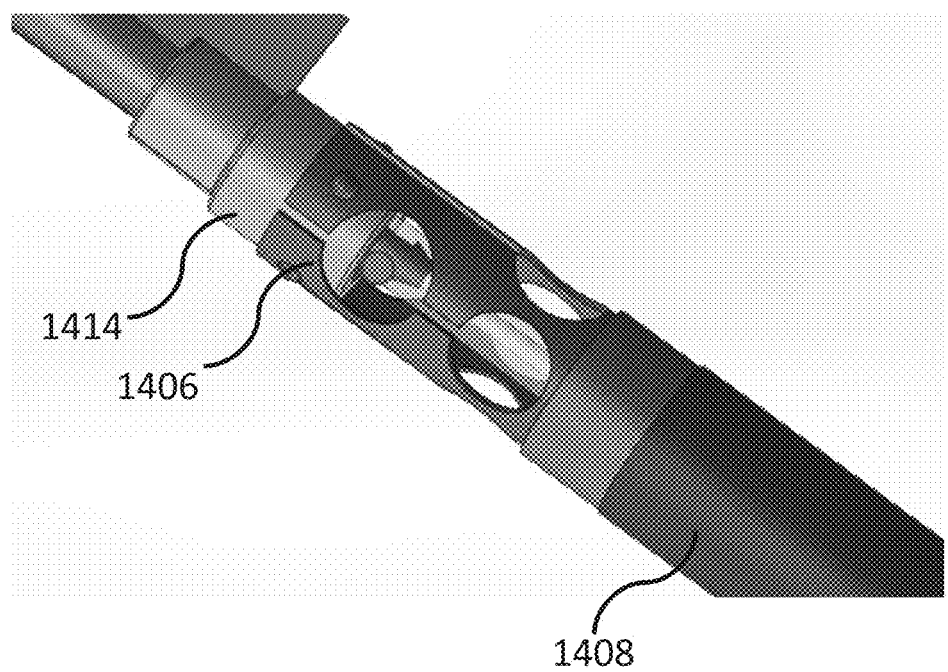
Figure 14E:
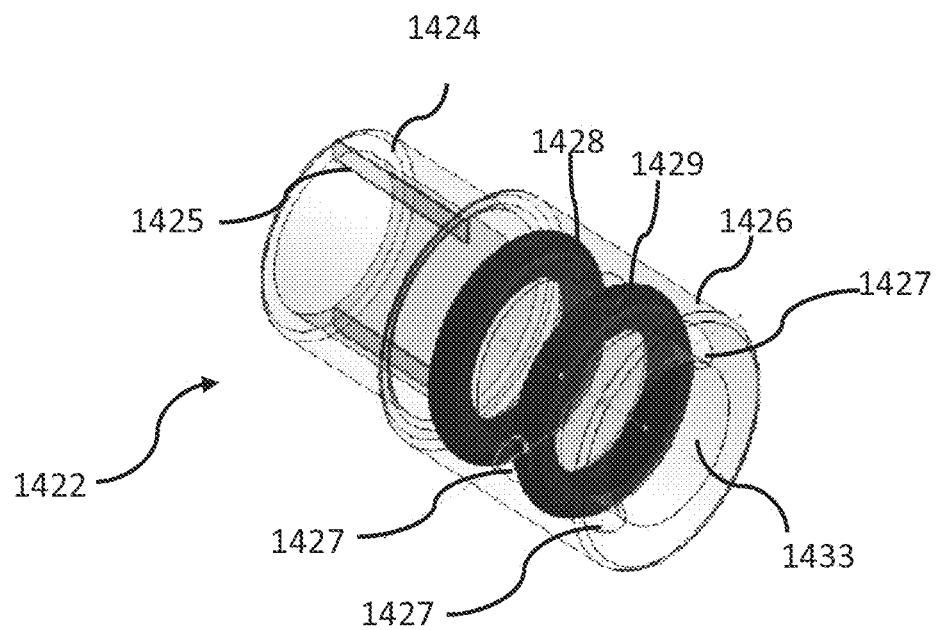
Figure 15:
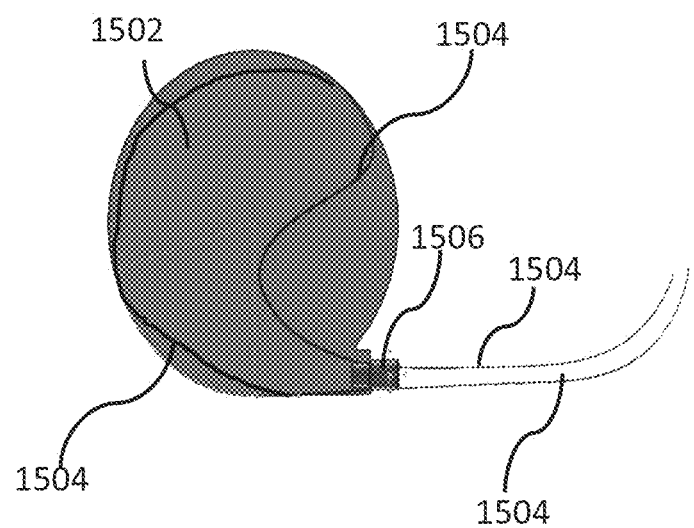

FIG. 9A is a schematic illustration of input sources affecting a fluid extraction treatment, according to some embodiments of the invention;

FIG. 9B is a schematic illustration of input types affecting a fluid extraction treatment, according to some embodiments of the invention;

FIG. 9C is a flow chart of a general process for modifying a fluid extraction treatment, according to some embodiments of the invention;

FIG. 9D is a flow chart of a process for modifying a fluid extraction treatment based on clinical parameters measurement, according to some embodiments of the invention;

FIG. 9E is a flow chart of a process for modifying a fluid extraction treatment based on measurements of the drained fluid, according to some embodiments of the invention;

FIG. 9F is a flow chart of a process for modifying a fluid extraction treatment based on input received from the patient and/or a physician, according to some embodiments of the invention;

FIG. 9G is a flow chart of a setup and/or a maintenance process of an implanted fluid extraction device, according to some embodiments of the invention;

FIGS. 10A-10H are images, tables and graphs describing the results of supporting experiments, according to some embodiments of the invention;

FIGS. 11A-11D are block diagrams of fluid extractions systems which include pressure alteration features, according to some embodiments of the invention;

FIG. 11E is a graph depicting changes in pressure applied within the absorption chamber, according to some exemplary embodiments of the invention;

FIG. 12A is a graph depicting changes in protein concentration attached to two types of membranes under different pressure conditions, according to some embodiments of the invention;

FIG. 12B is a graph showing changes in pressure from a base line pressure level in different conditions, according to some embodiments of the invention;

FIGS. 13A and 13B are schematic illustrations of an introducing system, according to some embodiments of the invention;

FIGS. 14A-14D are illustrations of an absorption chamber releasing mechanism of an introduction system, according to some embodiments of the invention;

FIG. 14E is an illustration of a port connector, according to some embodiments of the invention; and FIG. 15 is a schematic illustration of an absorption chamber having an internal expandable wire, according to some embodiments of the invention.

DESCRIPTION OF SPECIFIC EMBODIMENTS OF THE INVENTION

The present invention, in some embodiments thereof, relates to a fluid extraction system and, more particularly, but not exclusively, to an implanted fluid extraction system.

A broad aspect of some embodiments relates to adjusting a fluid extraction treatment to a clinical condition of a subject. In some embodiments, the treatment is adjusted according to a disease of a subject. Alternatively or additionally, the treatment is adjusted according to measured clinical parameters during and/or after the treatment.

An aspect of some embodiments relates to an implantable fluid extraction device or system with at least one sensor. In some embodiments, the sensor measures clinical parameters of the patient, for example temperature, blood pressure, blood content, and/or congestion level. Alternatively or additionally the sensor measures the content of the extracted and/or drained fluid. In some embodiments, at least one parameter related to the activation of the device is modified following the measurement conducted by the sensor.

An aspect of some embodiments relates to an implanted fluid extraction device or system with a memory. In some embodiments, the memory stores treatment protocols and/or activation protocols of the device. Alternatively or additionally, the memory stores values of at least one treatment parameter. In some embodiments, the device is activated based on the treatment protocols and/or the activation protocols stored in the memory. In some embodiments, the memory stores log files of the device and/or values of clinical parameters measured by the device.

An aspect of some embodiments relates to automatically modifying at least one treatment parameter during a fluid extraction treatment. In some embodiments, the at least one treatment parameter is modified based on clinical parameters measurements and/or input received from a patient during the treatment. Alternatively or additionally, the treatment is modified based on input received from a physician. In some embodiments, the treatment is automatically modified based on an output of the treatment.

In some embodiments, the at least one treatment parameter is modified based on a protocol table, or protocol settings, for example by comparing measured values of parameters to values or indication of values in the table. In some embodiments, the protocol and/or the treatment is modified based on the results of the treatment. Optionally, the table is stored in a memory of the control unit.

An aspect of some embodiments relates to an implanted permeable sack with a membrane. In some embodiments, the sack is covered at least partly with the membrane. Alternatively or additionally, the membrane is positioned inside the lumen of the sack. In some embodiments the sack and/or the membrane are porous. In some embodiments, the pores size is smaller than the size of a cell. In some embodiments the sack is a foldable sack.

In some embodiments, the sack is made from a permeable membrane. In some embodiments, the membrane is shaped as a sack. In some embodiments, part of the sack is impermeable to fluids. In some embodiments, the sack is spherical. In some embodiments, the largest dimension of the sack is smaller than 30 cm, for example 20, 15, 12 cm or any intermediate or smaller value.

In some embodiments, the sack and/or the membrane are shaped and sized to be in direct contact with a tissue, for example tissue of organs positioned inside the peritoneum. In some embodiments, the sack and/or membrane are shaped and sized to be in direct contact with part of the column or column tissue. In some embodiments, the membrane is shaped and sized to be in a direct and tight contact with the tissue, for example when high levels of negative pressure, for example vacuum, is applied through the membrane on the tissue. As used herein, a tight contact between a portion of the absorption chamber, for example a surface of an absorption chamber, a sack and/or permeable membrane with a tissue is an interaction where at least 30% of the surface area of the contacting portion is in distance of less than 150 µm. Alternatively or additionally, a tight contact between a portion of the absorption chamber, for example a surface of an absorption chamber, a sack and/or permeable membrane with a tissue is an interaction where contact facilitates a peak of inward force of at least 25N on the contacted tissue.

In some embodiments, the sack and/or membrane are flat or thin, for example the ratio between the smallest dimension and the largest dimension of the sack and/or membrane is at least 1:3, for example 1:4, 1:5 or any intermediate or larger ratio. In some embodiments, the external diameter of the sack is smaller than 25 cm, for example 20, 17, 15 cm or any intermediate or smaller value. In some embodiments, the sack comprises at least one flattened surface, shaped and sized to be in direct and optionally tight contact with the tissue.

According to some embodiments, the sack comprises at least one flat surface shaped and sized to comply, also termed herein as to conform to a shape and/or a structure of a tissue or the tissue external surface, for example to maintain tight attachment between the at least one flat surface and the tissue. In some embodiments, the at least one flat surface is placed in direct contact with a tissue and/or a tissue surface, optionally in a direct and tight contact. In some embodiments, fluid is directly extracted from the tissue into the sack through the flat surface of the sack that is tightly attached to the tissue. In some embodiments, fluid from the tissue is not extracted directly into the sack through external regions of the sack that are not attached to the tissue surface.

According to some embodiments, the sack, the membrane and/or an absorption chamber are preshaped to be flat and thin. In some embodiments, the sack, the membrane and/or an absorption chamber conform to an external shape of a tissue and/or to an anatomical contour of the tissue by having a loosness and elastic external surface.

An aspect of some embodiments relates to a permeable sack that is filled with a deployable internal scaffold. In some embodiments, the internal scaffold keeps the sack flat. In some embodiments, the internal scaffold provides mechanical strength to the sack. Alternatively or additionally, the internal scaffold drains fluids from the sack.

In some embodiments, the sack has a pre-formed shape. In some embodiments, the shape of the deployable internal scaffold is pre-formed to the shape of the sack. In some embodiments, the internal scaffold comprises a braided tube. Alternatively, the internal scaffold comprises a coiled tube. In some embodiments, the internal scaffold comprises an internal stylet, for example to keep the deployed internal scaffold flat. Optionally, the stylet has a rectangular cross section. In some embodiments, the stylet is made from a shape memory material, for example Nitinol.

In some embodiments, the sack is shaped and sized to be implanted in a body cavity, for example in the peritoneum. Alternatively, the sack is shaped and sized to be implanted subcutaneously. In some embodiments, the sack is flattened and/or thin. In some embodiments, the sack is in a direct contact with the tissue.

An aspect of some embodiments relates to a permeable sack comprising two surfaces that are connected in at least two connection points. In some embodiments, the surfaces are connected in at least two points to restrict the smallest dimension of the sack. In some embodiments, the surfaces are connected in at least two points to prevent ballooning of the sack. In some embodiments, the two connections are located at a distance of at least ⅓ of the diameter of the sack from the periphery of the sack. Alternatively or additionally, the surfaces are connected in at least two points to allow even distribution of an internal scaffold made from particles, for example beads throughout the entire lumen of the sack. In some embodiments, the at least two connection points form openings to allow fluid to pass through the sack without entering into the lumen of the sack.

In some embodiments, the sack is shaped and sized to be implanted in a body cavity, for example in the peritoneum. Alternatively, the sack is shaped and sized to be implanted subcutaneously. In some embodiments, the sack is flattened and/or thin. In some embodiments, the sack is in a direct contact with the tissue.

An aspect of some embodiments relates to deployment of a folded sack that is unfolded, structurally stabilized and is locked in a stabilized state. In some embodiments, the sack is stabilized by inserting a gel or a self-polymerizing fluid into an internal scaffold positioned inside the sack. In some embodiments, the sack is locked in a stabilized state by locking the internal scaffold relative to the sack. In some embodiments, the internal scaffold is locked to a connector positioned in the insertion site of the scaffold into the sack. In some embodiments, the internal scaffold is irreversibly locked, for example by an interference locking mechanism. Alternatively, the internal scaffold is reversibly locked, for example by rotation of the connector. Optionally, the internal scaffold is reversibly locked for device extraction purposes. In some embodiments, the movement of the internal scaffold is restricted within the sack.

In some embodiments, the sack is shaped and sized to be implanted in a body cavity, for example in the peritoneum. Alternatively, the sack is shaped and sized to be implanted subcutaneously. In some embodiments, the sack is flattened and/or thin. In some embodiments, the sack is in a direct contact with the tissue.

According to some embodiments, the folded sack is deployed and is locked in a stabilized state that allows direct and optionally tight attachment between a membrane associated with the sack, for example a membrane that forms the sack or a membrane positioned within or outside the sack, with the tissue. In some embodiments, the folded sack is deployed and locked in a stabilized state that allows direct, and optionally tight attachment between the sack and an external surface of the tissue.

An aspect of some embodiments relates to extracting fluids from a tissue by actively applying negative pressure in intervals on said tissue. In some embodiments, a pump, for example a peristaltic pump applies high levels of negative pressure followed by lower levels of negative pressure on said tissue. Optionally, the pump is operated in ON:OFF duty cycles. Optionally, the pump is activated between 10% to 98%, for example 10%, 15%, 25%, 50% or any intermediate value of the time the fluid extracting chamber is implanted in the body.

In some embodiments, the duty cycles are adjusted to the condition of the patient, and/or to the patient's activity, for example drinking, eating, sleeping periods of the patient.

An aspect of some embodiments relates to adjusting a fluid extracting treatment or a protocol of a device used in the treatment to additional treatments and/or physiological activity. In some embodiments, the fluid extraction treatment is adjusted to the kidney filtration rate and/or to bodily fluid accumulation rate. In some embodiments, a fluid extracting system actively applies a reduced vacuum force to efficiently extract fluids from the tissue. In some embodiments, a fluid extraction system applied a reduced drainage protocol timing to efficiently extract fluids from the tissue. In some embodiments, the device applies a reduced vacuum force and/or a reduce drainage protocol timing when the efficiency of the kidney filtration is elevated. In some embodiments, the protocol or the treatment is adjusted to reach required relative drainage rate of 0.01% to 0.05% body weight per hour (0.24% to 1.2%/day).

In some embodiments, a protocol of at least one of additional treatment is modified. In some embodiments, the protocol or a portion thereof of the additional treatment is modified based on an output measured by the device.

An aspect of some embodiments relates to applying positive pressure on a fluid extraction chamber to remove unwanted substances attached to the chamber. It should be noted that when applying positive pressure, the total pressure applied on the tissue or on the fluid extraction chamber remains negative. In some embodiments, a positive pressure is applied to remove proteins, tissue and/or cells attached to the fluid extraction chamber. In some embodiments, the positive pressure is applied to remove proteins, tissue and/or cells attached to a membrane of the fluid extraction chamber. In some embodiments, the positive pressure is applied as short transient bursts of positive pressure, for example by reversing existing vacuum closer to neutral pressure or above native tissues interstitial pressure (0-20 mmHg) for short period of 0.1-10 seconds. Optionally, the changes in pressure are gradual and/or slower. In some embodiments, the positive pressure is applied together with a negative pressure applied, for example by a vacuum pump, to reach a total negative pressure. In some embodiments, when the total pressure on the tissue is negative, the membrane remains attached to the tissue. Alternatively, if the total pressure is a positive pressure, the membrane separates, at least partly, from the tissue. In some embodiments, the total pressure is zero. In some embodiments, when the total pressure is zero or positive, the membrane moves to a different location, for example to be placed in contact with a different tissue region or with a different tissue.

According to some embodiments, application of up and down levels of negative pressure on a draining tube connected to a fluid extraction chamber is used to mechanically vibrate a membrane associated with the chamber, for example a membrane which contacts the tissue.

According to some embodiments, the positive pressure is applied by a pump, for example a peristaltic pump connected to the chamber. In some embodiments, the pump is connected to an outlet of the chamber, or to a draining tube connected to the outlet. In some embodiments, the positive pressure is applied by the pump on the draining tube connected to the chamber. In some embodiments, the pump is rotated in a first direction to apply a negative pressure on the chamber and in a second direction to apply a positive pressure on the chamber. In some embodiments, the rotation direction of the pump is reversed to shift between the first direction and the second direction.

According to some embodiments, at least one valve is positioned on a fluid flow path connecting a pump configured to apply negative pressure, and the chamber. In some embodiments, the at least one valve, for example a solenoid valve and/or a pinch valve is activated, for example opened and closed to generate shunts and/or pressure changes within the fluid flow path and the chamber. In some embodiments, the at least one valve is opened and closed in time periods of up to 1 second, for example 0.13 second, 0.5 second, 0.8 second or any intermediate, smaller or larger time period.

According to some embodiments, the pressure changes are applied by activation of a second pump positioned on the fluid flow path, configured to generate the relative positive pressure step.

In some embodiments, the activation of the at least one valve and/or the activation of a pump to generate a positive pressure is controlled by a controller of the system. Optionally, the activation of the at least one valve or the pump is controlled by the controller according to signals delivered from a sensor, for example a pressure sensor configured to sense pressure changes in the fluid flow path exiting from the chamber and/or pressure changes within chamber.

According to some exemplary embodiments, in subjects suffering from the following conditions: (1) Left sided heart failure and underlying chronic kidney disease, (2) Right sided heart failure, excluding ascites conditions, (3) Bi-ventricular heart failure, (4) Fontan failure, (5) Pulmonary hypertension with systemic congestion, the fluid extraction treatment using the system and methods described herein is adjusted to extract fluid in a range of 150-500 ml/day.

According to some exemplary embodiments, in subjects suffering from the following conditions: (1) Chronic Kidney Disease in stages 4 and 5, (2) End stage renal disease, (3) Abdominal compartment syndrome, (4) Ascites conditions, related to cirrhosis, portal hypertension etc., the fluid extraction treatment using the system and methods described herein is adjusted to extract fluid in a range of 500-1000 ml/day.

Potential advantages of using the implantable system in one or more embodiments describe herein are that the system is fully implantable and optionally drains fluids to the urinary system. Additional optional advantages in one or more of the described embodiments is that the system has no circulation contact and optionally it has a configurable operation. In some embodiments, the system uses a direct mechanism for extracting fluids directly from the tissue. In addition, in one or more of the embodiments described herein the system applies pressure on the tissue in intervals and not continuously.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Implanted System

Figure 1:
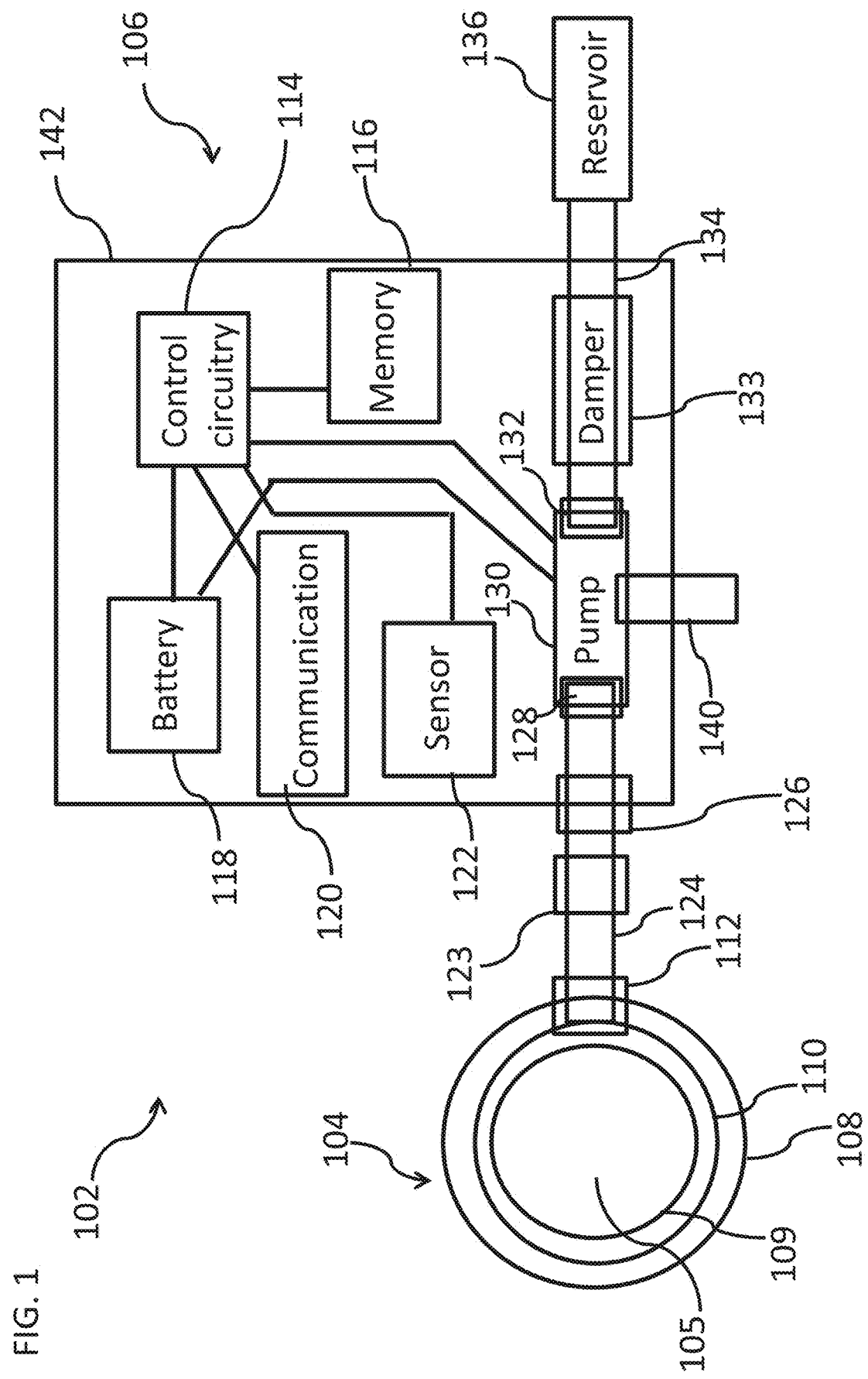

According to some exemplary embodiments, a device for draining fluid is implanted into a cavity of the body, for example into the peritoneal cavity. Reference is now made to FIG. 1, depicting an implantable device or an implantable system, according to some embodiments of the invention.

According to some exemplary embodiments, an implantable system, for example system 102 comprises a fluid extraction chamber, for example fluid absorbing unit 104, which is shaped and sized to positioned inside a body cavity, for example the peritoneal cavity or to be implanted subcutaneously. In some embodiments, the absorbing unit 104 has at least one flat side for contacting a tissue. In some embodiments, the fluid extraction chamber, for example fluid absorbing unit is flattened and/or thin and/or curved and/or dome-shaped. In some embodiments, the fluid extraction chamber in some embodiments, the absorbing unit 104 comprises an inner lumen 105 and an outer flat layer 108, surrounding the inner lumen 105. In some embodiments, the outer flat layer 108 is a membrane, optionally a porous membrane. In some embodiments, the outer flat layer 108 is shaped and sized to contact at least partly a tissue. In some embodiments, when contacting the tissue, fluids from the tissue pass directly through the outer flat layer 108 into the inner lumen 105 of the absorbing unit 104. Optionally, the outer flat layer has a large surface area which is sufficient to directly absorb fluid from the tissue. In some embodiments, the fluids pass is passive due to pressure differences between the tissue and the inner lumen 105, for example when the pressure in the tissue is higher than the pressure inside the inner lumen 105. Alternatively, the fluids actively pass from the tissue into the inner lumen when a pump is activated.

According to some exemplary embodiments, the outer flat layer 108 is a porous layer which optionally forms a sack. In some embodiments, an inner membrane, for example inner membrane 110 is positioned inside the sack within inner lumen 105. In some embodiments, the inner membrane 110 is shaped and sized to absorb fluids passing directly from the tissue through the outer flat layer 108 into the fluid absorbing unit 104.

According to some exemplary embodiments, the fluid absorbing unit 104 comprises an inner scaffold 109, which is optionally rigid or semi-rigid. In some embodiments, the inner skeleton 109 stabilizes and prevents the collapse of the outer flat layer. In some embodiments, the inner scaffold is shaped and sized to be deployed and/or removed from the inner lumen 105. In some embodiments, the inner membrane 110 is attached to the inner scaffold 109 when the inner scaffold 109 is deployed or removed, for example to allow the removal and replacement of the membrane.

According to some exemplary embodiments, the fluid absorbing unit 104 comprises at least one connector, for example connector 112 for connecting a draining tube, for example an outlet tube 124, to the fluid absorbing unit. In some embodiments, the outlet tube 124 is pushed into the lumen 105, and is optionally part of the inner scaffold 109. In some embodiments, the fluids drained from the tissue into the fluid absorbing unit are removed through the outlet tube 124.

According to some exemplary embodiments, system 102 comprises an implantable control unit, for example control unit 106. In some embodiments, the control unit 106 comprises a pump 130, for example a peristaltic pump which is connected to the outlet tube 124 via connector 128. In some embodiments, the pump 130 is connected to control circuitry 114 of the control unit 106. In some embodiments, the control circuitry 114 activates the pump 130 to remove absorbed fluids from the fluid absorbing unit 104. Alternatively or additionally, the control circuitry 114 activates the pump 130 for example, to generate sufficient pressure, optionally negative pressure, to allow extraction of fluids from the tissue into the absorbing unit 104. Alternatively or additionally, the pump 130 generates a positive pressure on the fluid absorbing unit 104, for example to remove materials accumulated or attached on the external surface of the fluid absorbing unit 104. In some embodiments, the pump 130 generates positive pressure on the fluid absorbing unit to remove materials, for example tissue form an external membrane layer positioned in the outer surface of the fluid absorbing unit 104. In some embodiments, prior the application of positive pressure, the system 103 closes an internal reservoir, for example reservoir 136 and optionally seals a catheter connecting from the fluid absorbing unit 104 to the urinary system. In some embodiments, the reservoir contains at least some amount of extracted fluids when it is closed.

According to some exemplary embodiments, the pump 130 is mechanically connected to the outlet tube 124, and applies the negative pressure and/or positive pressure on the outlet tube 124. In some embodiments, the control unit 106 controls the generation of up and down levels of negative pressure on the draining tube, optionally according to a protocol, for example a protocol stored in memory 116. In some embodiments, the applied up and down levels of negative pressure are used to mechanically vibrate the absorbing unit 104, and/or outer flat layer 108, for example to remove proteins, tissue and/or cells attached to the absorbing unit 104, and/or outer flat layer 108.

According to some exemplary embodiments, the pump 130 is connected to a reservoir 136, for example an internal reservoir or an external reservoir by tube 134. Alternatively or additionally, the pump 130 is connected, for example by a catheter 140 to the urinary system, for example to the urine bladder or to the renal pelvis. In some embodiments, absorbed fluids from the fluid absorbing unit 104 are drained via the control unit 106 into the reservoir, for example an implantable or extracorporeal reservoir and/or to the urine bladder. In some embodiments, the pump 130 is activated to actively remove the absorbed fluid from the fluid absorbing unit 104 into the reservoir 136 and/or into the urinary system.

According to some exemplary embodiments, control unit 106 comprises at least one sensor, for example sensors 122. In some embodiments, sensors 122 are fluid flow sensors, which sense the fluid flow from the tissue into the fluid absorbing unit 104 and/or the fluid flow from the fluid absorbing unit 104 into the control unit 106. In some embodiments, the sensors 122 sense the fluid flow from the control unit through catheter 140 or tube 134. Optionally, the sensors 122 sense the fluid flow through the pump 130. In some embodiments, the sensors 122 comprise fluid pressure sensors which sense the pressure in the fluid flow path from the tissue into the fluid absorbing unit 104 and/or the pressure in the fluid flow path from the fluid absorbing unit 104 into the control unit 106. Optionally, the sensors 122 senses the pressure in the fluid flow path associated with the pump 130, before and/or after the pump 130.

According to some exemplary embodiments, sensors 122 are a clinical sensors which sense at least one clinical parameter related to the patient, for example blood pressure, interstitial pressure, levels of substances in the blood and/or in the urine, heart rate, body temperature or any other clinical or physiological parameter related to the patient. In some embodiments, sensors 122 measure at least one parameter related to the content of the drained fluid and/or urine and/or blood, for example levels and/or concentration of chemical or biological molecules, for example electrolytes, Creatinine, Urea, Albumin and/or synthetic pharmaceutical drugs administered to the patient for the treatment of a patient condition.

According to some exemplary embodiments, the sensors 122 deliver values of the sensed parameters to control circuitry 114. In some embodiments, the sensed data is retrieved from independent implantable or external device in communication with control circuitry 114. In some embodiments, the control circuitry 114 stores at least some of the values in memory 116 of the control unit 106. In some embodiments, memory 116 stores log files of the control unit 106 and/or of the fluid absorbing unit 104. In some embodiments, memory 116 stores at least one treatment protocol and/or values of at least one treatment parameter. Optionally, the at least one treatment protocol or treatment parameter is related to the activation of the pump 130, for example activation duration, number of intervals and intervals duration between activation sessions of the pump 130 and/or the pumping power of the pump 130.

According to some exemplary embodiments, the control unit 106 comprises communication 120. In some embodiments, communication 120 is connected to control circuitry 114 and comprises a wireless receiver and/or a wireless transmitter. In some embodiments, communication 120 receives information from at least one external device or an external circuitry located outside the body, for example a sensor, a computer, an external memory, a handheld device and/or a remote control. Alternatively or additionally, the communication 120 receives information from an implantable device located within the body, for example a cardiac pacemaker and/or an implantable sensor. In some embodiments, the communication 120 delivers the received information to the control circuitry 114.

According to some exemplary embodiments, the control circuitry 114 signals the communication 120 to transmit information to a device or a circuitry located outside of the body, for example a sensor, a computer, an external memory, a handheld device and/or a remote control. In some embodiments, the control circuitry 114 signals the communication 120 to transmit information to an external interface, for example a user interface located outside of the body. In some embodiments, the control circuitry signals the external interface to generate alerts or indications associated with the treatment and/or activation of the implanted system and/or measured clinical parameters. Alternatively or additionally, the communication transmits information to an implantable device located within the body, for example a cardiac pacemaker and/or an implantable sensor.

According to some exemplary embodiments, the control unit 106 comprises at least one battery 118 for providing electric power to the control unit 106 components, for example pump 130. In some embodiments, the battery 118 is a rechargeable battery, or is a replaceable battery.

According to some exemplary embodiments, housing 142 of control unit 106 is made from a biocompatible material and is optionally shaped and sized to be implanted subcutaneous. In some embodiments, the housing 142 is positioned in a way that allows replacing specific elements of the control unit 106, for example to replace battery 118 and/or pump 130. In some embodiments, housing 142 is flat, for example to allow subcutaneous implantation.

According to some exemplary embodiments, a cuff 123, at least partly encircles outlet 124. In some embodiments, the cuff 123 is positioned between the control unit 106, which is positioned outside the peritoneum and the fluid absorbing unit 104 which is implanted inside the peritoneum. Alternatively, the fluid absorbing unit is implanted outside of the peritoneum, for example implanted subcutaneously. In some embodiments, the cuff 123 is shaped and sized to be placed in the peritoneum opening that was opened during the insertion of the fluid absorbing unit 104 into the peritoneal cavity.

According to some exemplary embodiments, a damper 133 is in contact with tube 134 and/or with pump 130. In some embodiments, the damper 133 attenuates the pump vibrations and/or the pulsatile fluid flow through the tube 134. Optionally, the damper attenuates the pulsatile fluid flow through tube 134 and/or the vibrations of pump 130 to allow measurements of the fluid flow and/or the fluid content by sensors 122.

According to some exemplary embodiments, the control circuitry is connected to a timing circuitry which signals the pump to activate in fixed duty cycles. In some embodiments, the control circuitry signals the pump to work intermittently in a fixed timing routine. Optionally, when a timing circuitry is present a memory is absent.

Exemplary System Interactions

Figure 2A:
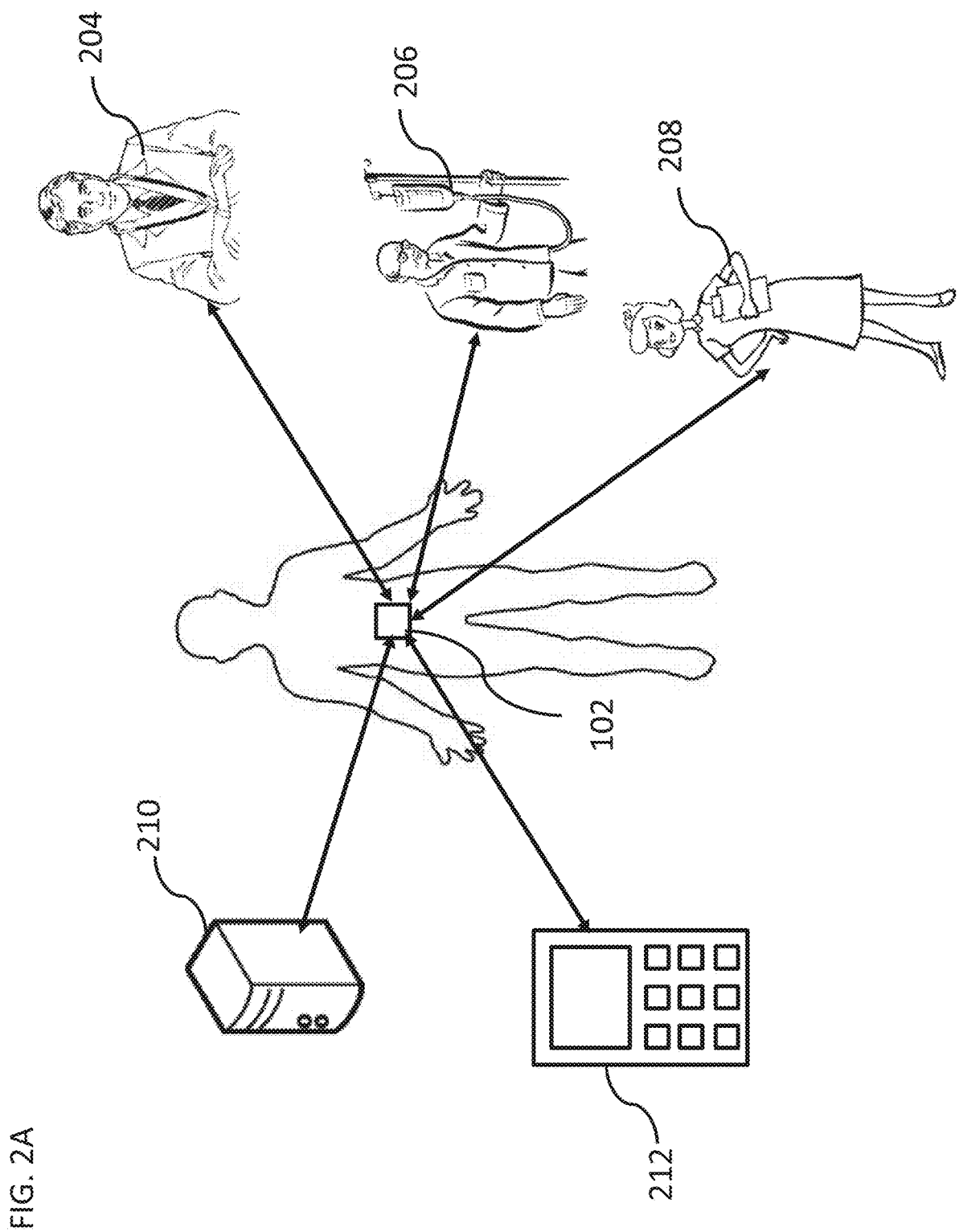

According to some exemplary embodiments, the implanted system, for example implanted system 102 is part of a system that is used to control and/or monitor fluid draining from tissue inside the body. Reference is now made to FIG. 2A, depicting interactions of a system for draining fluid from a bodily tissue with, according to some embodiments of the invention.

According to some exemplary embodiments, an implanted system 102 is connected, optionally by wireless connection to devices located outside the body. In some embodiments, the system 102 is connected to an expert or a physician 204. In some embodiments, the device transmits indications and/or alerts to a physician, for example when the system 102 is not working properly and/or when at least one outcome of the fluid draining treatment is not a desired outcome. In some embodiments, the system 102 transmits treatment reports and/or device log files to the physician 204 according to a selected schedule and/or upon request.

According to some exemplary embodiments, the system 102 delivers an indication to the physician 204 if the clinical condition of the patient changes, for example when clinical parameters values measured by the device are not in a desired range of values. In some embodiments, the physician delivers an updated treatment protocol to the device or modifies at least one existing treatment protocol or a treatment parameter stored in the memory of the system 102.

According to some exemplary embodiments, the implanted system 102 delivers indications and/or alerts to the patient 206. In some embodiments, the system 102 delivers indications and/or alerts if the device is not working properly and/or when clinical parameters measured by the device are not within a desired range of values.

According to some exemplary embodiments, the system 102 transmits indications and/or alerts to a caregiver, for example nurse 208. In some embodiments, the system 102 transmits indication to the nurse 208, when the device is not working properly and/or when a component of the device needs to be replaced, for example when an external bag used to collect the drained fluids is full and should be replaced. In some embodiments, the system 102 transmits an alert to the nurse 208 with a request to visit the patient.

According to some exemplary embodiments, the system 102 transmits indications to a handheld device, for example handheld device 212. In some embodiments, the handheld device 212 generates a human detectable indication, for example an audio indication and/or a visual indication. In some embodiments, the handheld device 212 delivers the human detectable indication to the patient 206, and/or to the physician 204 and/or to the nurse 208. In some embodiments, the handheld device 212 is used to transmit information to the system 102, using any input element of the handheld device 212.

According to some exemplary embodiments, the system 102 transmits information, for example clinical parameter values and/or log files of the device to a remote server 210 or a remote computer. In some embodiments, the system 102 downloads information, for example modified treatment protocols and/or suggested treatments from server 210.

Exemplary Fluid Flow Between Compartments

Figure 2B:
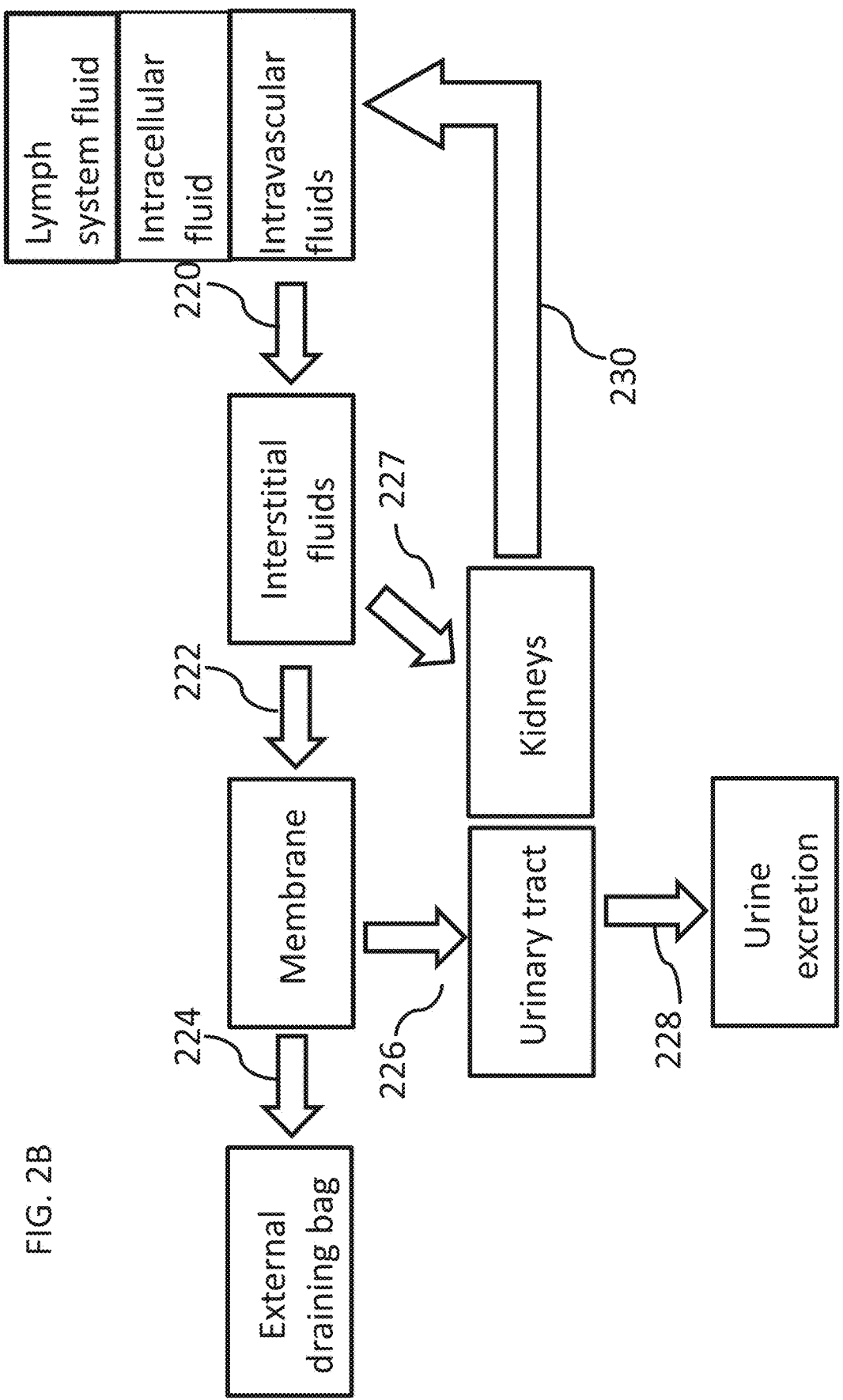

According to some exemplary embodiments, fluids flow between different biological compartments in the body. Reference is now made to FIG. 2B depicting fluid flow between biological compartments in the body, and between biological compartments and an implanted fluid extraction chamber, according to some embodiments of the invention.

According to some exemplary embodiments, fluids from the lymph system and/or intracellular fluids and/or intravascular fluids enter the interstitial space at 220. In some embodiments, a membrane, for example a membrane of the fluid absorbing unit 104 is in direct contact with the tissue to allow fluids to pass from the tissue into the fluid absorbing unit 104. In some embodiments, fluids from the tissue enter the fluid absorbing unit 104 passively or actively, for example when a pump connected to the fluid absorbing unit 104 is activated. Additionally, fluids from the interstitial space flow into the kidneys at 227 and optionally reabsorbed at 230.

According to some exemplary embodiments, fluids from the fluid absorbing unit 104 are transferred, for example via a catheter to the urinary tract, for example to the urinary bladder at 226. Alternatively or additionally, fluids from the fluid absorbing unit 104 are transferred to a draining bag at 224, for example by a catheter. In some embodiments, the draining bag is located outside the body.

According to some exemplary embodiments, fluids from the urinary tract are excreted from the body in the urine at 228.

Exemplary Fluid Absorbing Unit

According to some exemplary embodiments, in order to allow an efficient fluid extraction directly from a tissue, the tissue needs to be in a close contact with a membrane of a fluid absorbing unit, for example a fluid extraction chamber. In some embodiments, the fluid extraction chamber maintains a semi-rigid structure that applies force on part of the tissue surface, for example to reshape the tissue surface to fit the external surface of the fluid extraction chamber. Reference is now made to FIGS. 3A-3N depicting a fluid absorbing unit, for example a fluid extraction chamber, according to some embodiments of the invention.

According to some exemplary embodiments, for example as shown in FIG. 3A, a fluid absorbing unit 300, for example a fluid extraction chamber, comprises a sack, for example sack 306 and a tube 314 that is connected to the sack 306 via a port 310, which is placed in an opening of the sack 306. In some embodiments, a membrane is placed on the outer surface of the sack 306. Alternatively, the membrane is placed inside the sack 306.

According to some exemplary embodiments, an internal scaffold, for example a spiral coil 312 is positioned within the sack 306. In some embodiments, the internal scaffold applies force on the inner surface of the sack 306, for example to maintain a semi-rigid structure of the fluid absorbing unit 300. In some embodiments, the semi-rigid structure of the sack 306, allows for example to reshape the outer surface of a tissue when the outer surface of the sack contacts the tissue. In some embodiments, the outer surface of the tissue is reshaped to fit the external surface of the sack 306.

According to some exemplary embodiments, a cuff 320 surrounds at least partly the tube 314, and is positioned in a peritoneum access opening.

Figure 3B:
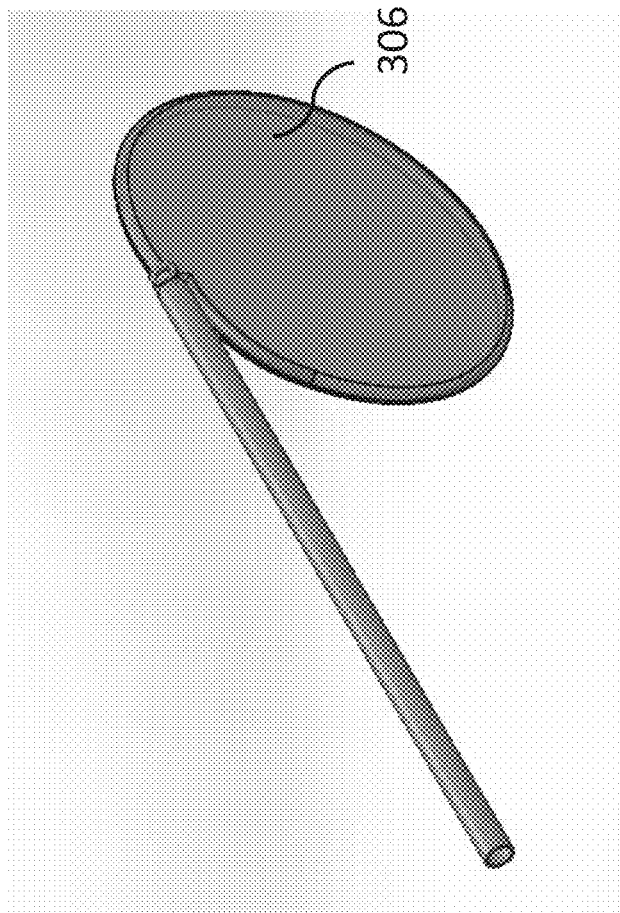
Figure 3C:
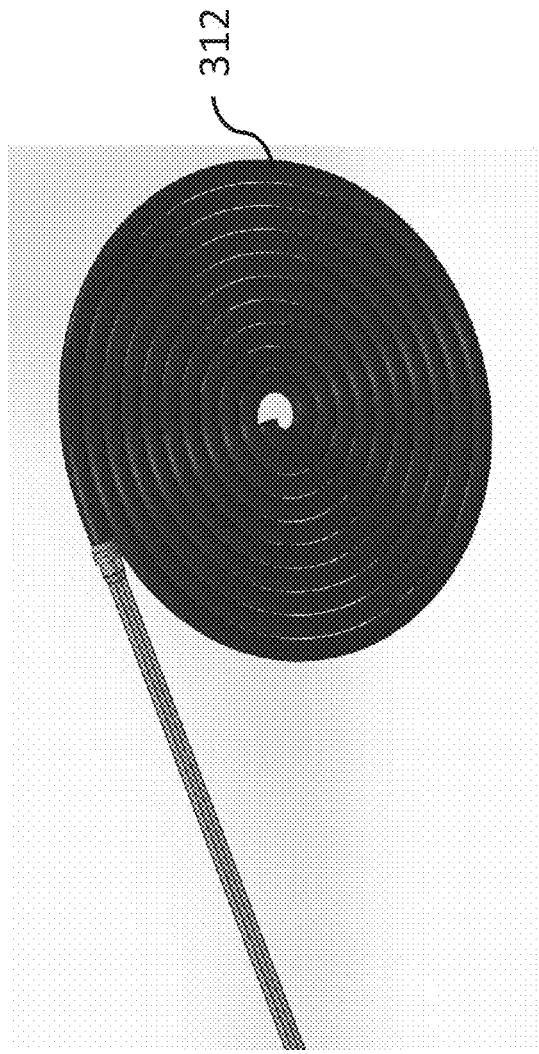

According to some exemplary embodiments, for example as shown in FIGS. 3B and 3C, the sack 306 which is optionally at least partly covered with a membrane is pre-formed to a spiral template, in which the internal scaffold, for example a spiral tube or the spiral coil 312 is introduced. In some embodiments, the introduction of the spiral tube or the spiral coil 312 provides mechanical strength to the sack 306.

According to some exemplary embodiments, for example as shown in FIGS. 3D and 3E, an introduction tube 308 is connected to the sack 306. In some embodiments, the introduction tube 308 is connected to the sack 306 via the port 310. In some embodiments, the introduction tube 308 is used to introduce the sack 306 into the peritoneal cavity through the peritoneum access opening.

Figure 3F:
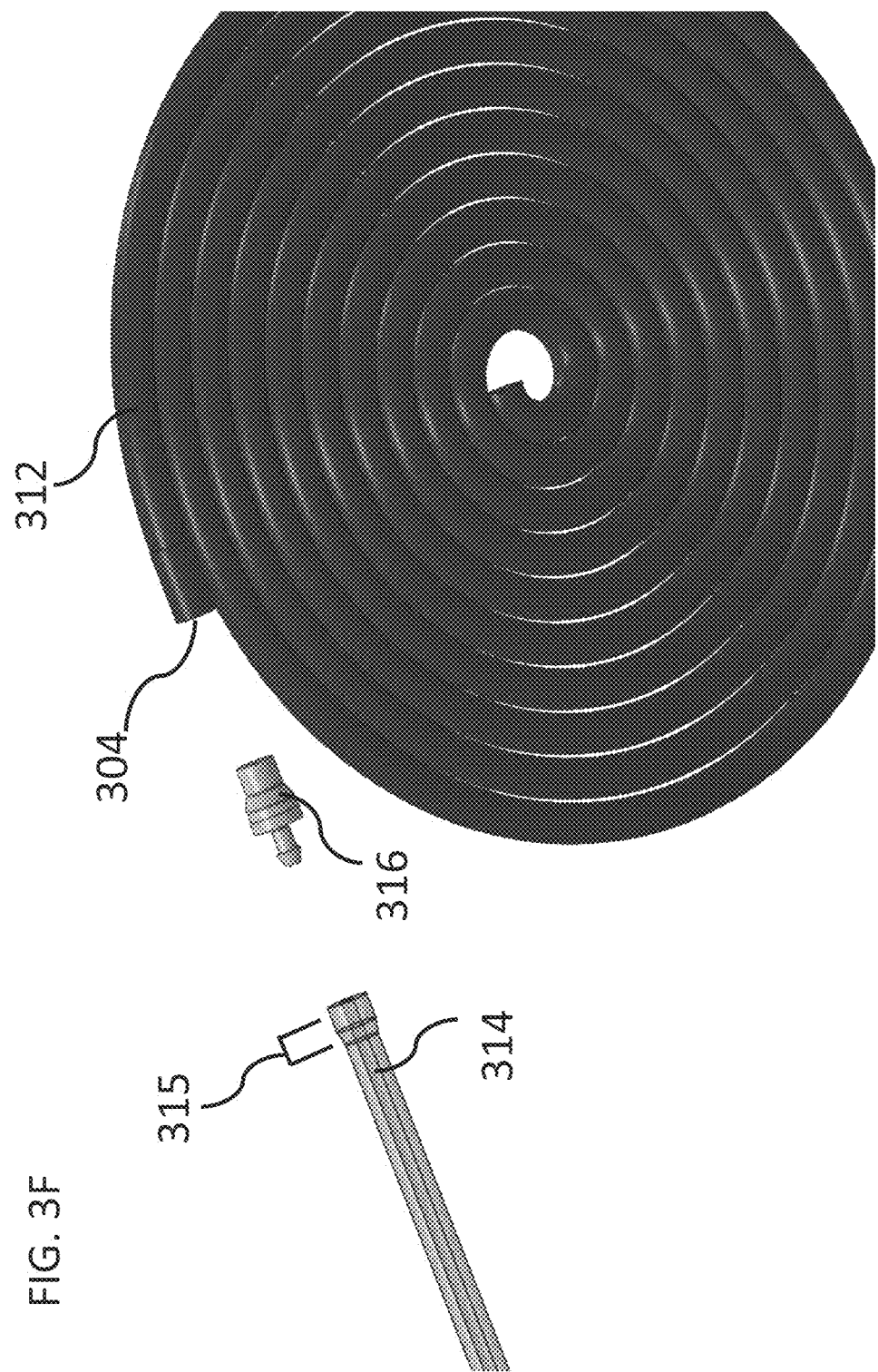

According to some exemplary embodiments, for example as shown in FIG. 3F a connector 316 is partly positioned within an opening 304 of the spiral coil 312. In some embodiments, tube 314 is connected to an end of the connector 316 which is positioned outside of the spiral coil. In some embodiments, the tube 314 is connected to the connector 316 prior to the insertion of the spiral coil into the body. Alternatively, the connector 316 comprises an interlocking mechanism that allows for example, to connect the tube 314 to the connector when the spiral coil is within the body.

Figure 3H:
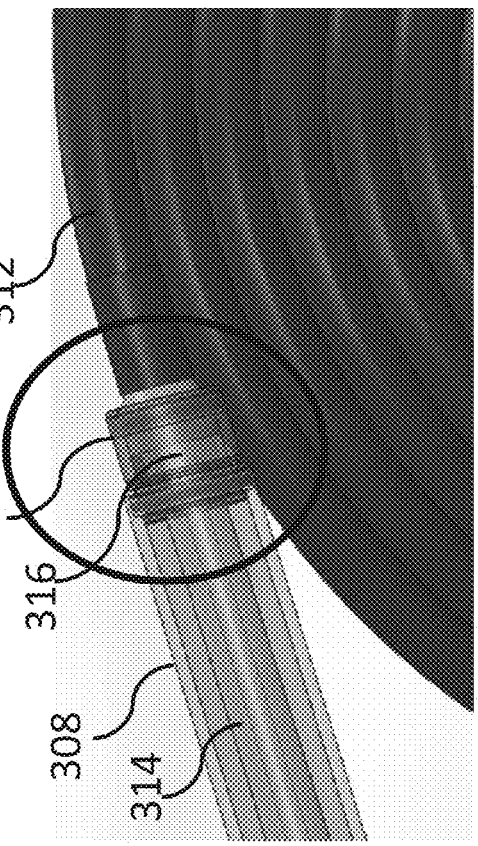
Figure 3G:
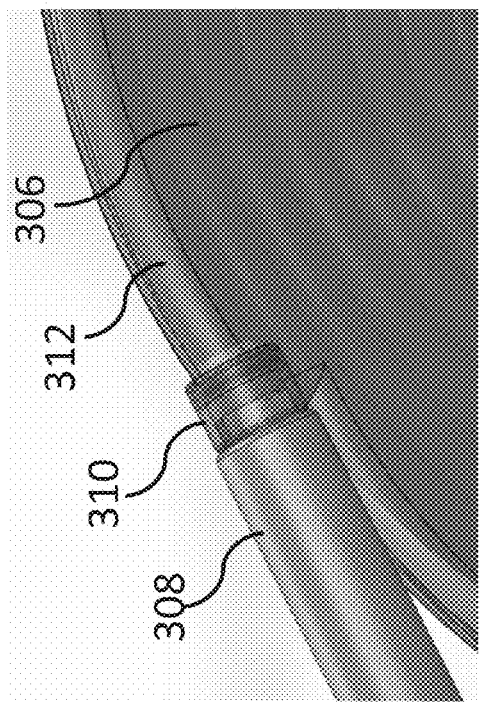
Figure 3I:
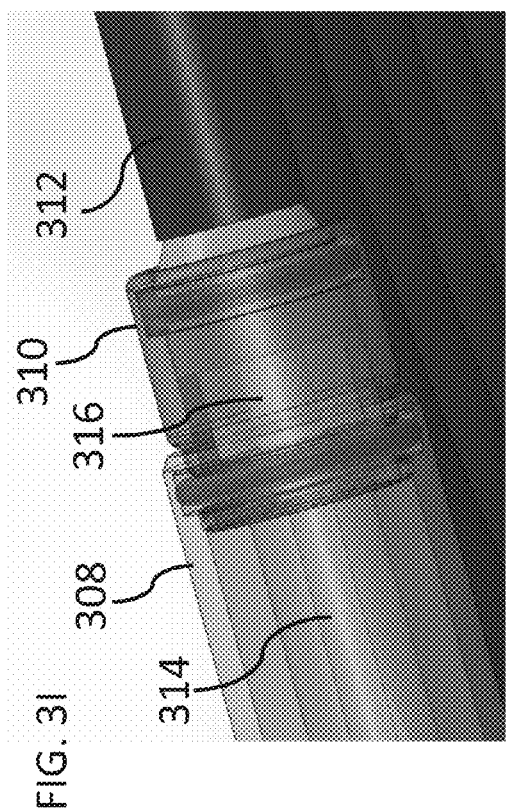

Reference is now made to FIGS. 3G to 3I, depicting an internal scaffold, for example a spiral coil within the sack, according to some embodiments of the invention.

According to some exemplary embodiments, the internal scaffold, for example spiral coil 312 and the tube 314 are pushed through the introduction tube 308 into the sack 306. In some embodiments, the connector 316 is shaped to prevent the insertion of the tube 314 into the sack 306. In some embodiments, the external diameter of the connector 316 is larger than the internal diameter of port 310. Alternatively or additionally, for example as shown in FIG. 3F, a distal section 315 of tube 314 facing connector 316 has a larger diameter compared to the diameter of port 310. In some embodiments, connector 316 interlocks, optionally irreversibly, with port 310, for example to prevent pulling out the spiral coil 312 from the sack 306. In some embodiments, the connector 316 irreversibly interlocks with port 310 using an interference locking mechanism, for example a snap-fit locking mechanism positioned in the connector 316 and/or in port 310. Alternatively, the connector 316 reversibly interlocks with port 310, for example by rotating the connector 316. Optionally, the connector 316 is rotated by rotating tube 314.

According to some exemplary embodiments, for example as shown in FIG. 3J, when the spiral coil 312 is positioned within the sack 306, the introduction tube 308 is disconnected from port 310 and retracted. In some embodiments, the locking between the connector 316 and port 310 is stronger compared to the locking between the introduction tube 308 and the port 310. Alternatively, the introduction tube 308 is disconnected from the port 310 by turning the introduction tube clockwise or counterclockwise. In some embodiments, the introduction tube is turned in an opposite direction to the rotation direction required to lock the spiral coil 312 within sack 306, for example by interlocking the connector 316 with port 310.

Figure 3K:
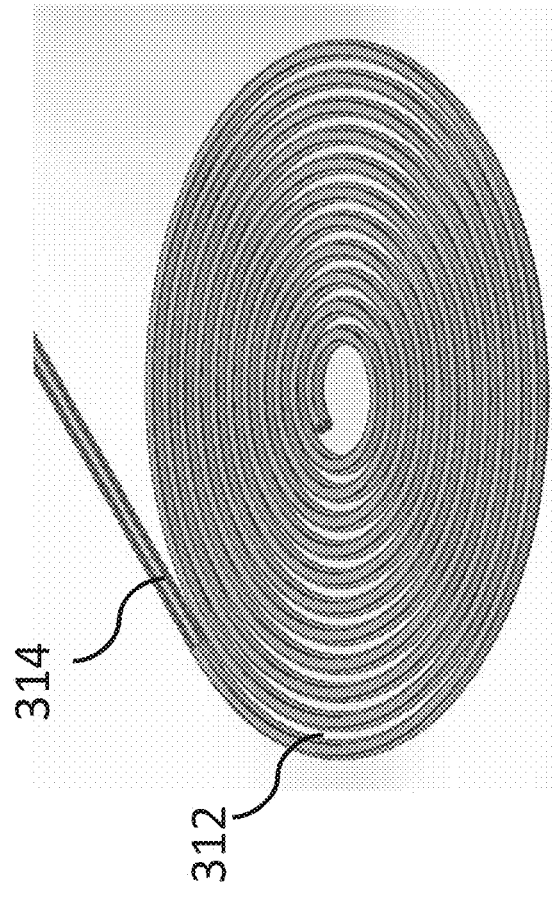
Figure 3L:
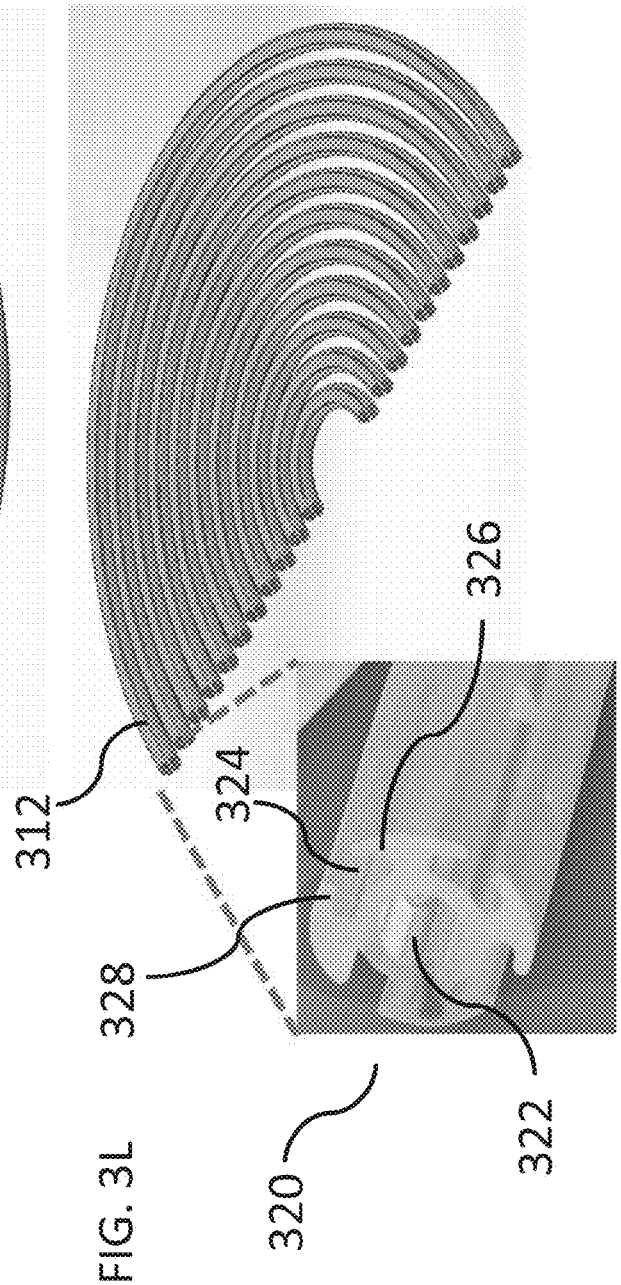

Reference is now made to FIGS. 3K and 3L depicting an internal spiral scaffold, according to some embodiments of the invention. According to some exemplary embodiments, internal scaffold, for example spiral coil 312 is a tubular structure with an internal lumen 322. In some embodiments, the tubular structure contains a plurality of openings connecting between the external surface of the spiral coil and the internal lumen 322. In some embodiments, fluid within the sack penetrates through the openings in the spiral coil into the internal lumen. In some embodiments, the internal lumen of the spiral coil directs the fluid out from the sack.

According to some exemplary embodiments, the internal scaffold, for example spiral coil 312 is used for providing mechanical strength and not to direct fluid through an internal lumen out from the sack. In some embodiments, the internal scaffold, for example spiral coil 312 comprises voids, for example void 324 on the outer surface of the internal scaffold to allow fluid to flow freely within the sack. In some embodiments, the fluid exits the sack through an opening in the sack, for example port 310 that is connected to a draining tube, for example tube 314.

Figure 3M:
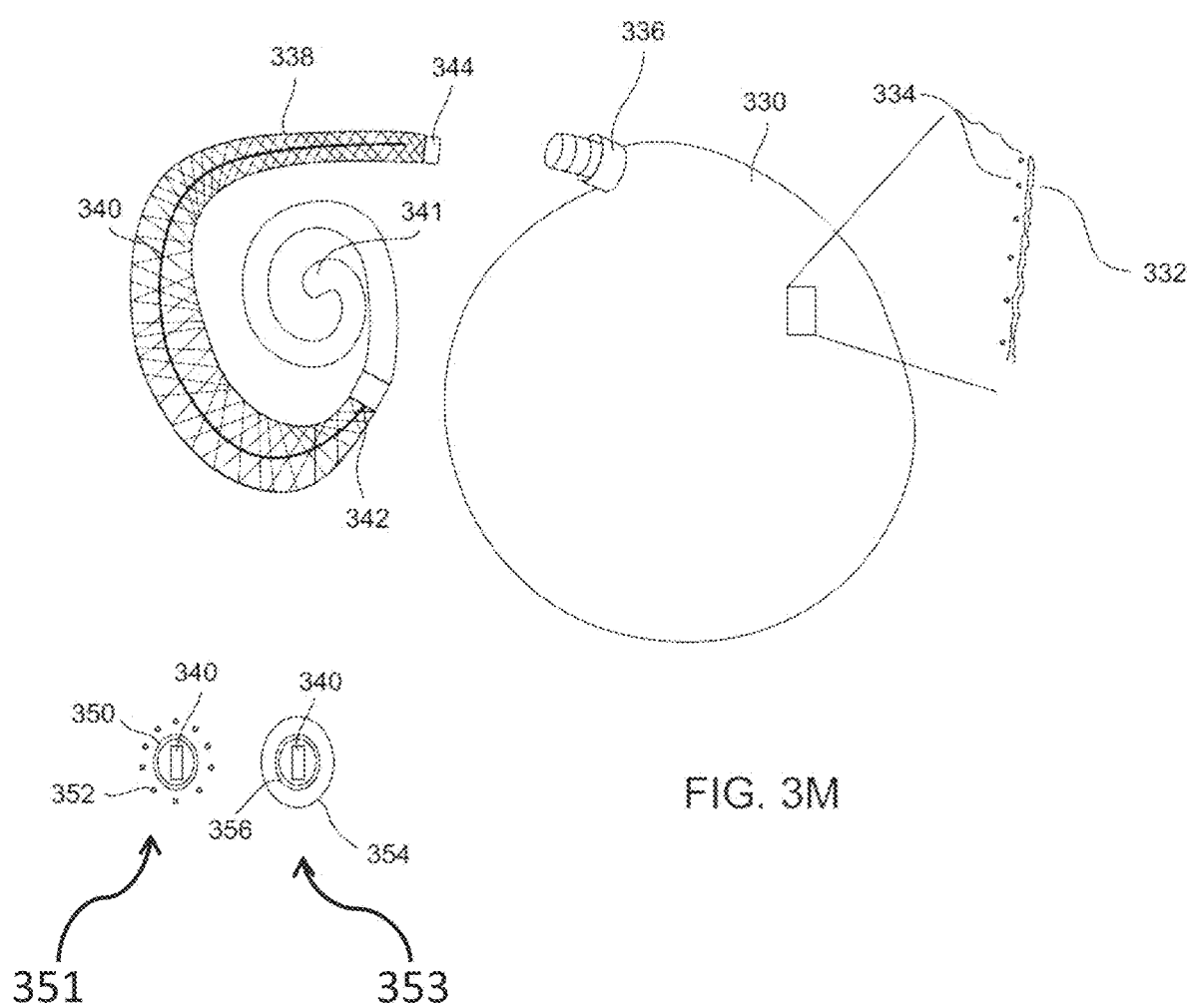
Figure 3N:
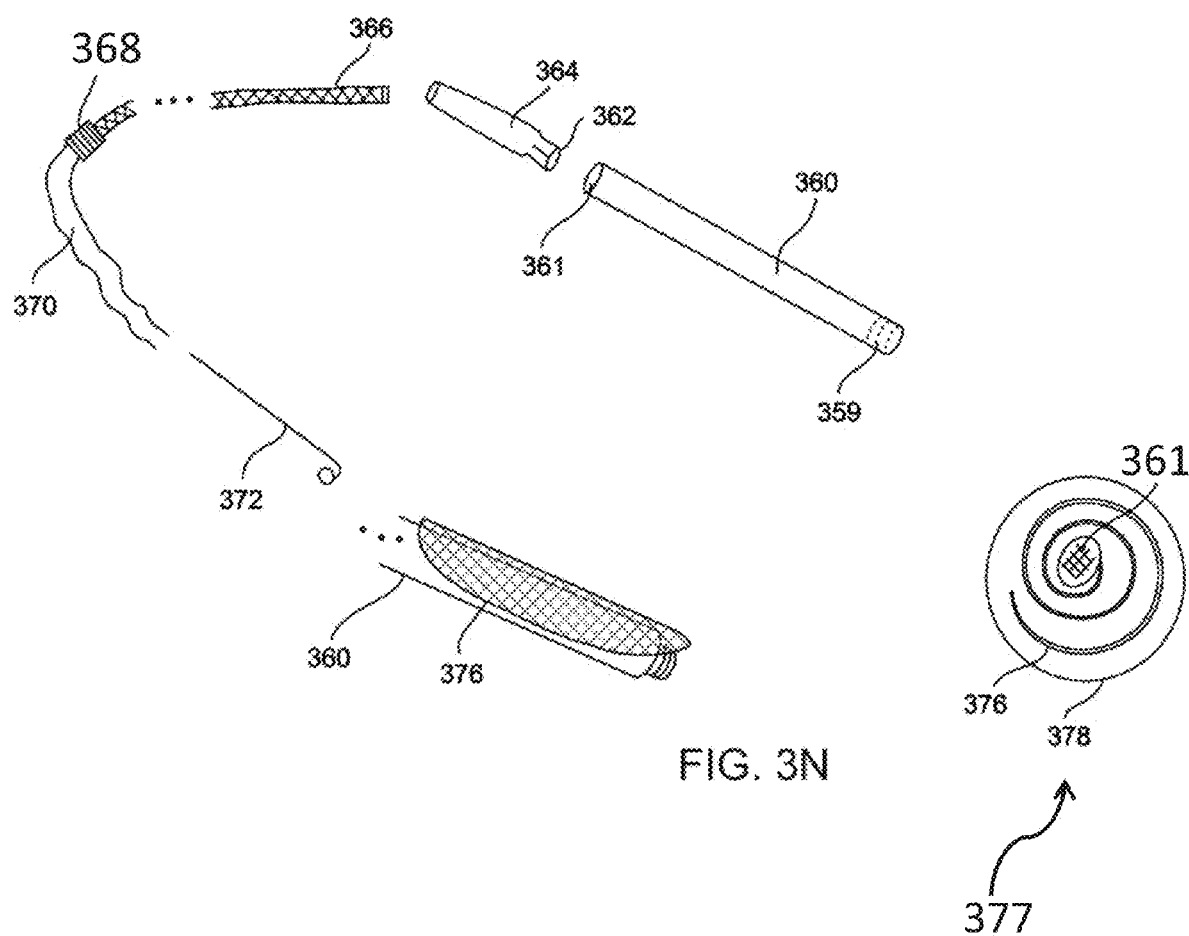

According to some exemplary embodiments, for example as shown in FIG. 3M, a fluid absorbing unit comprises sack 330, which is optionally has an external covering membrane 332 and an internal support layer 334. In some embodiments, covering membrane 332 is a porous membrane which allows fluids to enter into sac 330. In some embodiments, the pores in membrane 332 are small enough not to allow penetration of cells into the sac. In some embodiments, the pores size, for example the pores width or the maximal dimension of the pores is smaller than 10 micrometer (micron), for example 9 micron, 8 micron, 7 micron, 0.5 micron, 0.45 micron, 0.25 micron or any intermediate or smaller size. Alternatively, the pores size is 10 micron or larger, for example 10 micron, 11 micron, 12 micron or any intermediate or larger size.

According to some exemplary embodiments, the internal support layer 334 is shaped and sized to isolate the external covering membrane 332 from an internal scaffold positioned within the sack 330. In some embodiments, the internal support layer is made from a fabric, optionally an elastic fabric, or fabricated as a nonwoven sheet. In some embodiments, the elastic fabric is strong enough to resist the force applied by an internal scaffold inserted into the sack or any pressure applied towards the membrane from within the sack, and to resist the collapse of covering layer 334 (membrane) and pressure from biological tissues. In some embodiments, the support layer 334 is porous, for example to allow fluid penetrating through the covering membrane 332 to enter into the sack 330. In some embodiments, the support layer 334 is surface treated with ionically charged groups, for example to increase the driving infiltration force and/or to influence the infiltration of certain components of the extracted fluids.

According to some exemplary embodiments, the sack 330 comprises at least one opening. In some embodiments, a port, for example port 336 is placed inside the opening. In some embodiments, a distal header 344 of an internal scaffold, for example braided tube 338 is shaped to be inserted through the port 336 into the sack 330. In some embodiments, the external diameter of the braided tube is smaller than the internal diameter of the port 336. In some embodiments, the diameter of the braided tube is in a range of 2-8 mm, for example 2, 3, 4, 5, 6, 7, 8 mm or any intermediate value. In some embodiments, the diameter of the port 336 is in a range of 3-9 mm, for example 3, 4, 5, 6, 7, 8, 9 mm or any intermediate value. In some embodiments, the braided tube 338 comprises an inner stylet 340, which is optionally made from a shape memory material, for example Nitinol. In some embodiments, the inner stylet is shaped to maintain the braided tube 338 flat when the braided tube 338 is introduced and positioned within sack 330.

According to some exemplary embodiments, the internal scaffold comprises a connector 342 positioned in a proximal section of the braided tube 338. In some embodiments, the connector 342 at least partly or fully surrounds the braided tube 338. In some embodiments, once the braided tube 338 is pushed into the sack 330, the connector 342 is clocked onto port 336. In some embodiments, the connector interlocks, optionally irreversibly with port 336. Alternatively, the connector 342 reversibly interlocks with the port 336. In some embodiments, the connector 342 interlocks with the port 336 by rotation of the connector 342 or by rotation of a draining tube 341 connected to the connector 342. Alternatively, the connector 342 interlocks with the port 336 by applying force against the port 336. In some embodiments, the connector 342 is seal-locked into the port 336, optionally by pressing radially on an encaged O-ring sealer. In some embodiments, sealing-locking the connector 342 into the port 336, optionally by pressing radially on the engaged O-ring sealer allows a snap out option when applying a reasonable high force of few newtons. In some embodiments, snapping out or releasing is only possible by introducing a designated tool.

According to some exemplary embodiments, the stylet 340 has a rectangular or a circular cross section. In some embodiments, for example as shown in a cross-section view 351 the stylet 340 is positioned and extended along a tube 350, for example a silicon tube. In some embodiments, the silicon tube is wrapped with an external braided layer. Alternatively, for example as shown in a cross-section view 353 the stylet 340, optionally a stylet with a rectangular cross-section is positioned within and extending along tube 356, for example a silicon tube. In some embodiments, the tube 356 is wrapped with an external coil.

According to some exemplary embodiments, the stylet 340 is memory shaped to the desire spiral flat form of the absorption chamber 330. In some embodiments the stylet comprises several mandrels with varying cross sections to best provide a spiral shape with similar stiffness or rigidity. Optionally, smaller cross sections areas are located at the distal (tip) part of the stylet and larger cross sections are at the proximal part of the stylet. In some embodiments, the stylet 340 is tapered and varies continuously in cross section sizes or diameters. In some embodiments, the Stylet 340 is made of materials that are stiffer than the covering layers, such as Nitinol, Stainless steel, Cobalt Chromium or Polymers or any combination of these materials.

Reference is now made to FIG. 3N depicting components of a fluid absorbing when it is introduced into the peritoneum, according to some embodiments of the invention.

According to some exemplary embodiments, introducer tube 360 comprises an internal thread 359 at the distal end of the tube or protruding gripping features that fit mating grooves of the port 336. In some embodiments, the port of the sack is connected to the internal thread 359. In some embodiments, a releaser, for example releaser 364 comprises a rectangular shaped end 362 with a rectangular cross-section. Alternatively or additionally, the releaser 364 comprises gripping features that tightly fit corresponding grooves located on the inner surface of the port 336. In some embodiments, the rectangular shaped end 362 fits an internal shape in the introducer tube 360. In some embodiments, to release the introducer tube 360 from the port of the sack, the rectangular shaped end 362 of the releaser 364 is inserted into the proximal end 361 of the introducer tube 360. Optionally, the releaser 364 is embedded in introducer 360 that is sealed in its proximal end, for example to avoid gas leakage. In some embodiments, once the releaser 364 is at least partially within the introducer tube 360, it is turned clockwise or counterclockwise or pushed or pulled to release the port from the internal thread 359 of the introducer tube 360. In some embodiments, releaser 360 allows the release of the braided tube 338 in order to retrieve the braided tube 338 and/or the entire chamber.

According to some exemplary embodiments, the introducer tube 360 is released from the port of the sack after the braided coil 366, optionally preformed to acquire a spiral formation is introduced into the sack. Alternatively or additionally, the introducer tube 360 is released from the port when a connector 368 positioned in the proximal end of the braided coil 366 interlocks with the port, as previously described. In some embodiments, a draining tube 370 is connected to the opposite side of the connector 368.

According to some exemplary embodiments, the braided coil 366 is pushed into the sack by a pusher or a mandrel 372 that is optionally connected to the draining tube 370, or to the connector 368. In some embodiments, the braided coil 366 is pushed into the sack by turning or rotating the mandrel 372 clockwise or counterclockwise.

According to some exemplary embodiments, for example as shown in FIG. 3N, the sack 376 is folded around or within the introducing tube 360 during the deployment process of the fluid absorbing unit. In some embodiments, for example as shown in a cross-section view 377, an inner stylet wire 361 is inserted into or outside sack 376 in order to improve deployment performance. In some embodiments, during the deployment process the sack 376 which is in a folded state is covered by cover liner 378. In some embodiments, the cover liner 378 prevents the membrane 380 to contact bodily tissues during the deployment process and/or to provide sufficient stiffness or sufficient rigidity to slide in through a laparoscopic introducer or other introducer tools. Additionally or alternatively, the cover liner 378 prevents unwanted expanding of the sack 376 during the deployment process. In some embodiments, the diameter of the cover liner 378 is smaller than the diameter of the peritoneum opening. In some embodiments, the cover liner 378 is large enough to retain the folded sack 376. In some embodiments, the liner inner diameter is in a range of 6 to 14 mm, for example 6, 7, 8, 10 mm or any intermediate or larger value. In some embodiments, the thickness of the cover liner 378 is in a range of 0.05-1 mm. In some embodiments, the cover liner is long enough to be pulled out from the body. In some embodiments, the cover liner 378 is made of surface treated smooth or hydrophilic polymer. Alternatively, the cover liner 378 is made from a resorbable and/or a soluble material.

According to some exemplary embodiments, the cover liner 376 is clamped on the edge of the sack 378, for example to assist with unfolding the sack optionally while being pushed back in respect to the sack and revealing it.

According to some exemplary embodiments, for example as shown in FIGS. 4A-4C, a fluid absorbing unit 402, for example a fluid extraction chamber comprises a membrane wrapped chamber 404. In some embodiments, the membrane wrapped chamber 404 comprises an outlet connector 412, which is similar to port 310. In some embodiments, the membrane wrapped chamber 402 is shaped as a disc and comprises an outline sealing 406 in the circumference of the chamber. In some embodiments, the outline sealing 406 seals a connection between two membranes positioned on opposite sides of the disc-shaped chamber 402.

According to some exemplary embodiments, draining tube 401 comprises sub-muscular suturing leaflets 410 for anchoring the draining fluid within the body, for example within the peritoneal cavity, optionally to the peritoneum. In some embodiments, at least one fixation band 408 is wrapped around the draining tube, for example to fixate the position of the draining tube 401 within the peritoneum access port.

According to some exemplary embodiments, for example as shown in FIGS. 4B and 4C a spiral braided tube 414 is pre-formed to form a spiral when placed inside a round chamber, for example membrane wrapped chamber 404.

Exemplary Deployment of an Implanted System

Reference is now made to FIGS. 5A-5G depicting a deployment of an implanted system, according to some embodiments of the invention.

Figure 5B:
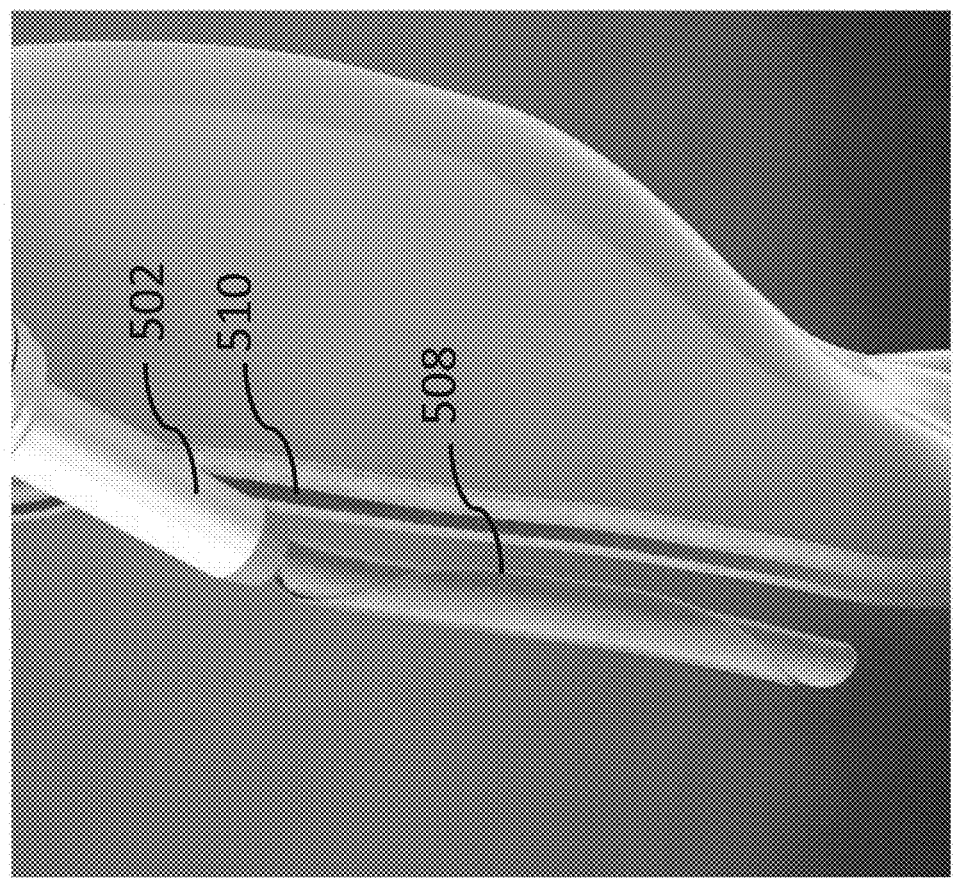
Figure 5A:
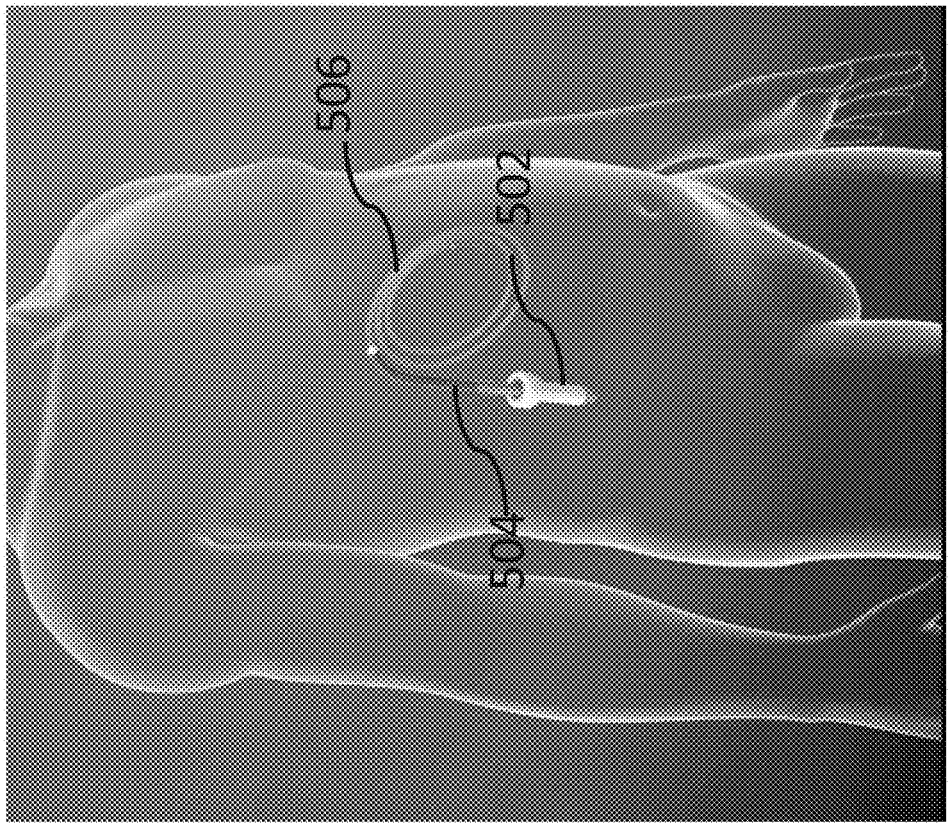

According to some exemplary embodiments, for example as shown in FIG. 5A an opening is made in the body wall, and in the peritoneum. In some embodiments, a sack 508 in a folded state is wrapped around an introduction tube 504. In some embodiments, for example as shown in FIG. 5B the introduction tube 504 is pushed through a peritoneum port 502 into the peritoneum.

Figure 5D:
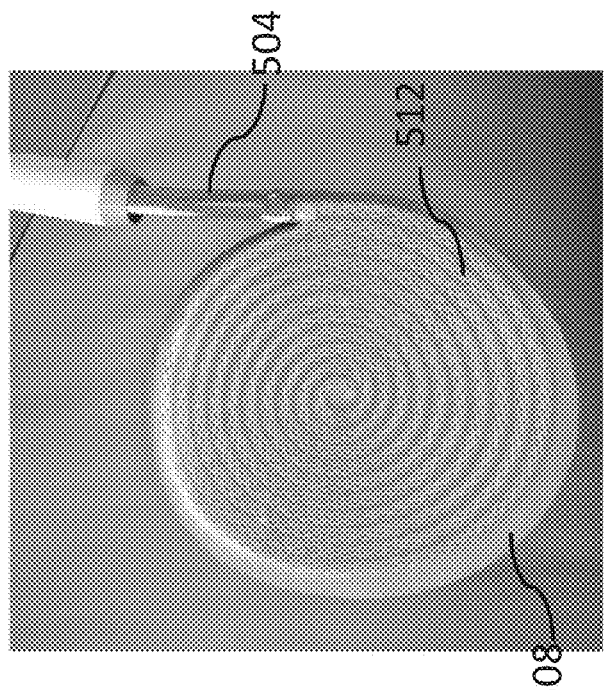
Figure 5C:
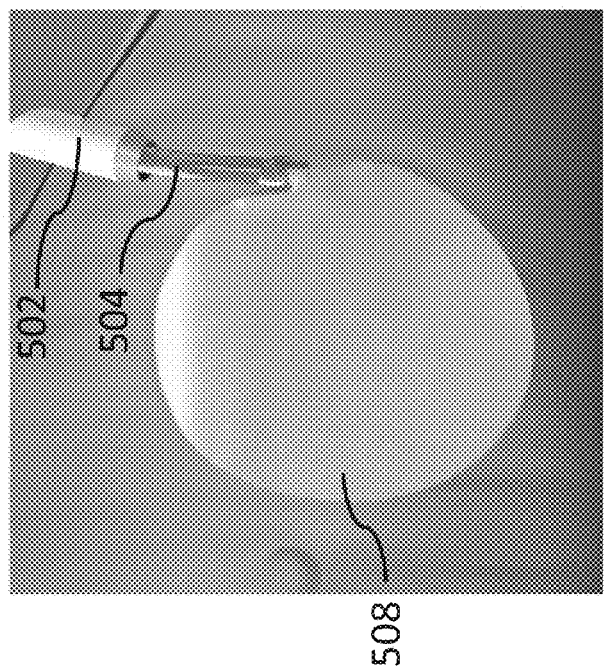

According to some exemplary embodiments, for example as shown in FIG. 5C the sack 508 unfolds within the peritoneum. In some embodiments, for example as shown in FIG. 5D, a braided tube 512 is pushed through the introduction tube 504 into the unfolded sack 508, for example to stabilize the sack 510 in an unfolded state.

Figure 5E:
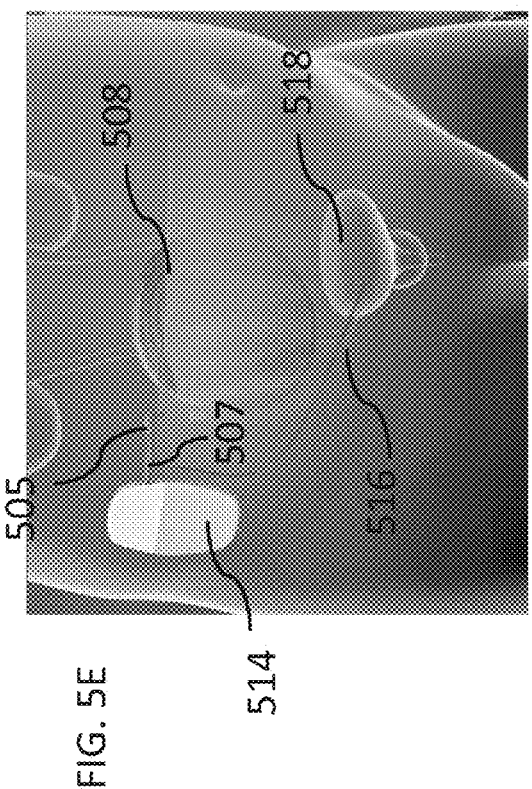

According to some exemplary embodiments, for example as shown in FIG. 5E when the sack 508 is stabilized in an unfolded state the introduction tube is retracted. In some embodiments, a draining tube 507 connected to the sack 508 comprises a cuff 505 which is positioned in an opening of the peritoneum. In some embodiments, a control unit 514 is implanted outside the peritoneum and optionally subcutaneous. In some embodiments, the draining tube 507 is connected to the control unit 514, optionally to a pump placed inside the control unit 514. In some embodiments, the control unit is connected by a draining catheter 516, for example a pigtail catheter to the urinary system, optionally to the urine bladder 518.

According to some exemplary embodiments, for example as shown in FIG. 5F, the control unit 514 is connected by the pigtail catheter to the renal pelvic 515.

Figure 5G:
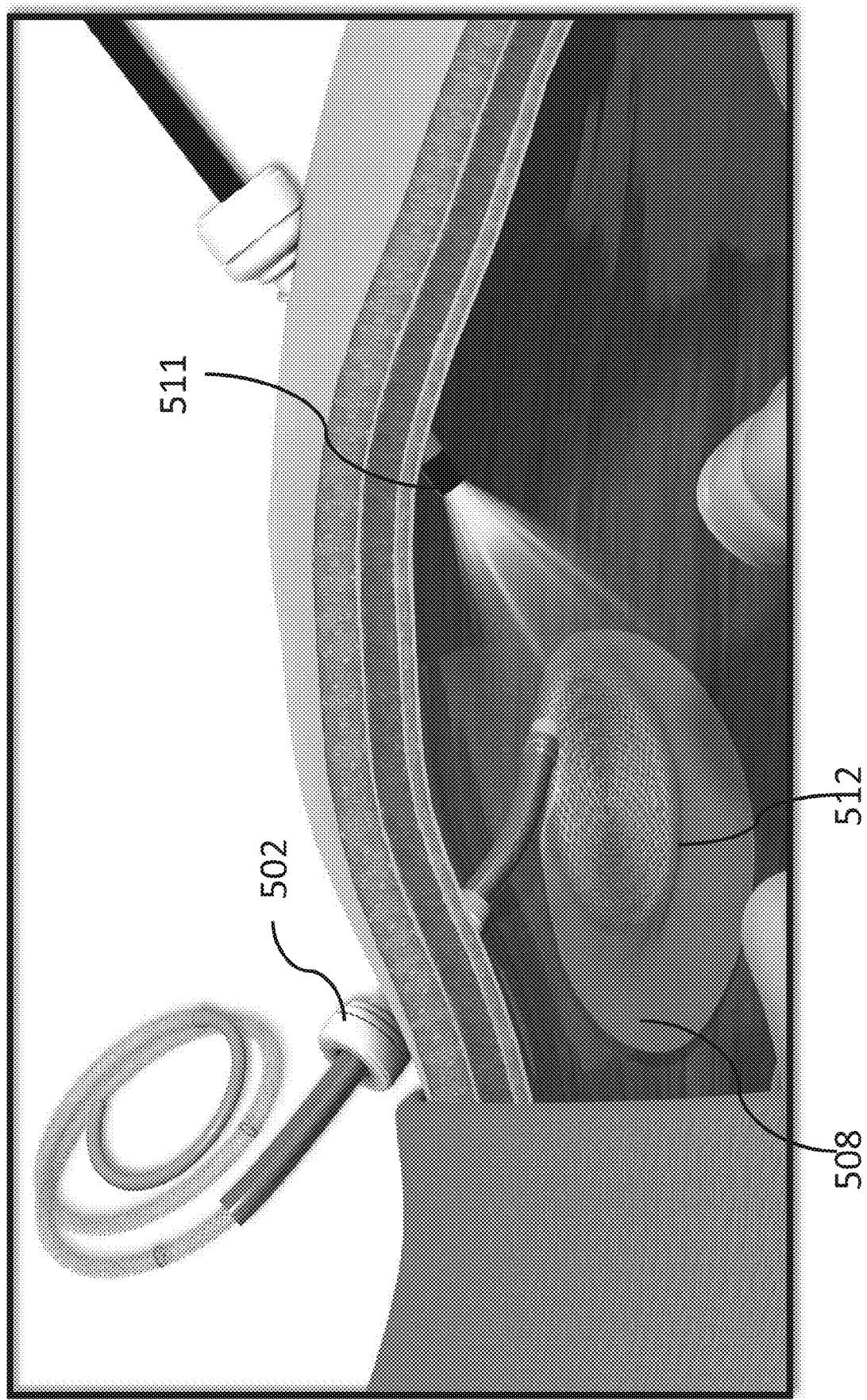

According to some exemplary embodiments, for example as shown in FIG. 5G, the sack 508 is introduced and deployed within the peritoneum using a laparoscope 511, which allows to visualize the introduction and positioning process of the sack 508. In some embodiments, the sack is deployed and positioned in the peritoneum without using any anchors.

Reference is now made to FIG. 6, depicting a process for deployment of an implantable device, according to some embodiments of the invention.

According to some exemplary embodiments, a catheter with a folded sack is introduced into the peritoneum at 602. In some embodiments, the folded sack is wrapped around an introduction tube. In some embodiments, the folded sack is enclosed within a lumen of a tube, for example an introduction tube. Optionally, the folded sack is covered by an external layer or an external sheet protecting the sack which is optionally covered by a membrane, during the insertion stage into the peritoneum. Alternatively or additionally, the external layer or the external sheet covering the folded sack prevents the unfolding of the sack.

According to some exemplary embodiments, the sack is unfolded at 604. In some embodiments, the sack is unfolded when it is positioned in a desired location within the peritoneum. In some embodiments, the sack is unfolded by retracting a layer or a cover or an envelope covering the sack. In some embodiments, a tube covering the sack during the introduction of the sack into the peritoneum is retracted, for example to allow the sack to unfold.

According to some exemplary embodiments, an internal scaffold or an internal skeleton is inserted into the inner lumen of the unfolded sack at 606. In some embodiments, the internal scaffold, for example a braided tube or a coiled tube is inserted by rotating the internal scaffold. In some embodiments, rotation of the internal scaffold generates a forward movement of the internal scaffold into the sack. Alternatively, the internal scaffold is pushed into the sack. In some embodiments, when the internal scaffold is positioned in a desired location and/or is pushed to a desired length into the sack a locking mechanism is activated, for example to prevent the exit of the internal scaffold from the sack. In some embodiments, the internal scaffold is locked within the sack by rotation of the internal scaffold or pushing the internal scaffold. In some embodiments, the internal scaffold is reversibly or irreversibly locked or fixed within the sack.

According to some exemplary embodiments, a control device is implanted at 608. In some embodiments, the control device is implanted outside of the peritoneum. Optionally, the control device is implanted subcutaneously. In some embodiments, the control device is implanted inside a pocket and/or is anchored to a tissue.

According to some exemplary embodiments, the sack is connected to the control device at 610. In some embodiments, the sack is fluidically connected to the control device by a tube, for example a draining tube. Optionally, the draining tube is connected to a pump located inside the control device. In some embodiments, the draining tube is connected to the internal scaffold positioned inside the sack. Optionally, the draining tube is the internal scaffold, for example a different region of the internal scaffold.

According to some exemplary embodiments, a draining catheter is connected to the control device at 612. In some embodiments, the draining catheter is fluidically connected to a pump located inside the control device. In some embodiments, a first opening of the draining catheter is fluidically connected to the control device. In some embodiments a second opening of the draining catheter is placed in the urinary system, for example in the kidney or in the urinary bladder.

Exemplary Beads-Filled Sack

Figure 7A:
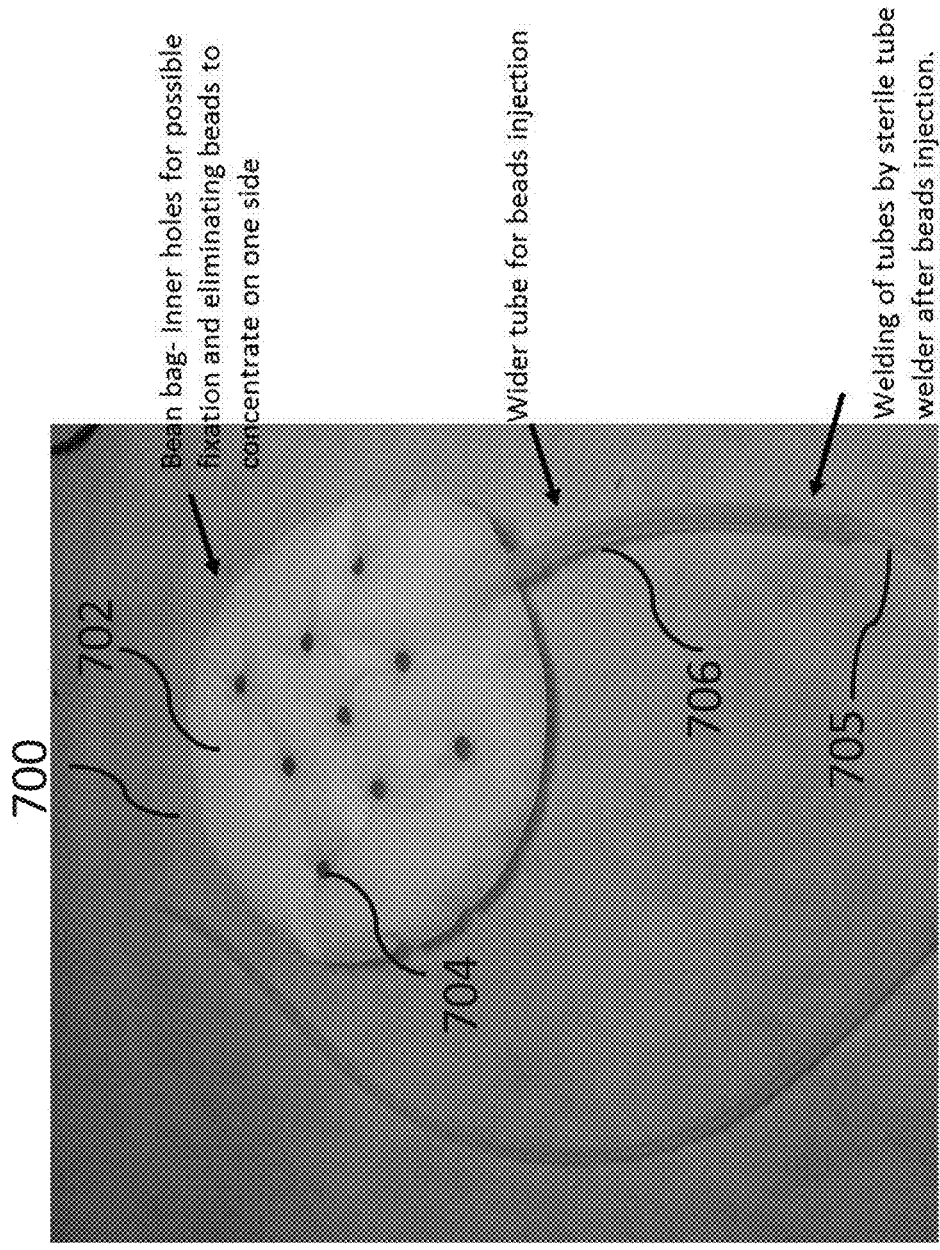

Reference is now made to FIG. 7A depicting a beads-filled sack, according to some embodiments of the invention.

According to some exemplary embodiments, a sack, for example sack 700 is covered by a membrane, for example a membrane 702. In some embodiments, a filling tube, for example filling tube 706 is connected to an opening in sack 700, and is used to fill the sack 700 with beads. In some embodiments, the beads provide mechanical strength to the sack 700, for example to maintain the outer surface of the sack 700 flat and optionally semi-rigid. In some embodiments, the beads maintain a non-collapsed inner sack volume. Alternatively or additionally, the beads are ionically charged, for example to induce osmotic pressure that attracts fluids from the tissue into the sack 700. In some embodiments, the osmotic pressure is induced by the beads in addition to an active vacuum force applied by a pump connected to the sack. Alternatively, the osmotic pressure is induced by the beads instead of the vacuum force. In some embodiments the beads size is in a range of 0.5 to 3 mm, for example 0.5, 1, 2, 3 mm or any intermediate value. In some embodiments, the smallest dimension of the beads is at least 0.5 mm, for example 0.5, 1, 1.5 mm or any intermediate or larger value.

In some embodiments, the beads are spherical or ellipsoid beads. In some embodiments, the beads are semi-porous and/or drilled. In some embodiments, the beads comprise a rigid outer surface, for example to increase overall permeability of membrane 702 contact area.

According to some exemplary embodiments, the sack 700 is shaped as a disc having two flat surfaces. In some embodiments, the sack comprises at least two openings in the flat surfaces that allow fluid to pass through the flat surfaces without entering into the sack lumen. In some embodiments, these openings for example opening 704, are formed by connected the inner sides of the two flat surfaces in different positions. In some embodiments, connecting the inner sides of the flat surfaces restricts the movement of the beads within the lumen of the sack 700. Optionally, restricting the movement of the beads forces the beads to evenly distribute within the lumen of the sack 700. In some embodiments, evenly distribution of the beads allows the beads to apply an even mechanical force on the inner surface of the sack 700 along the entire inner surface. Additionally or alternatively, evenly distribution of the beads, for example charged beads within the sack allows to apply an even osmotic pressure along the entire surface of the sack 700.

Figure 7B:
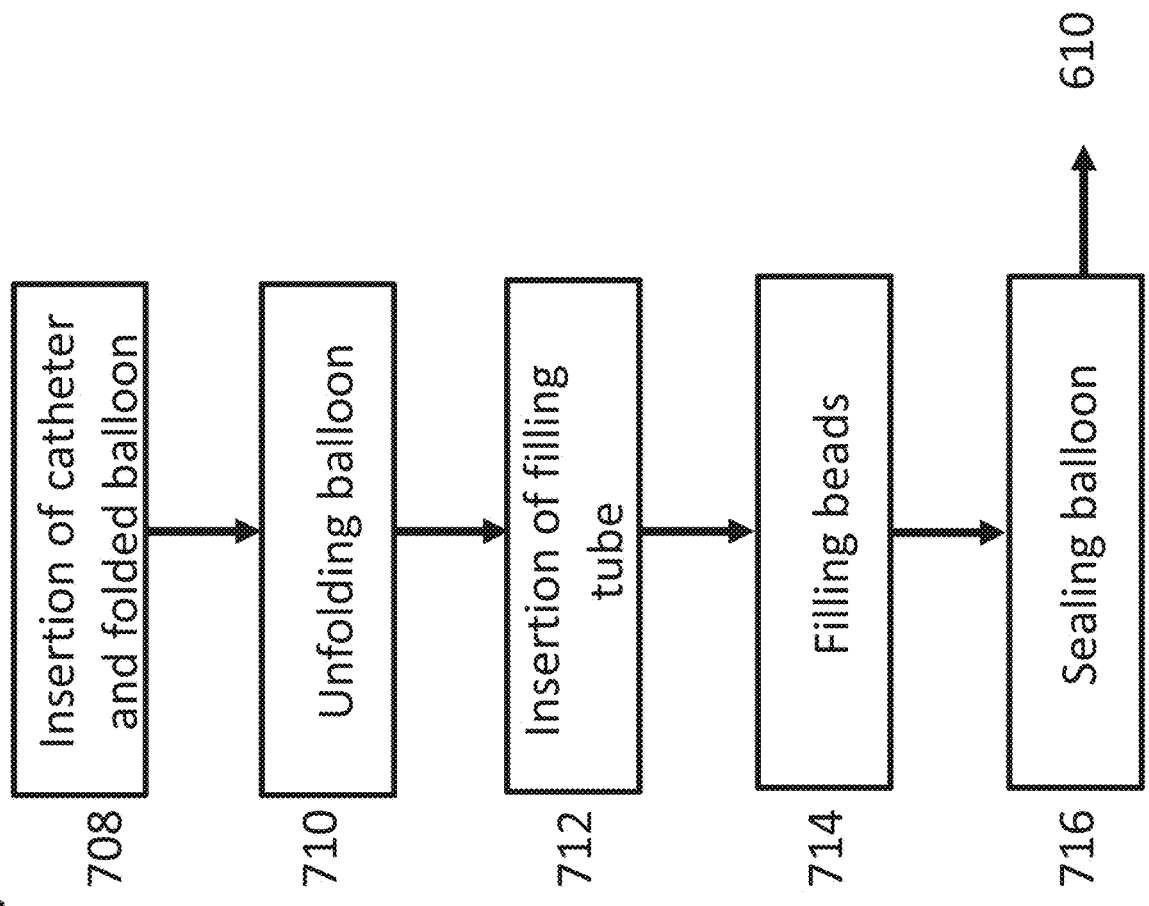

Reference is now made to FIG. 7B depicting a process for deploying a beads-filled sack, according to some embodiments of the invention.

According to some exemplary embodiments, a catheter and a folded balloon or a folded sack is introduced into the peritoneum at 708. In some embodiments, the folded balloon is covered by a layer or a sheet during the introduction stage, for example to prevent the folding of the balloon and/or to isolate the balloon from bodily tissue during the introduction stage, for example as described in FIG. 6. In some embodiments, the balloon is covered with a membrane.

According to some exemplary embodiments, the balloon unfolds at 710. In some embodiments, the balloon is unfolded when it is positioned in a desired location within the peritoneum. In some embodiments, the balloon unfolds by removing a cover or a layer covering the balloon. Alternatively or optionally, the balloon unfolds by retracting a tube covering the balloon.

According to some exemplary embodiments, a filling tube is connected to the balloon at 712. In some embodiments, a filling tube is connected to a proximal opening of an introduction tube connected to an opening of the sack. Alternatively, the filling tube is pushed inside the introduction tube into the balloon.

According to some exemplary embodiments, the balloon is filled with beads at 714. In some embodiments, the beads are pushed through the filling tube into the balloon, optionally by applying force through an opening of the filling tube placed outside the peritoneum.

According to some exemplary embodiments, the beads-filled balloon, for example a beads-filled sack is at least partly sealed at 716. In some embodiments, the beads-filled sack is at least partly sealed to prevent the release of beads out from the sack. In some embodiments, the balloon-filled sack is partly sealed by placing a mesh in an opening of the balloon with pores that are smaller than the size of the beads. Alternatively, the filling tube or an opening in the sack that was used to fill the beads is sealed.

According to some exemplary embodiments, once the beads cannot be released from the sack, the sack is connected to a control device at 610, as described in FIG. 6.

In some embodiments, the beads are fabricated to have high porosity, for example porosity larger than 1000 kDa. In some embodiments, the porosity is larger than 65 kDa, for example larger than 80, 10, 120 kDa or any intermediate, smaller or larger value. In some embodiments, the porosity of the beads is larger than the size of albumin. In some embodiments, the beads are manufactured to have specific polarity, charge, size-exclusion and/or affinity. In some embodiments, for a relatively large chamber in diameter of 160 mm and thickness of 6 mm, using drilled sphere, in size of 2.5 mm for instance, with material Polypropele (0.9 gr/cm^3) yields number of 120 beads inside sack, weighing 72 gram.

Exemplary Gel-Filled Chamber

Figure 8A:
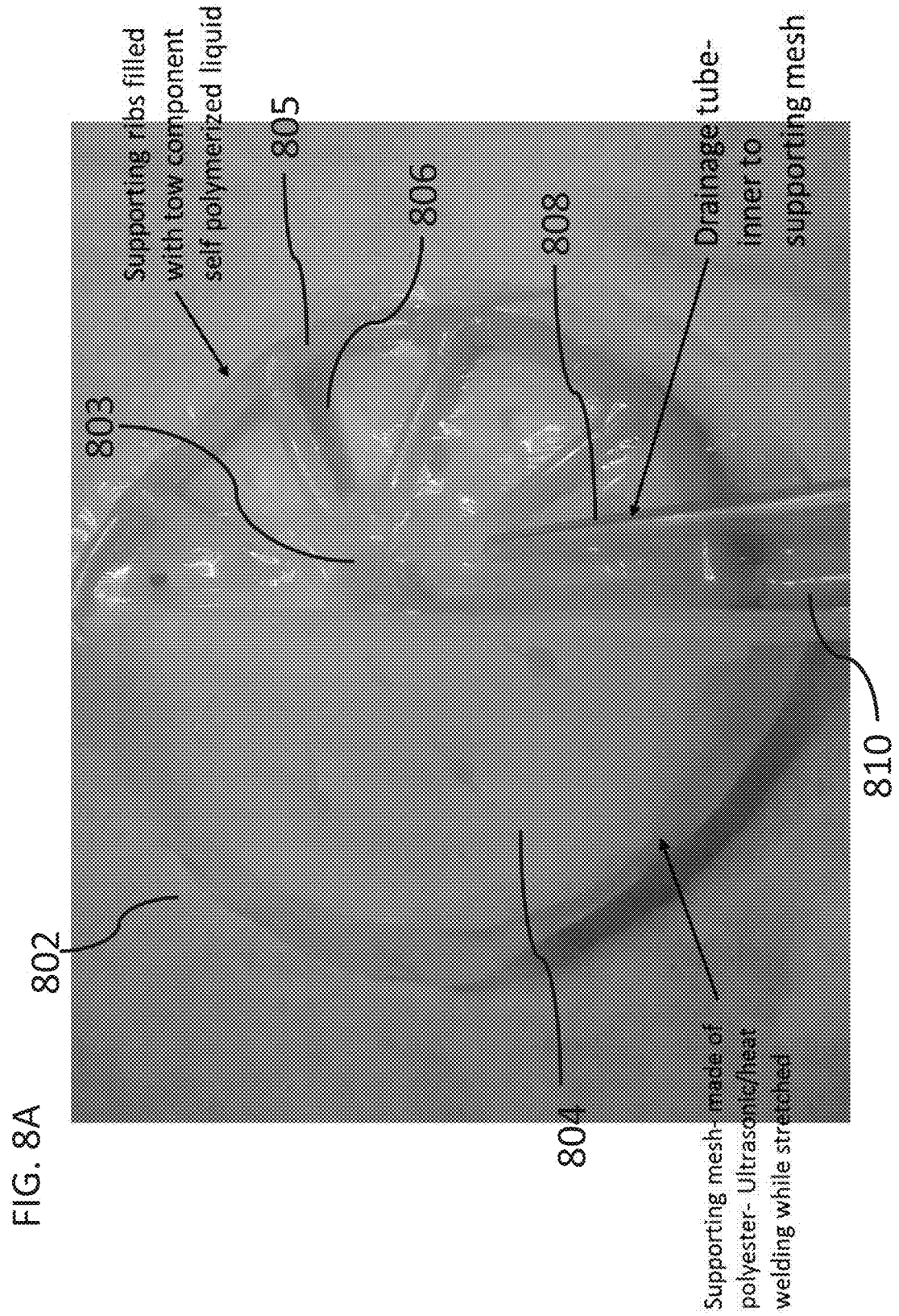

Reference is now made to FIG. 8A, depicting a chamber with an inner gel-filled skeleton, according to some embodiments of the invention.

According to some exemplary embodiments, a chamber, for example chamber 802 comprises an inner skeleton covered with a membrane, for example membrane 804. In some embodiments, the inner skeleton comprises a central tubular ring 803 with at least one tubular rib extending from the central tubular ring 803. Alternatively, the inner skeleton comprises an external tubular ring 805 surrounding the periphery of the chamber 802, with at least one tubular rib 806 extending from the external tubular ring 805. In some embodiments, the at least one tubular rib contacts the central and the external rings. In some embodiments, the at least one tubular rib is fluidically connected to the external tubular ring 805 and/or to the central tubular ring 803.

According to some exemplary, a filling tube 810 is fluidically connected to the central tubular ring 803 and/or to the external tubular ring 805 and/or to the tubular ring 806 of the inner skeleton. In some embodiments, the inner skeleton is filled with a gel or a polymerizing fluid, optionally a self-polymerizing fluid or hydrogel or viscous fluid, for example sucrose added saline. In some embodiments, after the insertion of the gel or the self-polymerizing fluid the filling opening in the chamber is sealed. In some embodiments, fluids entering the chamber 802 pass freely between the inner skeleton elements without contacting the gel or the polymerized fluid. In some embodiments, the fluids entering through the membrane 804 into the chamber 802 are drained from the chamber 802 via a draining tube 810 connected to an opening in the chamber 802.

Figure 8B:
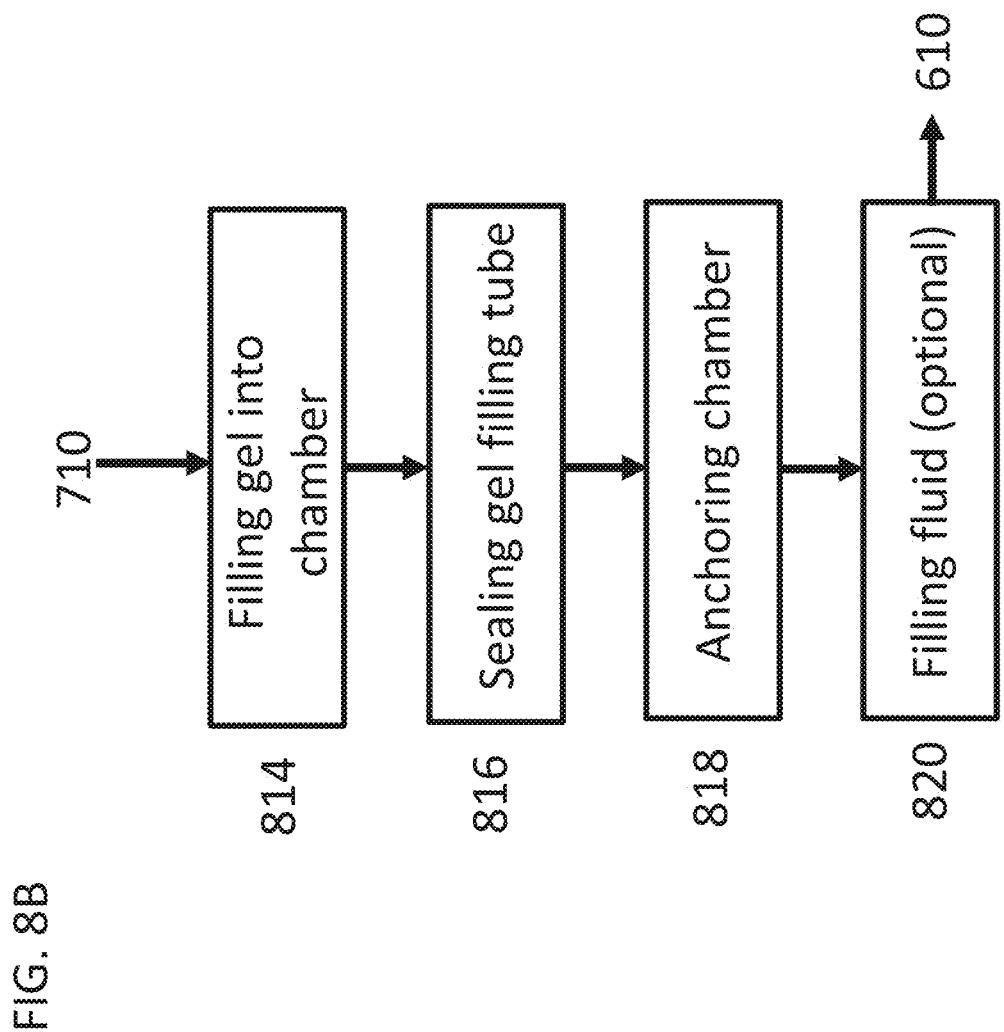

Reference is now made to FIG. 8B depicting a process for deploying a gel-filled chamber, according to some embodiments of the invention.

According to some exemplary embodiments, a chamber, for example a balloon chamber is unfolded, as described at 710 in FIG. 7B. In some embodiments, a gel or a polymerizing fluid is filled into the chamber at 814. In some embodiments, the gel is filled through a filling tube into an internal skeleton of the chamber. In some embodiments, the gel in the internal skeleton is isolated from fluids entering the chamber, for example fluids extracted from a tissue.

According to some exemplary embodiments, the gel filling tube is sealed at 816. The gel filling tube is sealed when a desired amount of gel or a polymerizing fluid is inserted into the chamber.

According to some exemplary embodiments, the chamber is anchored at 818. In some embodiments, the chamber is anchored after the internal skeleton reaches a desired rigidity or applies a desired internal force on the external surface of the chamber. In some embodiments, the chamber is anchored by at least one anchor positioned on the external surface of the chamber.

According to some exemplary embodiments, gel or fluid is filled at 820. In some embodiments, gel or fluid is filled into the chamber, optionally through a dedicated filling port. In some embodiments, the dedicated filling port is positioned coaxially and/or intraluminally to the draining tube.

According to some exemplary embodiments, once the draining port is open, the chamber is connected to a control unit, for example as described at 610 in FIG. 6.

Exemplary Removal and/or Replacement of System Components

According to some exemplary embodiments, in case of need of peritoneal chamber's extractions, the filler of the sack is initially removed (spiral braided or coiled tube, beads or a non-polymerizing gel). In some embodiments, after the removal of the filler, the sack loses its relative stiffness or rigidity and can be folded and manipulated to allow small incision/port for extraction. In some embodiment, the membrane sack is left in its original location after removal of the filler.

Exemplary Sources of Input Affecting Treatment

Reference is now made to FIG. 9A depicting parameters that affect a fluid filtration treatment, according to some embodiments of the invention.

According to some exemplary embodiments, a fluid filtration treatment 900 is affected by the patient's clinical parameters 902. In some embodiments, at least one treatment parameter is adjusted to the clinical condition of the patient. In some embodiments, the clinical parameter is determined based on the physical condition of the patient and/or based the results of tests and measurements of the clinical parameters. In some embodiments, the treatment is adapted to selected patients, for example warm and wet patients.

According to some exemplary embodiments, the treatment 900 is affected by the drained fluid content 904. In some embodiments, at least one parameter of the treatment is modified based on levels of chemical and/or biological components in the drained fluid.

According to some exemplary embodiments, the treatment 900 is affected by the system status 906. In some embodiments, at least one parameter of the treatment is modified following changes in the system status, for example an error or a malfunction in at least one component of the system. In some embodiments, the treatment is stopped or modified when a fluid absorbing unit and/or a fluid flow path of the system is clogged. In some embodiments, the treatment is modified, for example to allow replacement of at least one component of the implanted system.

According to some exemplary embodiments, the treatment 900 is modified following input received from other devices 908. In some embodiments, at least one parameter of the treatment 900 is modified following input received from sensors and/or devices, optionally implanted sensors and devices that are in communication with a control unit, for example control unit 106.

According to some exemplary embodiments, treatment 900 is affected by expert input 910. In some embodiments, an expert, for example a physician modifies a treatment from a remote computer optionally based on indications received from the patient and/or from the device. In some embodiments, the physician modifies the treatment following an improvement or deterioration in the patient's condition.

According to some exemplary embodiments, the treatment 900 is affected by patient input 912. In some embodiments, patient input 912 comprises patient compliance with treatment, for example whether the patient follows treatment instructions. In some embodiments, patient input 912 comprises the body posture and position. In some embodiments, patient input comprises the movement of the patient's body. Optionally, patient input 912 comprises food and water consumption of the patient, for example the amount of water the patient drinks in a selected time period.

Exemplary Types of Input Affecting the Treatment

Reference is now made to FIG. 9B depicting types of input affecting the fluid extraction treatment, according to some embodiments of the invention.

According to some exemplary embodiments, a fluid extraction treatment 900 is affected by clinical parameters 901. In some embodiments, the treatment or at least one treatment parameter is modified based on clinical parameters 901. Optionally, a different treatment plan is selected based on the measured clinical parameters 901. In some embodiments, the clinical parameters comprise body weight, for example as measured by the patient, blood pressure and/or heart rate. In some embodiments, the clinical parameters 901 comprise parameters related to the congestion level of the patient, for example parameters related to pulmonary congestion, Orthopnoea, paroxysmal nocturnal dyspnea, Peripheral (bilateral) oedema, Jugular venous dilation, Congested hepatomegaly, Gut congestion, ascites and/or Hepatojugular reflux. In some embodiments, the clinical parameters 901 comprise parameters related to the hypoperfusion level of the patient, for example parameters related to Cold sweated extremities, Oliguria, Mental confusion, Dizziness, and/or Narrow pulse pressure. In some embodiments, the clinical parameters are measured as an absolute value or in relation to a reference or a baseline value.

According to some exemplary embodiments, a fluid extraction treatment 900 is affected by sensory data 903. In some embodiments, sensory data 903 comprises data received by sensing the body of the patient, for example how hot or cold is the skin of the patient, how sweaty is the skin of the patient and/or sensing swallowing in the legs of the patient following edema.

According to some exemplary embodiments, a fluid extraction treatment 900 is affected by behavioral data 905. In some embodiments, behavioral data 905 comprises body movement and/or body posture related data. In some embodiments, behavioral data 905 comprises eating and drinking related data.

According to some exemplary embodiments, a fluid extraction treatment 900 is affected by alerts 907, for example alerts generated by an implanted system for extracting fluid. In some embodiments, the alerts 907 comprises alerts related to the status of the device, for example malfunction alerts. In some embodiments, the alerts 907 comprises alerts related to an outcome of the treatment, for example when an outcome of the treatment is not a desired outcome. In some embodiments, the alerts 907 comprises alerts related to the treatment compliance, for example when a patient acts in a way that is not following a selected treatment protocol.

According to some exemplary embodiments, a fluid extraction treatment 900 is affected by protocol adjustments 909. In some embodiments, the protocol adjustments 909 comprises adjustments related to the activation of a pump of an implanted fluid extraction device, for example the levels of the applied vacuum force, the duration of the pump activation and/or the duration of the duty cycles.

Exemplary General Process for Modifying a Treatment

Reference is now made to FIG. 9C depicting a general process for modifying a fluid extraction treatment, according to some embodiments of the invention.

According to some exemplary embodiments, patient are selected at 920. In some embodiments, the patients suitable for the treatment are selected based on their clinical condition. In some embodiments, patients suffering from acute heart failure, optionally with known chronic background are selected, optionally based on the hemodynamic and congestion profile of the patients. In some embodiments, patient are selected at 920 based on the congestion level and/or based on the hypoperfusion level of the patients. In some embodiments, the congestion level and/or the hypoperfusion level indicate the hemodynamic profile of the patients. In some embodiments, patients diagnosed with low congestion and without hypoperfusion levels are termed WARM-DRY patients. In some embodiments, patients diagnosed with high congestion levels and without or with low hypoperfusion levels are termed WARM-WET patients. In some embodiments, patients diagnosed with low congestion levels and high hypoperfusion levels are termed COLD-DRY patients. In some embodiments, patients diagnosed with high congestion and perfusion levels are termed COLD-WET patients.

In some embodiments, WARM-WET and/or COLD-WET patients are selected.

According to some exemplary embodiments, a treatment is determined at 922. In some embodiments, a treatment protocol is determined based on the clinical conditions on the patient. Alternatively, at least one treatment protocol parameter value is determined based on the clinical conditions of the patient. In some embodiments, a treatment protocol is determined based on a clinical classification of the patient, for example a WARM-WET, or a COLD-WET classification.

According to some exemplary embodiments, the treatment is initiated at 924. In some embodiments, the treatment is initiated after measuring baseline or reference values of clinical parameters related to the patient.

According to some exemplary embodiments, one or more parameters are measured at 926. In some embodiments, the measured parameters comprise parameters related to an outcome of the treatment. In some embodiments, the measured parameters comprise clinical parameters, behavioral parameters, mental parameters, sensory parameters and/or treatment related parameters. In some embodiments, congestion or congestion-proxy is measured at 926. Optionally, the congestion or congestion-proxy of interstitial fluids or extracted fluid is measured.

According to some exemplary embodiments, input is received at 928. In some embodiments, the input is received from a patient, a caregiver, a nurse, or a physician. Optionally, the input is received following an analysis of the measured parameters.

According to some exemplary embodiments, the treatment is modified at 930. In some embodiments, the treatment or at least one treatment parameter is adjusted based on the measured parameters and/or based on the received input. In some embodiments, the duration of the treatment and/or the force applied by a pump of the implanted system is modified. In some embodiments, the treatment and/or at least one treatment parameter is modified to adjust the treatment to a new clinical condition of the patient.

According to some exemplary embodiments, the pressure applied on the tissue and/or duty cycles of the pump are modified at 930, for example to assess the recovery time of the interstitial pressure, during treatment. In some embodiments, the pressure applied on the tissue and/or duty cycles of the pump are modified at 930 to adjust the treatment to the recovery rate of the interstitial pressure.

Exemplary Process for Modifying a Treatment Based on Clinical Measurements

According to some exemplary embodiments, for example in vascularity congested patients, the system is conjugated to an intravascular pressure monitor, as a proxy to venous congestion, and will work until ventricular filling pressures are reduced to normal values, or to a desired range of values.

According to some exemplary embodiments, for example in systemic volume overloaded patients, the system is based on impedance water assessment, body weight and the internal congestion-proxy monitor. In some embodiments, the system is adjusted to run slower, in vascularity congested patients compared to systemic volume overloaded patients.

According to some exemplary embodiments, in subjects suffering from the following conditions: (1) Left sided heart failure and underlying chronic kidney disease, (2) Right sided heart failure, excluding ascites conditions, (3) Bi-ventricular heart failure, (4) Fontan failure, (5) Pulmonary hypertension with systemic congestion, the fluid extraction treatment using the system and methods described herein is adjusted to extract fluid in a range of 150-500 ml/day.

According to some exemplary embodiments, in subjects suffering from the following conditions: (1) Chronic Kidney Disease in stages 4 and 5, (2) End stage renal disease, (3) Abdominal compartment syndrome, (4) Ascites conditions, related to cirrhosis, portal hypertension etc., the fluid extraction treatment using the system and methods described herein is adjusted to extract fluid in a range of 500-1000 ml/day.

According to some embodiments, a pre-determined treatment is modified, optionally automatically, based on clinical parameters measurements performed during the treatment. Reference is now made to FIG. 9D, depicting a process for modifying a fluid extraction treatment following clinical parameters measurements, according to some embodiments of the invention.

According to some exemplary embodiments, clinical parameters are measured at 932. In some embodiments, clinical parameters, for example clinical parameters 901 shown in FIG. 9B are measured during the treatment. Optionally, the clinical parameters are measured automatically by at least one sensor, for example sensors 122. Alternatively or additionally, the clinical parameters are measured by the patient, for example the weight, or the blood pressure of the patient or by an external sensor wirelessly connected to the device.

According to some exemplary embodiments, a condition of the patient is diagnosed at 934. In some embodiments, the condition of the patient is diagnosed based on the measured clinical parameters. In some embodiments, a hemodynamic profile of the patient is determined at 934, based on the measured clinical parameters. In some embodiments, a clinical condition related to the urinary system, for example the kidney condition and/or the heart and/or the blood condition is diagnosed at 934. In some embodiments, a clinical condition related to fluids movement between biological compartments, for example between the blood and the cells and/or between the blood and the urinary system is diagnosed at 934.

According to some exemplary embodiments, a clinical condition of the patient is staged at 936. In some embodiments, the clinical condition, for example a disease or a pathological condition is staged at 936. Optionally the clinical condition of the patient is staged based on the measured clinical parameters or any other measured parameter.

According to some exemplary embodiments, the treatment is modified at 930. In some embodiments the treatment and/or at least one treatment parameter is modified based on the measurement of the clinical parameters at 932. Alternatively or additionally, the treatment and/or at least one treatment parameter is modified based on the clinical condition diagnosis at 934 and/or the staging of the clinical condition at 936. In some embodiments, the treatment and/or at least one treatment parameter is modified to adjust the treatment to a new clinical condition of the patient.

Exemplary Process for Modifying a Treatment Based on Measurements of the Extracted Fluid According to some exemplary embodiments, a pre-determined treatment is modified, optionally automatically, based on measurements of the drained fluid performed during the treatment. Reference is now made to FIG. 9E, depicting a process for modifying a fluid extraction treatment following measurements of the extracted fluid, according to some embodiments of the invention.

According to some exemplary embodiments, the extracted fluid is measured at 940. In some embodiments, the extracted fluid content is measured at 940. In some embodiments, the levels of chemicals, minerals and biological agents, for example antibodies, proteins, vitamins, acids are measured in the extracted fluid. In some embodiments, the measured substances comprise Sodium levels, Potassium levels, Phosphate levels, Creatinine levels, Albumin levels, Urea levels or other biomarkers levels, for example Brain Natriuretic Peptide (BNP). In some embodiments, the concentration of the measured substances is determined. Optionally, the levels of the measured substances are compared to a reference or a baseline value. In some embodiments, the levels of the measured substances are compared to the levels of the substances in the blood.

According to some exemplary embodiments, a condition of the patient is diagnosed at 942 based on the extracted fluid measurements. In some embodiments, a hemodynamic profile of the patient is determined at 942, based on the drained fluid measurements. In some embodiments, a clinical condition related to the urinary system, for example the kidney condition and/or the heart and/or the blood condition is diagnosed at 942. In some embodiments, a clinical condition related to fluids movement between biological compartments, for example between the blood and the cells and/or between the blood and the urinary system is diagnosed at 942.

According to some exemplary embodiments, a clinical condition of the patient is staged at 944. In some embodiments, the clinical condition, for example a disease or a pathological condition is staged at 944. Optionally the clinical condition of the patient is staged based on the measurements of the drained fluid performed at 940.

According to some exemplary embodiments, the treatment is modified at 946. In some embodiments the treatment and/or at least one treatment parameter is modified based on the measurement of the extracted fluid performed at 940. Alternatively or additionally, the treatment and/or at least one treatment parameter is modified based on the clinical condition diagnosis performed at 942 and/or the staging of the clinical condition performed at 944. In some embodiments, the treatment and/or at least one treatment parameter is modified to adjust the treatment to a new clinical condition of the patient.

Exemplary Process for Modifying a Treatment Following Input from a Patient and/or an Expert According to some embodiments, a pre-determined treatment is modified, optionally automatically, based on input received from the patient and/or from an expert during or after the treatment. Reference is now made to FIG. 9F, depicting a process for modifying a fluid extraction treatment based on received input, according to some embodiments of the invention.

According to some exemplary embodiments, an input from the patient is received at 948. In some embodiments, the input from the patient comprises clinical parameters measured by the patient for example body weight or blood pressure. In some embodiments, the input from the patient comprises following steps of the determined treatment, for example drinking and/or eating regime, sleeping duration and/or body movements.

According to some exemplary embodiments, an input from an expert, for example a physician is received at 950. In some embodiments, the input from the expert comprises at least one treatment parameter and/or clinical parameter. In some embodiments, the input from the expert comprises additional treatment protocols and/or treatment instructions and/or suggested treatment modifications.

According to some exemplary embodiments, a condition of the patient is diagnosed at 952 based on the inputs received from the patient and/or from the expert. In some embodiments, a hemodynamic profile of the patient is determined at 952, based on the patient and/or the expert input. In some embodiments, a clinical condition related to the urinary system, for example the kidney condition, and/or the heart condition and/or the blood condition is diagnosed at 952. In some embodiments, a clinical condition related to fluids movement between biological compartments, for example between the blood and the cells and between the blood and the urinary system is diagnosed at 952.

According to some exemplary embodiments, a clinical condition of the patient is staged at 954, based on the inputs received for the patient and/or from the expert. In some embodiments, a disease or a pathological condition is staged at 944.

According to some exemplary embodiments, treatment compliance is determined at 956. In some embodiments, the compliance of the patient with the treatment is determined at 956 based on inputs received from the patient at 948. In some embodiments, the compliance of the patient with an overall treatment procedure, for example with a drinking and eating regime is determined.

According to some exemplary embodiments, an indication is delivered at 958. In some embodiments, the indication comprises a report, for example a compliance report. In some embodiments, the indication is delivered to the patient, optionally to a handheld device and/or to a computer that is in communication with the implanted system. Alternatively or additionally, the indication is delivered to the expert, for example the physician via a handheld device and/or a computer that is in communication with the implanted system. In some embodiments, the implanted system signals the handheld device and/or the computer to generate an indication, for example a human-detectable indication.

According to some exemplary embodiments, the treatment is modified at 960. In some embodiments the treatment and/or at least one treatment parameter is modified based on the inputs received from the patient and/or from the expert. Alternatively or additionally, the treatment and/or at least one treatment parameter is modified based on the clinical condition diagnosis performed at 952 and/or the staging of the clinical condition performed at 954. In some embodiments, the treatment and/or at least one treatment parameter is modified based on the treatment compliance determined at 956.

Exemplary Process for Device Maintenance

Reference is now made to FIG. 9G depicting a process for device maintenance, according to some embodiments of the invention.

According to some exemplary embodiments, the implantable device setup is determined at 961. In some embodiments, the device setup comprises activation parameters of a pump, for example pump 130. In some embodiments, the activation parameters of the pump comprises activation duration, number of activation cycles in a selected time period, and the intensity of vacuum force generated by the pump. In some embodiments, device setup comprises establishing a communication channel between the implanted system and an external device, for example a handheld device. In some embodiments, device setup comprises adjusting indication transmitting schedule, for example compliance report transmitting schedule. In some embodiments, the device setup comprises device calibration. In some embodiments, the determined setup comprises modifying and calibrating a learning algorithm for activating the device and/or for measuring parameters and/or for automatically modifying the treatment.

According to some exemplary embodiments, treatment is initiated at 962. In some embodiments, the device operates based on the determined device setup. Additionally, the device operates according to a treatment protocol stored in a memory of the device, for example memory 116.

According to some exemplary embodiments, the device status is determined at 964. In some embodiments, the device status is determined at pre-defined time points and/or upon request from a patient and/or from an expert. In some embodiments device status comprises battery charging status, pump activation status, fluid flow status, and/or fluid extraction status.

According to some exemplary embodiments, an indication is delivered at 966. In some embodiments, the indication is delivered if the determined device status is not a desired device status. In some embodiments, an indication is delivered at 966 if a device malfunction occurs. Alternatively or additionally, an indication is delivered if a device component should be replaced or repositioned, for example a membrane, a fluid absorbing unit, a catheter tube, a draining tube, batteries. In some embodiments, an indication is delivered if the battery should be charged.

According to some exemplary embodiments, at least one device component is replaced at 968. In some embodiments, the battery and/or the membrane and/or the draining tube and/or the fluid absorbing unit or the chamber are replaced.

Exemplary Treatment Plans

According to some exemplary embodiments, the device is implanted in patients after being acutely stabilized at the hospital, optionally with IV diuresis and/or ultrafiltration. In some embodiments, the device is implanted in patients after being diagnosed as oral diuretics resistant (to some extent) and optionally readmitting for the same condition.

According to some exemplary embodiments, in vascularity congested patients the device is conjugated to intravascular pressure monitor, optionally as a proxy to venous congestion. In some embodiments, the device comprises an internal congestion sensor or is connected to an internal or external congestion sensor. In some embodiments, the device works until ventricular filling pressures are reduced to normal values. In some embodiments, after reaching normal or near normal values, the device is activated for shorter time periods and/or applies reduced vacuum forces by the pump. In some embodiments, the system works until systemic peripheral congestion reaches normal values.

According to some exemplary embodiments, in patients diagnosed with systemic volume overload, the device is based on impedance water assessment, and/or body weight assessment and optionally on an internal congestion-proxy monitor.

According to some exemplary embodiments, the device is programmed with target drainage per day rate. Alternatively or additionally, the device calculates the required drainage rate to bring the internally measured congestion-proxy to its baseline value.

According to some exemplary embodiments, the device performs an optimization run in a predetermined schedule, for example every 1 to 6 hours, for example every 1, 2, 3, 4, 5, 6 hours or any intermediate value. In some embodiments, the device sweeps duty cycles in the range of: ON time: 20 to 180 seconds, for example 30-170 seconds in steps of 20 seconds or any shorter or longer time period, and OFF time: 60 to 600 seconds in steps of 30 seconds or any shorter or longer time period. Optionally the device sweeps pump power (speed) where pressure is allowed to be maintained in a range of $-5:-45$ kPa, for example in a range between $-5$ kPa and $-20$ kPa, $-15$ kPa and $-35$ kPa, $-20$ kPa and $-45$ kPa or any intermediate, smaller or larger value or range. In some embodiments, the minimal values providing the target drainage rate are set as a working point until the next optimization run. In some embodiments, the optimal working point that provides the best performance or fluid extraction efficiency is compared to a previously determined working point, and accounted for in respect to the target programmed draining rate.

According to some exemplary embodiments, when flow values during ON active cycle do not meet the averaged and required values, the device switches to a rest or a standby state and optionally runs a 'congestion-proxy' measurement. In some embodiments, internal pressure and flow sensors are utilized to evaluate congestion-proxy measurement. In some embodiments, baseline values are calibrated for each patient during a clinical assessment. In some embodiments, during operation, the device sweeps vacuum pressures (as detailed above) and/or ON:OFF duty cycles and optionally compares the recovery rate of intra-chamber pressure and obtained flow rate. In some embodiments, for same pressures and duty cycles, the faster the recovery time, the greater the congestion is. In some embodiments, the device also assesses presence of cavity and/or interstitial fluids through pressure-flow curves and/or local impedance measurement. In some embodiments, the 'congestion-proxy' measurement is used to assess whether greater operation variables are required and/or whether less volumes are available for drainage.

According to some exemplary embodiments, the system measures at least one physiological parameter related to the drinking and/or eating habits of the patient. In some embodiments, the system receives an indication from the patient, following eating or drinking. In some embodiments, the system activates the pump for longer times and/or with higher intensity following eating or drinking of the patient.

According to some exemplary embodiments, the system identifies if the patient is sleeping. In some embodiments, during a sleeping period of the patient, the system stops the activation of the pump.

According to some exemplary embodiments, the system measures values of congestion and/or an indication of congestion. In some embodiments, the system calculates from the measured values the interstitial pressure, and adjusts the protocol, at least one treatment protocol or the duty cycles of the pump to the calculated interstitial pressure.

Exemplary Experimental Results

Reference is now made to FIG. 10A, depicting differences in drainage rate between the device, for example a direct interface chamber and different peritoneal draining catheters, according to some embodiments of the invention. According to some exemplary embodiments, there is a 25 folds increase in draining rate when using a homogeneous semi-permeable membrane in direct contact with the tissue, compared to a discretely perforated catheter.

In some embodiments, for example as shown in FIG. 10A the difference of drainage rates (normalized to surface area) between 28 measurements from implanted "direct interface flat chamber" (on various types of membranes) and regular peritoneal catheters. In some embodiments, there is a 25 folds advantage of having a homogeneous semi-permeable membrane in direct contact with the tissue, rather than discretely perforated catheter.

Figure 10B:
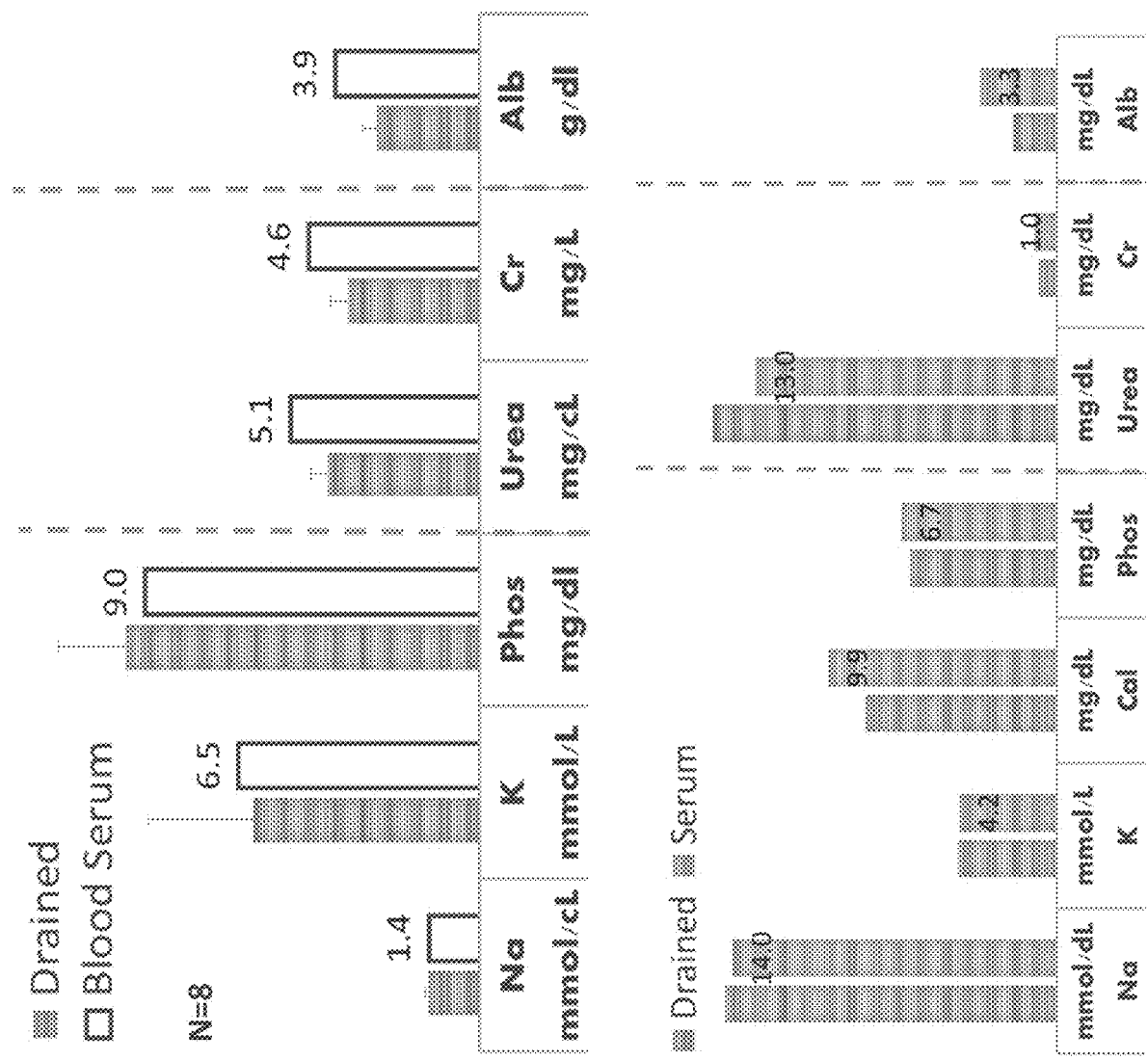

Reference is now made to FIG. 10B providing a comparison graph between the concentration of different substances in the drained fluid compared to the concentration of the substances in blood serum. In some embodiments, the levels of Potassium, Sodium and Phosphate are similar between the blood serum and the drained fluid. In some embodiments, the levels of Creatinine, Urea, and Albumin are lower in the drained fluid compared to the levels in the blood serum. In some embodiments, this comparison graph serves to evaluate the effect of increasing or lowering the fluid extraction rate on substances levels in the blood serum, for example when trying to minimize the albumin levels in the drained fluid.

Figure 10C:
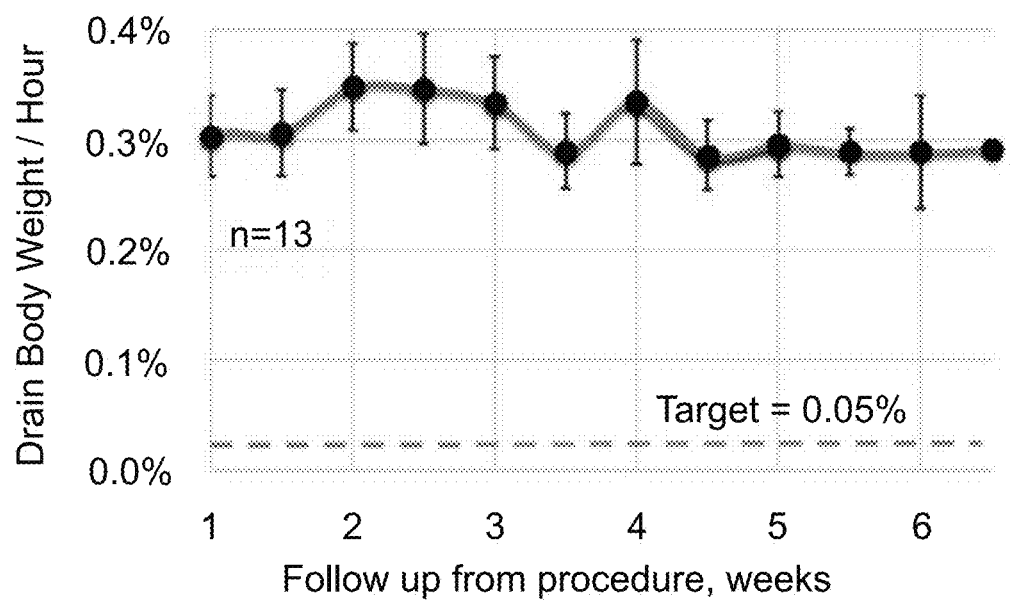

Reference is now made to FIG. 10C depicting a follow-up analysis of a fluid draining procedure over time, according to some embodiments of the invention. According to some exemplary embodiments, a disk shaped absorption chamber covered by semi-permeable membrane reaches drainage rates six times higher than a required relative drainage rate of 0.05% body weight per hour (1.2%/day), over a time period of more than 6 weeks. According to some exemplary embodiments, a PTFE disk shaped absorption chamber with 15 mm diameter one-sided orifice was covered by semi-permeable membrane. In some embodiments, the chamber was implanted in the peritoneum cavity of six normally hydrated rats. In some embodiments, a micro-catheter that drains the fluids from the absorption chamber was routed to percutaneous port. In some embodiments, drainage and sampling of fluids were conducted for more than 6 weeks. Optionally, obtained drainage rates are maintained above six times higher than required relative drainage rate of 0.05% body weight per hour (1.2%/day).

Figure 10D:
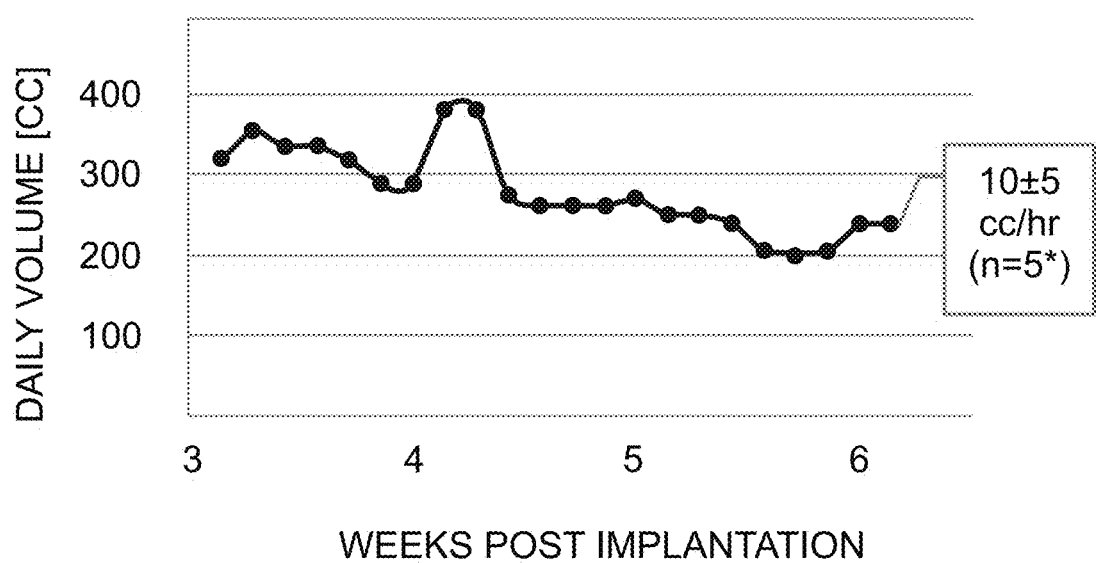

Reference is now made to FIG. 10D, depicting a follow-up analysis of a fluid draining procedure over time in pigs, according to some embodiments of the invention. According to some exemplary embodiments, an implanted disk shaped absorption chamber covered by a semi-permeable membrane reached averaged drainage values of 240 ml/day, in a time period of 3-6 weeks.

Figure 10E:
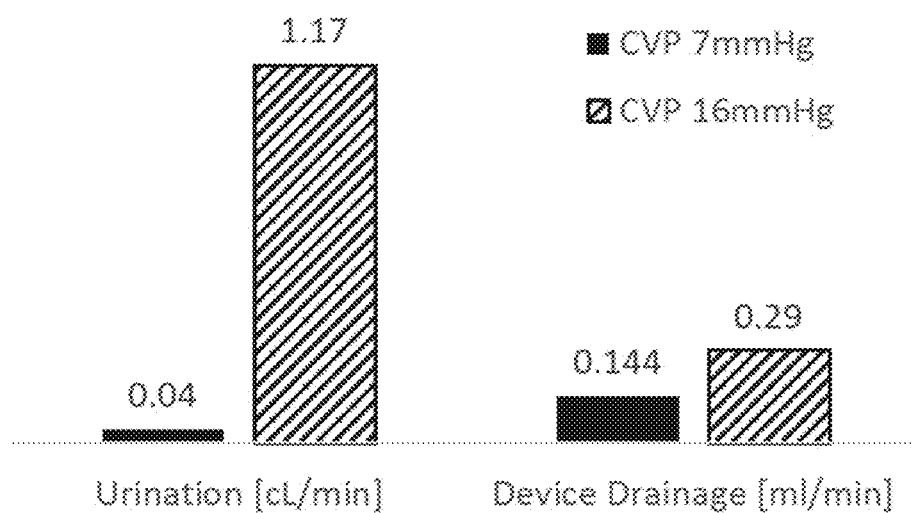

Reference is now made to FIG. 10E, depicting analysis results of filtration using the absorption chamber and device under acute volume overload, according to some exemplary embodiments of the invention. According to some exemplary embodiments, central venous pressure is increased from 7 mmHg to 16 mmHg, for example by injection of highly colloid ringer-lactate solution into the veins (12 liters venous overload within 3 hours in a PIG). In some embodiments, increasing the central venous pressure also increased the urination rate by 30 time, as shown in FIG. 10E. Additionally, the device increased the drainage rate by 2 folds under these conditions, which optionally demonstrates sensitivity to congestion level.

Figure 10F:
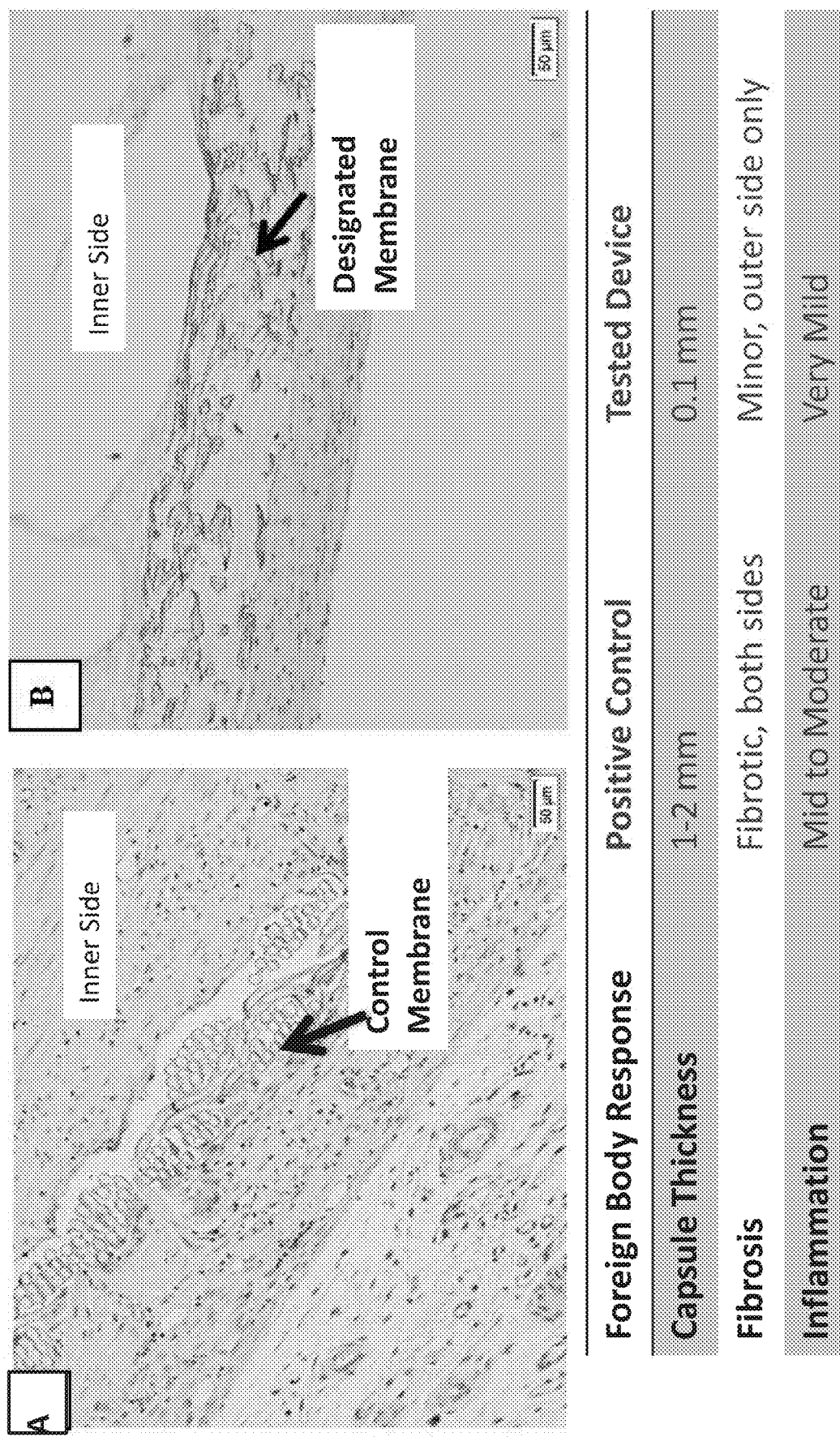

Reference is now made to FIG. 10F depicts a histological analysis of a membrane used in the implanted system, according to some embodiments of the invention. According to some exemplary embodiments, the histological analysis shows very mild foreign body response over the course of 1-month tissue growth phase in respect to a control device. In some embodiments, the analysis revealed minor fibrosis, mild inflammation, and a formation of a thinner capsule in the membrane used in the implanted system compared to a control membrane.

In FIG. 10F panel A, cells are visualized on both sides of the membrane (the nuclei of the cells are stained with blue) and the membrane is stained with light brown. When using a membrane of the tested device, cells are present only on the outer side of the membrane but not on the inner side (blue stained nuclei are not present at the inner side of the membrane), as shown in FIG. 10F panel B.

According to some exemplary embodiments, for example as shown in FIG. 10F a histological analysis showed very mild foreign body response over the course of 1-month tissue growth phase in respect to control device. In some embodiments, a thin capsule is created on the membrane following implantation.

According to some exemplary embodiments, the membrane comprises pores having a size in a range of 0.4-5 um, for example 0.4, 0.5, 0.8, 1, 2, 5 um or any intermediate size. In some embodiments, the membrane surface is treated, for example by hydrophilic Teflon. In some embodiments, the membrane surface is smooth, for example unlike the mesh fabric.

Reference is now made to FIG. 10G depicting a duty cycles comparison table, according to some embodiments of the invention. According to some exemplary embodiments, to avoid fluid extraction termination due to continuous draining, the device is activated in intervals according to duty cycles. In some embodiments, the maximal drainage volume and the maximal drainage rate are reached in a duty cycle of 60 seconds activation state followed by a 60 second standby state. In some embodiments, the implanted system calibrates the duty cycles per patient, optionally during a setup phase and/or during treatment. In some embodiments, the duty cycles are calibrated per patient, for example to reach the most efficient draining process. In some embodiments, the duty cycles are calibrated by the device by measuring the drainage volume, the average drainage rate and/or the flow rate. In some embodiments, the duty cycles are optimized for each patient based on at least some of the parameters presented in the table.

According to some exemplary embodiments, during continuous drainage the secretion stops after few minutes and is not retained, unless recovery is applied.

Figure 10H:
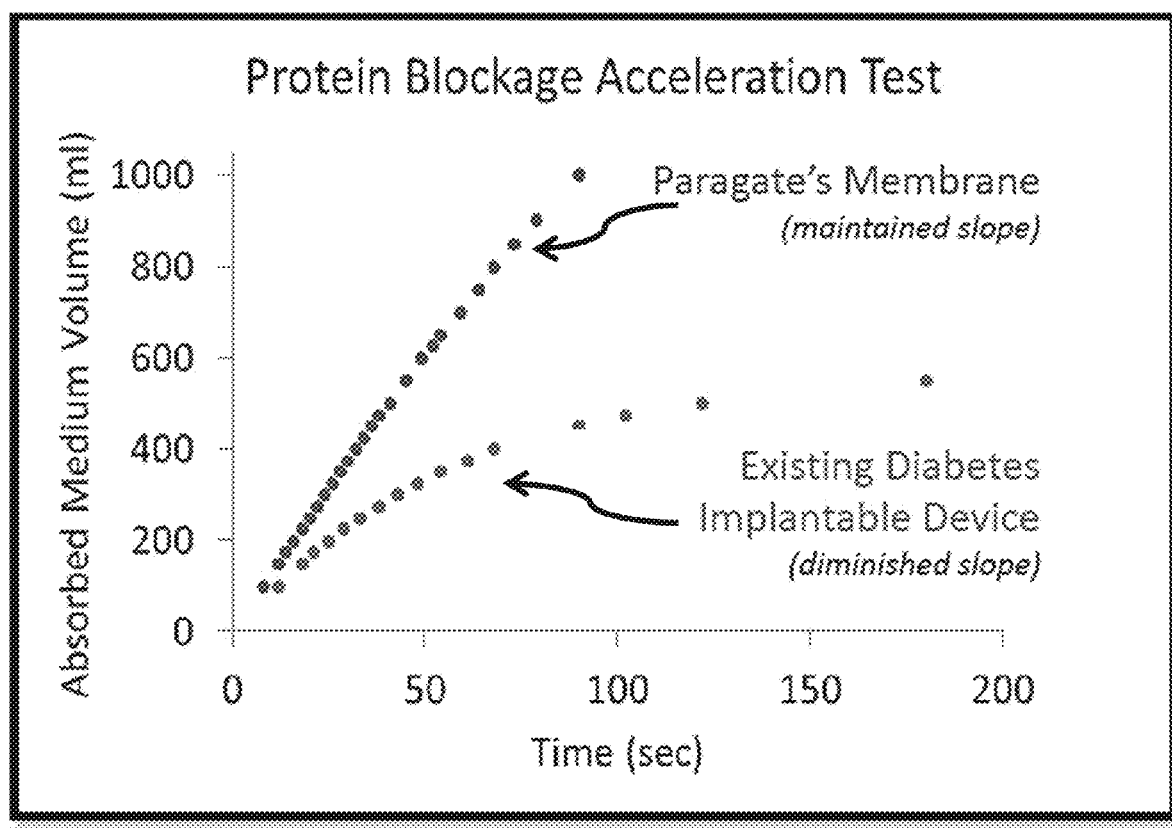

Reference is now made to FIG. 10H depicting the blockage rate due to protein clogging during an acceleration test, according to some embodiments of the invention.

According to some exemplary embodiments, a membrane, for example membrane 110 maintains a constant fluid extraction rate compared to an existing catheter, optionally by preventing or minimizing the clogging of the membrane pores.

Exemplary Pressure Changes within Fluid Extraction Chamber

According to some exemplary embodiments, a membrane associated with a fluid extraction chamber, for example fluid absorbing unit 104 shown in FIG. 1 is partially blocked, for example due to protein fouling processes. In some embodiments, changes in pressure within the fluid extraction chamber attenuates or prevents membrane blocking. In some embodiments, changes in pressure, optionally transient pressure changes are applied on the membrane, for example using a pushback mechanism.

According to some exemplary embodiments, an implantable system, for example system 102 shown in FIG. 1, continuously or intermittently applies uni-directional hydrostatic pressure gradient. In some embodiments, the applied pressure drives fluid passage through the covering membrane into the fluid extraction chamber lumen. In some embodiments, application of pressure pushback allows, for example, refreshing the membrane by optionally shaking and or vibrating the membrane without flushing the membrane. In some embodiments, membrane flushing with optionally fresh clean liquid and/or with previously drained fluid, imposes complications of introduction of clean fluid into an implantable device. Alternatively or additionally, membrane flushing imposes risk of contaminating the peritoneal chamber with infected liquid that was in fluid contact with the bladder.

According to some exemplary embodiments, the pressure changes optionally by application of the pressure pushback, for example to reach efficient membrane refreshing levels, for instance reducing membrane's aggregated protein content by 5% to 80% and restoring permeability in proportional manner the pressure changes are transient, for example to minimize backward fluid flow transfer through the membrane. Reference is now made to FIGS. 11A-11D depicting systems for generation of pressure changes within the fluid extraction chamber, according to some exemplary embodiments of the invention.

According to some exemplary embodiments, for example as shown in FIG. 11A, a fluid extraction chamber, for example an absorption chamber 1104 is associated with a membrane, optionally positioned within the chamber, on the outer surface of the chamber and/or that the outer surface of the fluid extraction chamber is made from the membrane. In some embodiments, the absorption chamber 1104 is connected via a tube to a pump, for example directional pump configured to apply negative pressure within the absorption chamber 1104. In some embodiments, fluid is pushed by the pump 1110 through outlet 1112, optionally into the bladder, renal pelvis, implanted reservoir or extracorporeally outside the body.

According to some exemplary embodiments, a control circuitry, for example a controller generates pressure changes by activating the pump intermittently. In some embodiments, the controller transiently deactivates the pump, and reactivates the pump after a short time period of up to 5 seconds, for example after a time period of 0.5 second, 1 second, 1.5 second or after any intermediate, smaller or larger time period. In some embodiments, the control circuitry activates the pump intermittently according to a protocol optionally stored in a memory of the system, for example memory 116 shown in FIG. 1.

According to some exemplary embodiments, the absorption chamber 1104 is connected to the pump 1110 through at least one valve for example a solenoid valve 1120 and/or a pinch valve 1116. In some embodiments, for example as shown in FIG. 11A, the absorption chamber 1104 is connected through the inlet tubing 1106 to a compliance tube 1114, for example a compliance tube of a pinch valve 1116. In some embodiments, a valve, for example the solenoid valve 1120 is connected to the compliance tube 114. In some embodiments, fluid flows from the absorption chamber 1104 through the compliance tube of the pinch valve 1116, and the solenoid valve 1120. In some embodiments, the at least one valve positioned in the fluid flow path between the absorption chamber 1104 and the pump 1110, for example solenoid valve 1120 and/or pinch valve 1116 is electrically connected to a controller of the system 1102, for example controller 1118. Optionally, the controller is electrically connected to the pump 1112 and controls the pump activity.

According to some exemplary embodiments, activation of the at least one valve, for example the solenoid valve 1120 and/or the pinch valve changes pressure levels within the inlet tubing 1106 and the absorption chamber 1104. In some embodiments, the changes in pressure levels allows detachment and/or removal of proteins and other bioactive compounds from at least one membrane associated with the absorption chamber. In some embodiments, the pressure changes caused by activation, optionally transient activation of the solenoid valve 1120 and/or the pinch valve 1116 are transient pressure changes. Additionally or alternatively, the pressure changes are gradual pressure changes.

According to some exemplary embodiments, for example as shown in FIG. 11B, the absorption chamber 1104 is connected through inlet tubing to the pump 1110. In some embodiments, the pump 1110 applies negative pressure through the inlet tubing 1106 on the absorption chamber and on a membrane associated with the chamber. In some embodiments, a valve, for example a solenoid valve 1142 is placed on a fluid flow path bypassing the pump 1110, for example flow path 1138. In some embodiments, flow path 1138 interconnects the inlet tubing 1106 and an outlet 1140 of the pump 1110. Optionally, activation of the solenoid valve 1142 is under the control of controller 1144. In some embodiments, activation of the solenoid valve 1142, for example opening and closing of the valve, causes changes in pressure, for example a short increase in positive pressure within the absorption chamber which leads to detachment and/or removal of bioactive compounds from a membrane associated the chamber. In some embodiments, these pressure changes are transient and/or gradual.

According to some exemplary embodiments, for example as shown in FIG. 11C, system 1150 comprises, at least one pump, for example pump 1162 positioned on a flow path, for example a tube, between an inlet tubing 1106 and an outlet 1160 of the pump 1110. Alternatively, the pump 1162 is positioned on a flow path, for example a tube, between a compliance tube, for example a compliance tube 1158 exiting the pump 1110 and the inlet tubing 1106. In some embodiments, the pump 1162 actively applies positive pressure within the inlet tubing 1106 and the absorption chamber, optionally causing detachment and/or removal of proteins and other bioactive compounds from a membrane associated with the chamber.

According to some exemplary embodiments, the pump 1162 comprises a diaphragm or positive displacement pump which applies opposite bursts of fluid into the inlet tubing 1106 to increase the positive pressure within the absorption chamber. In some embodiments, the activation of the pump 1162 is under the control of a controller 1164, electrically connected to the pump 1162. Optionally, the pump 1162 is activated based on signals received from sensor 1152, for example a pressure sensor configured to measure pressure in the inlet tubing 1106 and/or within the absorption chamber 1104. In some embodiments, the controller 1164 which controls the activation of pump 1162 is electrically connected to the sensor 1152.

According to some exemplary embodiments, for example as shown in FIG. 11D, the pump of system 1170, for example bi-directional pump 1172 which generates negative pressure within the absorption chamber 1104 is also configured to generate positive pressure. In some embodiments, the pump 1172 is configured to generate positive pressure, optionally transient bursts of positive pressure, within the inlet tubing 1106 and the absorption chamber 1104. Alternatively and/or additionally, the pump 1172 is configured to generate transient bursts of negative pressure within the absorption chamber. In some embodiments, the pump 1172 comprises a bi-directional pump, for example a bi-directional gear pump.

According to some exemplary embodiments, generation of positive pressure within the absorption chamber is performed while fluid backflow, for example from the bladder or any other chamber connected to the outlet tube into the inlet tubing and/or the absorption chamber. In some embodiments, a unidirectional valve, for example a check valve is positioned on the outlet tube, for example to prevent backflow of fluid into the system.

Reference is now made to FIG. 11E depicting pressure changes in an absorption chamber, according to some exemplary embodiments of the invention. According to some exemplary embodiments, negative pressure is applied at T0, for example by a pump, optionally a vacuum pump. In some embodiments, the negative pressure is applied on a draining tube connected to the absorption chamber and/or within the absorption chamber, for example to extract fluid directly from a tissue into the lumen of the absorption chamber. Optionally, when the negative pressure is applied, the surface of the chamber is tightly attached to the tissue, optionally a flat surface of the chamber, is tightly attached to the tissue surface.

According to some exemplary embodiments, negative pressure levels are reduced by applying lower levels of negative pressure or positive pressure at T1, for example using the devices and/or features described in FIGS. 11A-11D. In some embodiments, the total pressure level L1, which is the combination of the negative pressure, for example vacuum and the applied positive pressure is a negative pressure level below pressure level 0. In some embodiments, the total pressure level L1 is a negative pressure level to maintain tight attachment between the absorption chamber, and/or a membrane associated with the absorption chamber and the tissue. Additionally, the total pressure level L1 is a negative pressure, for example to prevent the release of fluid and other material from the lumen of the absorption chamber into a space between the absorption chamber and the tissue, and/or directly into the tissue.

According to some exemplary embodiments, the reduced negative pressure period (T2–T1) is determined by a control circuitry of the system, optionally based on one or more treatment protocols and/or activation parameters stored in a memory of the system. Additionally or alternatively, the time T1 for application of lower negative pressure levels, and/or the time period between consecutive intervals of lower negative pressure applications and/or positive pressure applications (T3–T1 or T3–T2) is determined by a control circuitry of the system, optionally based on one or more treatment protocols and/or activation parameters stored in a memory of the system.

Exemplary Verification Experiment for Testing Positive Pressure Application

Reference is now made to FIGS. 12A and 12B depicting the results of an experiment for testing the effect of positive pressure on membrane protein expression. In the experiment the effect of positive pressure application, also termed herein as "pushback" was tested on a fibroblast cell culture. The effect was tested in three different experimental setups:
  A. Static immersion of membrane inside buffered active fibroblasts solution (no dynamic flow) for period of 3 weeks
  B. Dynamic setting, where solution is circulated through the tested membranes, for same period
  C. Pushback setting, where transient bursts of reversed flow was applied twice a day, for same period A shown in FIG. 12A, dense and low porosity membranes corresponding sub-micron range, that tend to block more rapidly, in test conditions, for example as shown in FIG. 10F, can benefit of pushback, by restoring protein level to those exhibited in static immersion (that don't impair their permeability). Application of transient bursts of reversed flow (pushback) on 0.45 µm membranes placed in circulation reduced protein concentration on the membrane in about 50% compared to membranes placed in circulation only (Dynamic).

As shown in FIG. 12B, to confirm the ability to apply transient pressure changes within the absorption chamber by pushback of small volume of liquid, the change in pressure was recorded during transient pushback of different volumes of fluid back into the chamber (1 to 3 ml into a chamber volume of approximately 80 ml).

The test shows that in environment of a non-dense liquid, with limited compliance of chamber, due to its inner skeleton, limited elasticity of membrane compound and due to baseline vacuum, transient return of small volume (1-4% of volume) allows modification of pressure gradient applied on the membrane by up to 75-85%.

Exemplary Introduction System

Reference is now made to FIGS. 13A and 13B, depicting a delivery system for the absorption chamber, according to some exemplary embodiments of the invention. According to some exemplary embodiments, a delivery system 1302 comprises a hollow distal liner 1306, which includes a folded absorption chamber, for example a permeable sack. In some embodiments, the folded absorption chamber is folded within the hollow distal liner 1306. In some embodiments, the folded absorption chamber comprises a membrane or is made at least partly from the membrane, as described herein. In some embodiments, the hollow distal liner 1306 is slidable over an introducer shaft 1304, optionally an extendable and/or a telescopic introducer shaft. In some embodiments, the introducer shaft 1304 is slidable over a fixed internal shaft 1317. In some embodiments, the introducer shaft 1304 and/or the fixed internal shaft 1317 are connected to a handle 1308, for example a rotatable handle configured to allow maneuvering of the introducer shaft coupled to the absorption chamber into a desired position within a body cavity, for example within the peritoneum. Optionally, the handle 1308 is configured to maneuver the introducer shaft and the coupled absorption chamber to a desired position and/or orientation that allows attachment, optionally tight attachment of at least part of the absorption chamber and/or the membrane to a tissue surface.

According to some exemplary embodiments, a proximal end of the introducer shaft 1304 is connected to a tube, for example a corrugated tube 1312 which is optionally made of Silicone. In some embodiments, the corrugated tube 1312 is a compressible elastic concertina tube. In some embodiments, the delivery system 1302 comprises a cartridge 1310. In some embodiments, the cartridge 1310 comprises a braided skeleton tube, for example tube 338 shown in FIG. 3M. In some embodiments, the braided skeleton tube is spirally wounded within the cartridge, for example to reduce storage volume within the cartridge 1310. In some embodiments, a cartridge opening is connected to a proximal opening of the corrugated tube 1312. In some embodiments, a user advances the stored braided skeleton tube stored in the cartridge 1310 through the corrugated tube 1312 and through a lumen of the introducer shaft into the absorption chamber.

According to some exemplary embodiments, the absorption chamber is deployed prior to the advancement of the braided skeleton tube from the cartridge 1310 into the deployed and folded absorption chamber. Alternatively, the braided skeleton tube is advanced from the cartridge 1310 into the absorption chamber during the unfolding of the absorption chamber. Optionally, when the absorption chamber is deployed and comprises the braided skeleton tube, the handle is used to attach a flat surface of the absorption chamber with a surface of the tissue.

According to some exemplary embodiments, the cartridge comprises at least one opening, for example a flushing port 1314 and/or a venting luer 1316, optionally connected to a proximal end of the braided skeleton tube placed within the cartridge 1310. In some embodiments, the venting luer allows venting, for example for sterilization, and/or flushing, for example to reduce friction when the braided skeleton tube stored within the cartridge 1310 is advanced into the absorption chamber. In some embodiments, the flushing port is configured to allow flushing and reduce friction, as described above. Alternatively or additionally, the flushing port allows to introduce a stylet or a guide wire, to assist with the absorption chamber inside the body cavity, for example inside the peritoneum.

According to some exemplary embodiments, the system 1302 comprises at least one safety controller, for example a release safety catch 1311. In some embodiments, the release safety catch 1311 is used to ensure intentional release of the absorption chamber within the body cavity. In some embodiments, the release safety catch 1311 controls the movement of the handle 1308. Alternatively, the release safety catch controls the advancement of the braided skeleton tube through the introducer shaft 1304 into the unfolded absorption chamber. Alternatively or additionally, the safety catch prevents the release of the introduction system from the absorption chamber.

According to some exemplary embodiments, for example as shown in FIGS. 14A-14D, at least part of a port connector 1404, for example a distal section, is positioned within an opening 1401 of the absorption chamber 1402. In some embodiments, a proximal section of the port connector is placed within a distal partly splitted section 1406 of fixed internal shaft 1317. In some embodiments, a gripping member 1315 is connected to the outer surface of the shaft 1408, and is configured to allow gripping and retraction of the shaft 1408 which is optionally a movable shaft. In some embodiments, the distal end of shat 1408 is positioned around the distal partly splitted section 1406 and prevents the opening of the partly splitted section 1406. In some embodiments, retraction of shaft 1408, for example sliding the shaft 1408 over the fixed internal shaft 1317 relieves the external pressure applied on the partly splitted section 1406.

Exemplary Port Connector

Reference is now made to FIG. 14E depicting a port connector, according to some exemplary embodiments of the invention. According to some exemplary embodiments, a port connector 1422 comprises a distal section 1424 and a proximal section 1426. In some embodiments, the distal section is shaped and sized to be positioned within an opening of an absorption chamber. Optionally, an external diameter of the distal section is smaller than the external diameter of the proximal section 1426. In some embodiments, the external diameter of the proximal diameter is adjusted to fit inside a partly splitted section of a fixed internal shaft, for example a partly splitted section 1406 of shaft 1408. In some embodiments, one or friction increasing elements, for example O-rings 1428 and 1429 allow to increase friction between a tube inserted into the port connector 1422 and the connector. In some embodiments, a tube connector positioned at the distal end of the tube is inserted through opening 1433, and interacts with inner surfaces 1425 positioned in the internal lumen of the distal section of the port connector. In some embodiments, the inner surface applies friction forces on the tube connector.

According to some exemplary embodiments, the proximal section 1426 of the port connector 1422 comprises one or more bumps and/or grooves and/or openings, for example grooves 1427 in the external surface and/or the internal surface of the proximal section 1426. In some embodiments, the one or more bumps and/or grooves and/or openings are used to allow gripping or release of the proximal section 1426, for example for interacting with the partly splitted section 1406 shown in FIGS. 14C and 14D. In some embodiments, the one or more bumps and/or grooves and/or openings are used to increase friction and/or for interlocking the proximal section during deployment of the absorption chamber and/or when the absorption chamber is extracted away from the subject.

According to some exemplary embodiments, applying external force on the proximal section, for example by an extraction chamber gripping device while pulling the tube from the internal lumen allows to retract the tube from the absorption chamber. In some embodiments, gripping the proximal section 1426 allows, for example extraction of the absorption chamber away from body. In some embodiments, a port connector, for example port connector 1422 with conical surface and two O-rings, provides certain connector locking force and about 4 times higher release force, for example for retraction of the for extraction of the inner tube away from the absorption chamber.

Exemplary Absorption Chamber Unfolding

According to some exemplary embodiments, a folded absorption chamber is unfolded when released from an envelope or a casing. In some embodiments, the folded absorption chamber unfolds when a self-expanding element expands, for example to a relaxed state. Alternatively or additionally, the folded absorption chamber unfolds when fluid is pushed into the folded absorption chamber. Optionally, the chamber unfolds when gas, for example air is pushed into the chamber through the chamber opening. Reference is now made to FIG. 15, depicting a self-expandable absorption chamber, according to some exemplary embodiments of the invention.

According to some exemplary embodiments, an absorption chamber, for example absorption chamber 15 is a self-expandable absorption chamber. In some embodiments, the absorption chamber 1502 comprises a self-expandable internal scaffold, for example a thin wire, configured to be opened to a relaxed state upon release of the absorption chamber from a casing or an envelope. In some embodiments, expansion of the self-expandable internal scaffold applies force on the internal surface of the absorption chamber, for example to maintain a flat and/or a thin shape of the absorption chamber.

Exemplary System Introduction Process

According to some exemplary embodiments, the peritoneum of a subject is inflated. In some embodiments, the peritoneum is inflated by introduction of gas, for example air into the peritoneum cavity. Optionally, the peritoneum is inflated by insertion of a tube connected to an air source at least partly into the peritoneum cavity.

According to some exemplary embodiments, a catheter distal end is introduced through the peritoneum cavity into the bladder of a subject. In some embodiments, a proximal end of the catheter, which is the catheter end that is positioned away from the bladder, is positioned outside the body. Alternatively, the proximal end of the catheter is positioned within the peritoneum cavity. Optionally, the catheter is a pigtail catheter.

According to some exemplary embodiments, the hollow distal liner 1306 which comprises a folded absorption chamber is introduced through an opening the abdominal wall into the peritoneum cavity. Optionally, the hollow distal liner 1306 with the folded absorption chamber is introduced through an opening of a trocar catheter into the peritoneum cavity.

According to some exemplary embodiments, when the hollow distal liner 1306 is at a desired location within the peritoneum cavity, the distal liner 1306 is retracted in direction 1305 towards handle 1308. In some embodiments, the distal liner 1306 is retracted by gripping and retracting gripping member 1303 positioned on the distal liner 1306, optionally at a proximal end of the distal liner 1306. In some embodiments, retraction of the distal liner unfolds the absorption chamber. Optionally, retraction of the distal liner 1306 exposes the absorption chamber within the peritoneum cavity.

According to some exemplary embodiments, a tube positioned within the cartridge 1310, for example a braided skeleton tube is advanced into the folded absorption chamber by pressing the corrugated tube, for example to hold the braided skeleton tube and moving the tube in direction 1307. In some embodiments, the tube positioned within the cartridge 1310 comprises a silicon tube wrapped with a metal mesh configured to protect the inner silicon tube from compression forces. In some embodiments, the metal mesh includes one or more visual indicators, for example to monitor the advancement of the mesh from the cartridge into the absorption chamber. In some embodiments, pressing the corrugated tube allows to hold the metal mesh surrounding the tube and to move the metal mesh and the inner tube in direction 1307 into the folded absorption chamber.

According to some exemplary embodiments, the metal mesh and the inner tube are advanced into the folded absorption chamber while fluid is introduced through the flushing port 1314 and/or through the venting luer 1316, for example to reduce friction between the metal mesh and the inner surface of the absorption chamber.

According to some exemplary embodiments, an indication is provided when a desired length of the metal mesh and the inner tube is placed within the absorption chamber. Optionally, the indication is a visual indication, delivered through a window or an opening in the cartridge 1310 and/or the introducer shaft. In some embodiments, the metal mesh and the inner tube are advanced into the absorption chamber until a lock for example an interference lock, placed on the metal mesh and/or inner tube is locked within a proximal section of a port connector positioned at least partly within the absorption chamber, for example port connector 1404 shown in FIG. 14A. In some embodiments, the interference lock on the metal mesh prevents movement of the metal mesh and/or the inner tube relative to the absorption chamber and/or relative to the port connector.

According to some exemplary embodiments, when an indication is provided and/or when the interference lock locks the metal mesh and/or the inner tube, a safety catch, for example safety catch 1311 shown in FIG. 13B, is removed. In some embodiments, the safety catch prevents the release of the introduction system from the absorption chamber, for example by preventing further retraction of the gripping member 1315 towards handle 1308. In some embodiments, the gripping member 1303 of the distal liner 1306 interconnects with the gripping member 1315, and is used for retraction of the gripping member 1315 in direction 1313 towards the handle 1308.

According to some exemplary embodiments, retraction of the shaft 1304, allows a partly splitted distal section, for example partly splitted section 1406 shown in FIG. 14C to open and release the absorption chamber within the peritoneum. In some embodiments, retraction of the introduction system, allows a proximal opening of a tube connected to the absorption chamber to be positioned outside the body or within the peritoneum.

According to some exemplary embodiments, a control unit, for example the control unit 106 shown in FIG. 1 or the control unit 514 shown in FIG. 5E is connected to the proximal opening of the tube and to the proximal opening of a catheter. In some embodiments, the control unit is then positioned inside the body, for example subcutaneously. Alternatively, the control unit and the distal end of the catheter are positioned outside the body, for example to allow draining of fluid from the absorption chamber into an external container.

It is expected that during the life of a patent maturing from this application many relevant fluid extraction devices will be developed; the scope of the term fluid extraction is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A fluid extraction implantable system shaped and sized to be implanted in a patient body, comprising:
   an implantable fluid extraction chamber, comprising:
      a permeable sack comprising an inner lumen, wherein said permeable sack is preshaped to form a flat and thin body, wherein said sack comprises an opening;
      an elastic internal scaffold configured to be deployed through said opening into said inner lumen of said sack after the permeable sack is introduced into the patient body, wherein said elastic internal scaffold is configured to stretch said sack to maintain said flat and thin body of said sack after said elastic internal scaffold is deployed into said inner lumen.

2. The system according to claim 1, wherein said elastic internal scaffold is a rigid elastic internal scaffold configured to prevent inward collapse of the permeable sack when vacuum is applied at an inner lumen of the permeable sack.

3. The system according to claim 1, wherein said chamber is shaped and sized to be positioned within the peritoneum.

4. The system according to claim 3, comprising:
   a draining tube connected to said opening of said sack;
   a control unit connected to said draining tube and comprises a pump, wherein said control unit activates said pump to apply negative pressure on said draining tube.

5. The system according to claim 1, further comprising a porous homogeneous membrane layer on the outer surface of said sack.

6. The system according to claim 5, wherein a largest dimension of pores of said membrane is smaller than 10 micrometer.

7. The system according to claim 5, comprising at least one implanted physiological sensor connected to said control unit, wherein said at least one implanted physiological sensor is configured to measure values of at least one physiological parameter related to said patient, and wherein said control unit is configured to control the activation of said pump according to said measured values of said at least one physiological parameter.

8. The system according to claim 5, wherein said at least one physiological parameter comprises an indication of congestion.

9. The system according to claim 1, further comprising a porous membrane within a cavity of said sack.

10. The system according to claim 1, wherein said sack is at least partly made from a porous membrane layer.

11. The system according to claim 1, wherein said internal scaffold comprises an inner elongated stylet positioned inside a lumen of said internal scaffold, wherein said stylet maintains said thin body of said permeable sack.

12. The system according to claim 11, wherein said inner stylet has a flattened thinned cross section or a rounded cross section.

13. The system according to claim 1, wherein said internal scaffold comprises a braided tube.

14. The system according to claim 1, wherein said internal scaffold comprises a connector, and wherein said connector restricts the movement of said internal scaffold relative to said permeable sack.

15. The system according to claim 1, wherein said permeable sack comprising two flat layers connected to each other along the periphery of said layers;
   and wherein said two flat layers are connected in at least one connection point in a region enclosed by said periphery.

16. The system according to claim 1, wherein said internal scaffold comprises a tube or a plurality of beads, configured to conform to a shape of tissue contacting said permeable sack.

17. The system according to claim 1, wherein said permeable sack is preshaped to form a fluid extraction chamber having a flat and thin shape connected to a draining tube and comprising at least one external flat surface, wherein said at least one external flat surface is configured to be attached to a tissue surface when a negative pressure is applied on said draining tube, wherein said chamber extracts fluids from said tissue by applying said negative pressure through said flat surface on said attached tissue surface.

18. The system according to claim 1, wherein said flat and thin body of said permeable sack comprises a flat and elastic external surface.

19. The system according to claim 1, wherein said permeable sack is configured to be introduced in a folded state into said patient body and to be unfolded in said patient body.

20. The system according to claim 19, wherein said elastic internal scaffold is configured to stretch said permeable sack to maintain said permeable sack unfolded after said elastic internal scaffold is deployed into said inner lumen.

21. A method for deploying a fluid extraction implantable system, comprising:
   introducing a flattened fluid extraction chamber having a draining outlet into a body cavity;
   inserting following said introducing an elastic internal scaffold into a lumen of said chamber in order to shape said flattened chamber positioned in said body cavity;
   connecting said draining outlet to a sink.

22. The method according to claim 21, comprising connecting said internal scaffold to a port of said flattened chamber for restricting the movement of said internal scaffold relative to said flattened fluid extraction chamber.

23. A fluid extraction implantable system shaped and sized to be implanted in a patient body, comprising:
   an implantable fluid extraction chamber, comprising:
      a permeable sack preshaped to form a flat and thin body, wherein said sack comprises an opening;
      an elastic internal scaffold configured to be deployed through said opening into said sack after the permeable sack is introduced into the patient body, wherein said elastic internal scaffold stretches said sack to maintain said flat and thin body of said sack;
      an outlet connector in said opening configured to connect a draining tube to said permeable sack.

* * * * *